(12) United States Patent
Lieb et al.

(10) Patent No.: US 6,271,180 B2
(45) Date of Patent: *Aug. 7, 2001

(54) SUBSTITUTED PHENYL KETO ENOLS AS PESTICIDES AND HERBICIDES

(75) Inventors: Volker Lieb; Hermann Hagemann, both of Leverkusen; Arno Widdig, Odenthal; Michael Ruther; Reiner Fischer, both of Monheim; Thomas Bretschneider, Lohmar; Christoph Erdelen, Leichlingen; Ulrike Wachendorff-Neumann, Neuwied; Alan Graff, Köln; Udo Schneider, Leverkusen, all of (DE)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/550,105

(22) Filed: Apr. 14, 2000

Related U.S. Application Data

(62) Division of application No. 09/155,637, filed as application No. PCT/EP97/01426 on Mar. 21, 1997.

(30) Foreign Application Priority Data

| Apr. 2, 1996 | (DE) | 196 13 171 |
| Nov. 29, 1996 | (DE) | 196 49 665 |

(51) Int. Cl.$^7$ ............ A01N 43/16; A01N 43/08; A61K 31/35; A61K 31/34; C07D 309/30
(52) U.S. Cl. ............ 504/292; 504/299; 514/459; 514/460; 514/471; 514/473; 549/291; 549/318; 549/417
(58) Field of Search ............ 549/291, 318, 549/417; 514/459, 460, 471, 473; 504/292, 299

(56) References Cited

U.S. PATENT DOCUMENTS

| 4,925,868 | 5/1990 | Terao et al. ............ 514/425 |
| 5,045,560 | 9/1991 | Fischer et al. ............ 514/425 |
| 5,091,537 | 2/1992 | Fischer et al. ............ 546/226 |
| 5,094,681 | 3/1992 | Krämer et al. ............ 71/88 |
| 5,116,836 | 5/1992 | Fischer et al. ............ 514/224.2 |
| 5,142,065 | 8/1992 | Fischer et al. ............ 548/533 |
| 5,186,737 | 2/1993 | Fischer et al. ............ 504/283 |
| 5,207,817 | 5/1993 | Krämer et al. ............ 504/299 |
| 5,225,434 | 7/1993 | Bertram et al. ............ 514/411 |

(List continued on next page.)

FOREIGN PATENT DOCUMENTS

| 2187015 | 10/1995 | (CA) . |
| 196 02 524 | 1/1997 | (DE) . |
| 196 03 332 | 1/1997 | (DE) . |
| 442077 | 11/1995 | (EP) . |
| 95/01358 | 1/1995 | (WO) . |
| WO 95/03303 | 2/1995 | (WO) . |
| 95/20572 | 8/1995 | (WO) . |
| 95/26345 | 10/1995 | (WO) . |

OTHER PUBLICATIONS

S. Suzuki et al, Chem. Pharm. Bull, 15, 1120, 1967.
R. Schmierer & H. Mildenberger, Liebigs Ann. Chem., 1095, 1985.
J. Chem. Soc. Perkin Trans. I, 1567–76, 1985.
A.M. Chirazi, T. Kappe & E. Ziegler, Arch. Pharm. 309, 558, 1976.
E. Ziegler & E. Steiner, Monatsh. 95, 147, 1964.
R. Ketcham, T. Kappe & E. Ziegler, J. Heterocycl. Chem. 10, 223, Apr. 1973.

Primary Examiner—Deborah C. Lambkin
(74) Attorney, Agent, or Firm—Joseph C. Gil; Raymond J. Harmuth

(57) ABSTRACT

The present invention relates to novel compounds of the formula (I)

in which

Het represents one of the groups in which

A, B, D, G, V, W, X, Y and Z are as defined in the description, processes and intermediates for their preparation, and to their use as pesticides and herbicides.

7 Claims, No Drawings

U.S. PATENT DOCUMENTS

| | | | |
|---|---|---|---|
| 5,258,527 | 11/1993 | Krauskopf et al. | 548/543 |
| 5,262,383 | 11/1993 | Fischer et al. | 504/195 |
| 5,393,729 | 2/1995 | Fischer et al. | 504/128 |
| 5,420,155 | 5/1995 | Kulagowski et al. | 514/425 |
| 5,462,913 | 10/1995 | Fischer et al. | 504/138 |
| 5,504,057 | 4/1996 | Fischer et al. | 504/283 |
| 5,565,450 | 10/1996 | Fischer et al. | 514/227.2 |
| 5,567,671 | 10/1996 | Fischer et al. | 504/283 |
| 5,589,469 | 12/1996 | Fischer et al. | 514/91 |
| 5,602,078 | 2/1997 | Fischer et al. | 504/283 |
| 5,610,122 | 3/1997 | Fischer et al. | 504/251 |
| 5,616,536 | 4/1997 | Fischer et al. | 504/225 |
| 5,622,917 | 4/1997 | Fischer et al. | 504/283 |
| 5,677,449 | 10/1997 | Fischer et al. | 544/165 |
| 5,683,965 | 11/1997 | Bachmann et al. | 504/238 |
| 5,719,310 | 2/1998 | Fischer et al. | 560/83 |

SUBSTITUTED PHENYL KETO ENOLS AS PESTICIDES AND HERBICIDES

This is a divisional application of Ser. No. 09/155,637, filed Sep. 29, 1998, now U.S. Pat. No. 6,140,353, which is a 371 of PCT/EP97/01426 Mar. 21, 1997.

The invention relates to novel phenyl-substituted cyclic ketoenols, a plurality of processes and intermediates for their preparation and their use as pesticides and herbicides.

It has already been disclosed that certain phenyl-substituted cyclic ketoenols are active as insecticides, acaricides and/or herbicides.

Pharmaceutical properties of 3-acyl-pyrrolidine-2,4-diones have previously been described (S. Suzuki et al. Chem. Pharm. Bull. 15 1120 (1967)). Furthermore, N-phenylpyrrolidine-2,4-diones have been synthesized by R. Schmierer and H. Mildenberger (Liebigs Ann. Chem. 1985, 1095). Biological activity has not been disclosed for these compounds.

EP-A-0 262 399 and GB-A-2 266 888 disclose compounds (3-aryl-pyrrolidine-2,4-diones) of a similar structure, for which, however, no herbicidal, insecticidal or acaricidal activity has been disclosed. Unsubstituted, bicyclic 3-aryl-pyrrolidine-2,4-dione derivatives (EP-A-355 599 and EP-A 15 211) and substituted monocyclic 3-aryl-pyrrolidine-2,4-dione derivatives (EP-A-377 893 and EP-A-442 077) with herbicidal, insecticidal or acaricidal activity are known.

Polycyclic 3-arylpyrrolidine-2,4-dione derivatives (EP-A-442 073) and 1H-aryl-pyrrolidine-dione derivatives (EP-A-456 063, EP-A-521 334, EP-A-596 298, EP-A-613 884, EP-A-613 885, DE 44 40 594, WO 94/01 997, WO 95/01 358, WO 95/20 572, EP-A-668 267 and WO 95/26 954) are also known.

It is known that certain substituted $\Delta^3$-dihydrofuran-2-one derivatives have herbicidal properties (cf. DE-A-4 014 420). The synthesis of the tetronic acid derivatives used as starting materials (such as, for example, 3-(2-methyl-phenyl)-4-hydroxy-5-(4-fluorophenyl)-$\Delta^3$-dihydrofuran-2-one) is likewise described in DE-A-4 014 420. Compounds of similar structure without details of an insecticidal and/or acaricidal activity are known from the publication Campbell et al., J. Chem. Soc., Perkin Trans. 1, 1985, (8) 1567–76. Furthermore, 3-aryl-$\Delta^3$-dihydrofuranone derivatives having herbicidal, acaricidal and insecticidal properties are disclosed in EP-A-528 156 and EP-A-0 647 637. 3-Aryl-$\Delta^3$-dihydrothiophen-one derivatives are known (WO 95/26 345).

Certain phenyl-pyrone derivatives unsubstituted in the phenyl ring have already been disclosed (cf. A. M. Chirazi, T. Kappe and E. Ziegler, Arch. Pharm. 309, 558 (1976) and K.-H. Boltze and K. Heidenbluth, Chem. Ber. 91, 2849), a possible utility for these compounds as pesticides not being indicated. Phenyl-pyrone derivatives substituted in the phenyl ring and having herbicidal, acaricidal and insecticidal properties are described in EP-A-588 137.

Certain 5-phenyl-1,3-thiazine derivatives unsubstituted in the phenyl ring have already been described (cf. E. Ziegler and E. Steiner, Monatsh. 95, 147 (1964), R. Ketcham, T. Kappe and E. Ziegler, J. Heterocycl. Chem. 10, 223 (1973)), a possible utility as pesticides not being indicated for these compounds. 5-Phenyl-1,3-thiazine derivatives substituted in the phenyl ring and having herbicidal, acaricidal and insecticidal activity are described in WO 94/14 785.

However, the acaricidal and insecticidal activity and/or spectrum of action, and/or the toleration of these compounds by plants, in particular by crops, is not always satisfactory.

There have now been found a novel compounds of the formula (I)

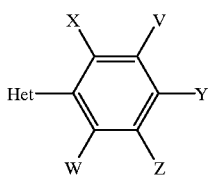

(I)

in which

V represents hydrogen, halogen, alkyl or alkoxy,

W represents cyano, nitro, halogen, alkyl, alkenyl, alkinyl, alkoxy, halogenoalkyl, halogenoalkoxy, respectively optionally substituted phenyl, phenoxy, phenylthio, phenylalkoxy or phenylalkylthio, X represents hydrogen, halogen, alkyl, alkenyl, alkinyl, alkoxy, halogenoalkyl, halogenoalkoxy, cyano, nitro or respectively optionally substituted phenyl, phenoxy, phenylthio, phenylalkyloxy or phenylalkylthio, Y represents hydrogen, halogen, alkyl, alkoxy, halogenoalkyl, halogenoalkoxy, cyano or nitro, Z represents halogen, alkyl, alkoxy, halogenoalkyl, halogenoalkoxy, hydroxyl, cyano, nitro or respectively optionally substituted phenoxy, phenylthio, 5- to 6-membered hetaryloxy, 5- to 6-membered hetarylthio, phenylalkyloxy or phenylalkylthio, or Y and Z represent together with the carbon atoms that they are attached to an optionally substituted cycle which is optionally interrupted by one or more hetero atoms, V, X and W having one of the abovementioned meanings, or W and Z represent together with the carbon atoms that they are attached to an optionally substituted cycle which is optionally interrupted by one or more heteroatoms, V, X and Y having one of the abovementioned meanings, Het represents one of the groups

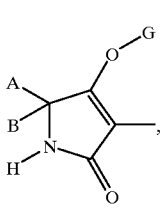

(1)

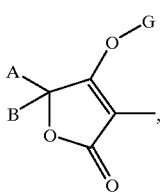

(2)

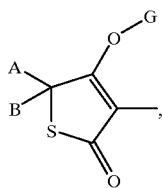
(3)

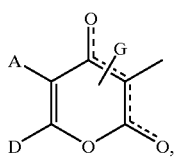
(4)

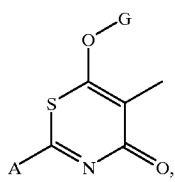
(5)

in which

A represents hydrogen, respectively optionally halogen-substituted alkyl, alkenyl, alkoxyalkyl, polyalkoxyalkyl or alkylthioalkyl, respectively saturated or unsaturated and optionally substituted cycloalkyl or heterocyclyl or respectively optionally halogen-, alkyl-, halogenoalkyl-, alkoxy-, halogenoalkoxy-, cyano- or nitro- substituted aryl, arylalkyl or hetaryl, B represents hydrogen, alkyl or alkoxyalkyl, or A and B represent together with the carbon atom that they are attached to a saturated or unsaturated optionally substituted carbocycle or heterocycle, D represents hydrogen or an optionally substituted radical from the group consisting of alkyl, alkenyl, alkinyl, alkoxyalkyl, polyalkoxyalkyl, alkylthioalkyl, saturated or unsaturated cycloalkyl, saturated or unsaturated heterocyclyl, arylalkyl, aryl, hetarylalkyl or hetaryl, or A and D represent together with the atoms that they are attached to a respectively optionally substituted carbocycle or heterocycle, G represents hydrogen (a) or one of the groups

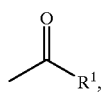
(b)

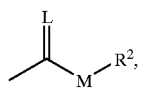
(c)

(d)

(e)

E or
(f)

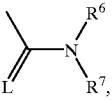
(g)

in which,

E represents a metal ion equivalent or an ammonium ion,

L represents oxygen or sulphur,

M represents oxygen or sulphur, $R^1$ represents respectively optionally halogen-substituted alkyl, alkenyl, alkoxyalkyl, alkylthioalkyl or polyalkoxyalkyl or respectively optionally halogen-, alkyl- or alkoxy- substituted cycloalkyl or heterocyclyl or respectively optionally substituted phenyl, phenylalkyl, hetaryl, phenoxyalkyl or hetaryloxyalkyl, $R^2$ represents respectively optionally halogen-substituted alkyl, alkenyl, alkoxyalkyl or polyalkoxyalkyl or respectively optionally substituted cycloalkyl, phenyl or benzyl, $R^3$, $R^4$ and $R^5$ each represent independently of one another respectively optionally halogen-substituted alkyl, alkoxy, alkylamino, dialkylamino, alkylthio, alkenylthio or cycloalkylthio or respectively optionally substituted phenyl, benzyl, phenoxy or phenylthio, $R^6$ and $R^7$ each represent independently of one another hydrogen, respectively optionally halogen-substituted alkyl, cycloalkyl, alkenyl, alkoxy or alkoxyalkyl or respectively optionally substituted phenyl or benzyl, or represent together with the N-atom that they are attached to an optionally oxygen- or sulphur- containing and optionally substituted cycle, excluding the following compounds

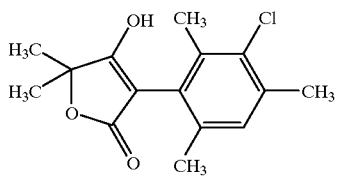

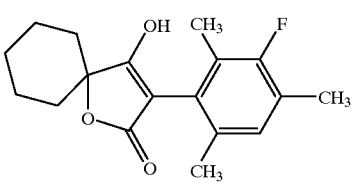

-continued

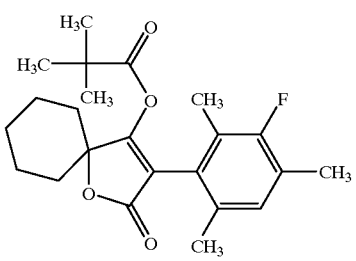

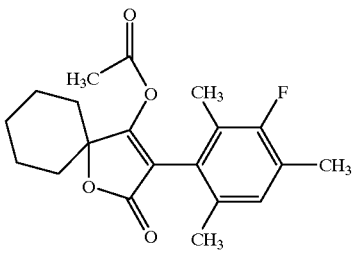

The compounds of the formula (I) can also be present, depending on the nature of the substituents, as geometric and/or optical isomers or isomer mixtures of differing composition which, if appropriate, can be separated in a customary manner. Both the pure isomers and the isomer mixtures, their preparation and use, and compositions containing them are part of the subject matter of the present invention. In the following, for simplicity, however, compounds of the formula (I) are always referred to, although both pure compounds and, if appropriate, mixtures having different proportions of isomer compounds are intended.

Including the meanings (1) to (5) of the group Het, the following principal structures (I-1) to (I-5) result:

(I-1)
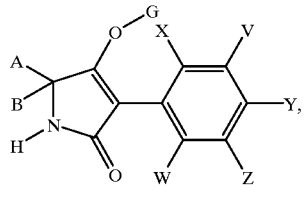

(I-2)
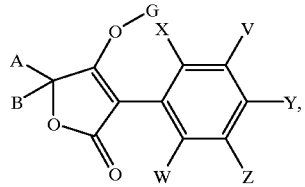

(I-3)
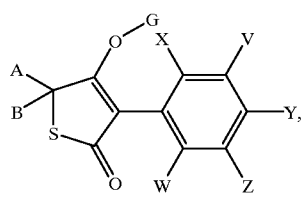

-continued (I-4)
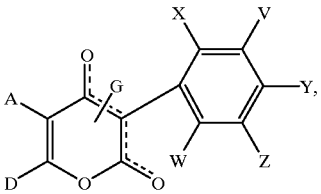

(I-5)
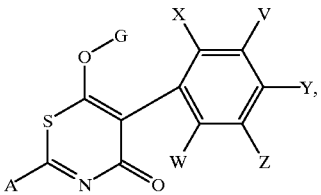

in which

A, B, D, G, V, W, X, Y and Z are each as defined above.

Including the various meanings (a), (b), (c), (d), (e), (f) and (g) of the group G, the following principal structures (I-1-a) to (I-1-g) result if Het represents the group (I)

(I-1-a):
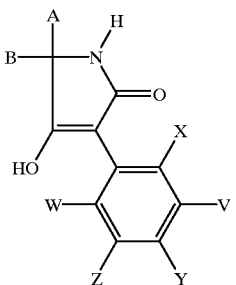

(I-1-b):
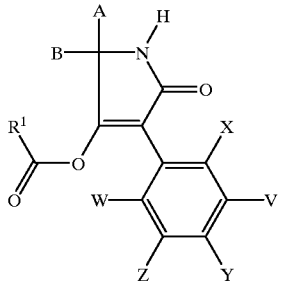

(I-1-c):
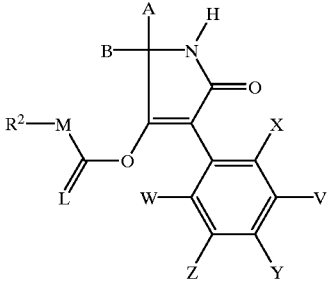

-continued
(I-1-d):
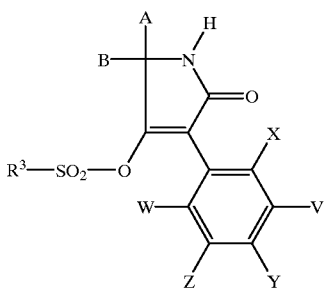
(I-1-e):
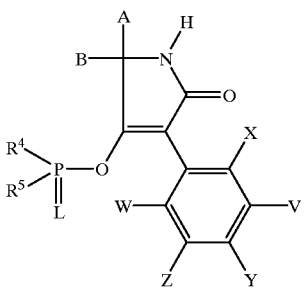
(I-1-f):
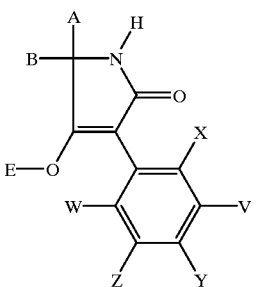
(I-1-g):
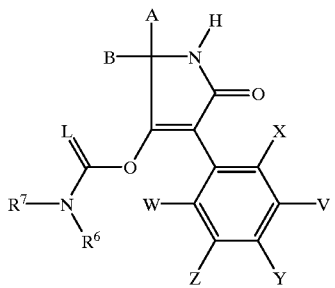
in which
A, B, E, L, M, V, W, X, Y, Z, $R^1$, $R^2$, $R^3$, $R^4$, $R^5$, $R^6$ and $R^7$ are each as defined above.
Including the various meanings (a), (b), (c), (d), (e), (f) and (g) of the group G, the following principal structures (I-2-a) to (I-2-g) result if Het represents the group (2)
(I-2-a):
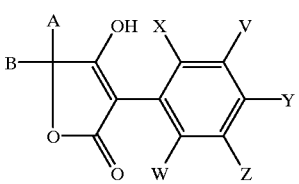
(I-2-b):
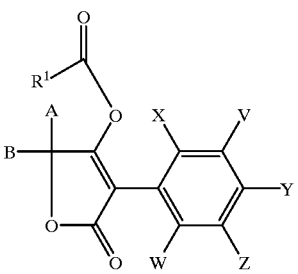
(I-2-c):
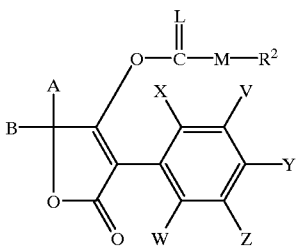
(I-2-d):
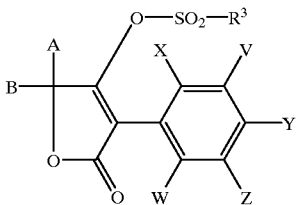
(I-2-e):
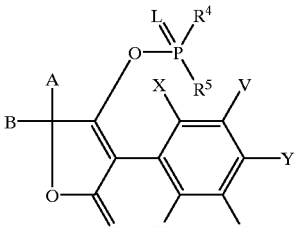
(I-2-f):
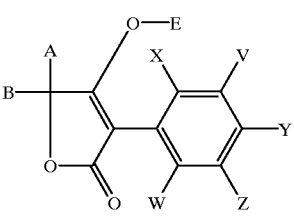
(I-2-g):
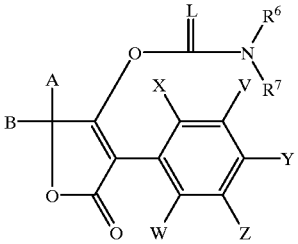
in which
A, B, E, L, M, V, W, X, Y Z, $R^1$, $R^2$, $R^3$, $R^4$, $R^5$, $R^6$ and $R^7$ are each as defined above.

Including the various meanings (a), (b), (c), (d), (e), (f) and (g) of the group G, the following principal structures (I-3-a) to (I-3-g) result if Het represents the group (3)

(I-3-a):
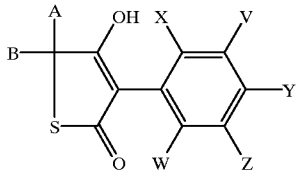

(I-3-b):
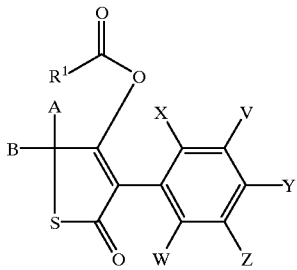

(I-3-c):
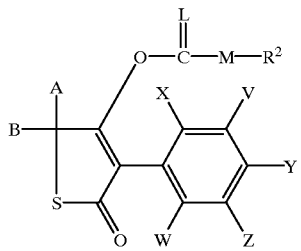

(I-3-d):
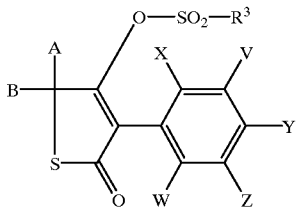

(I-3-e):
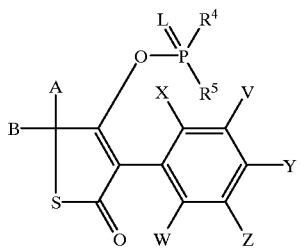

(I-3-f):
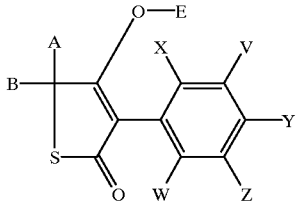

-continued (I-3-g):
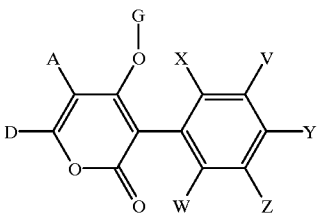

in which

A, B, E, L, M, V, W, X, Y, Z, $R^1$, $R^2$, $R^3$, $R^4$, $R^5$, $R^6$ and $R^7$ are each as defined above.

Depending on the position of the substituent G, the compounds of the formula (I-4) can be present in the two isomeric forms of formulae (I-4)$_a$ and (I-4)$_b$

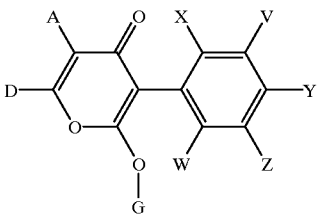

which is intended to be expressed by the dashed line in the formula (I-4).

The compounds of the formulae (I-4)$_a$ and (I-4)$_b$ can be present both as mixtures and in the form of their pure isomers. Mixtures of the compounds of the formulae (I-4)$_a$ and (I-4)$_b$ can, if desired, be separated by physical methods in a manner known per se, for example by chromatographic methods.

For better clarity, in the following in each case only one of the possible isomers is shown. This does not exclude the possibility that the compounds can optionally be present in the form of the isomer mixtures or in the other respective isomer form.

Including the various meanings (a), (b), (c), (d), (e), (f) and (g) of the group G, the following principal structures (I-4-a) to (I-4-g) result if Het represents the group (4)

(I-4-a):
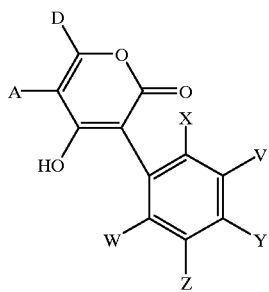
(I-4-b):
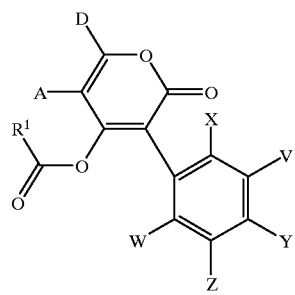
(I-4-c):
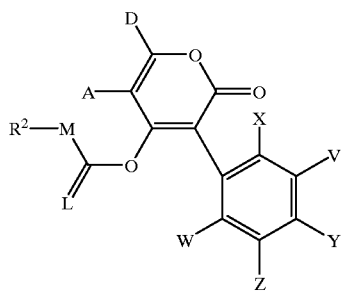
(I-4-d):
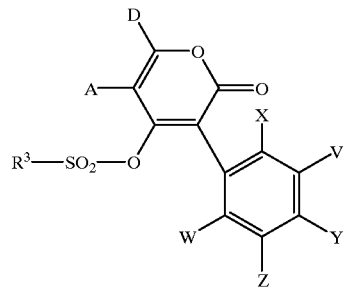
(I-4-e):
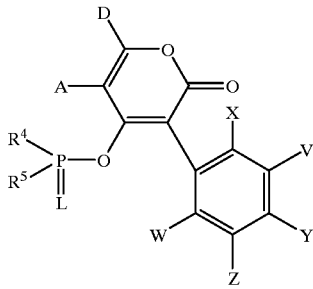
(I-4-f):
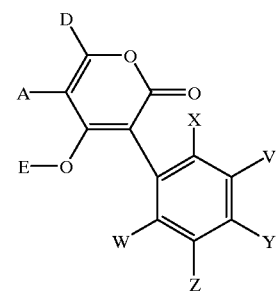
(I-4-g):
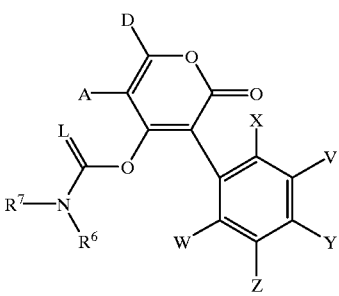
in which
A, D, E, L, M, V, W, X, Y, Z, $R^1$, $R^2$, $R^3$, $R^4$, $R^5$, $R^6$ and $R^7$ are each as defined above.
Including the various meanings (a), (b), (c), (d), (e), (f) and (g) of the group G. the following principal structures (I-5-a) to (I-5-g) result if Het represents the group (5)
(I-5-a):
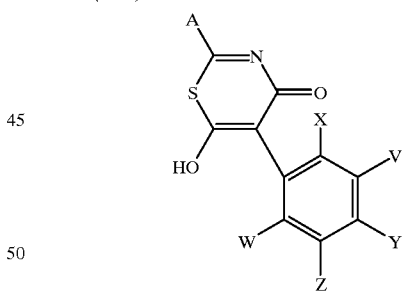
(I-5-b):
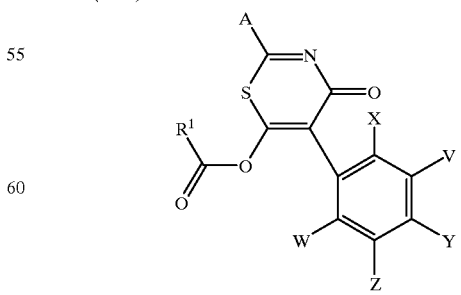

-continued (I-5-c):

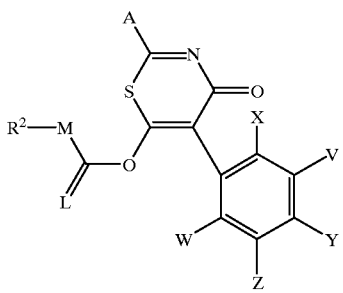

(I-5-d):

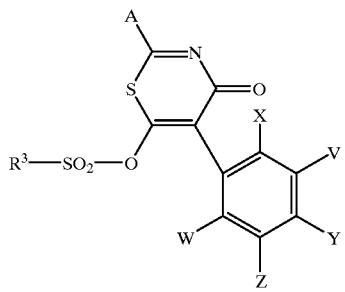

(I-5-e):

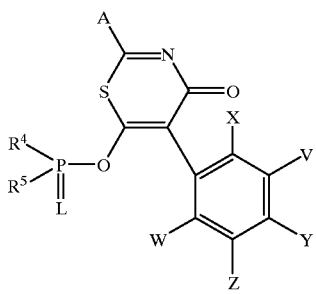

(I-5-f):

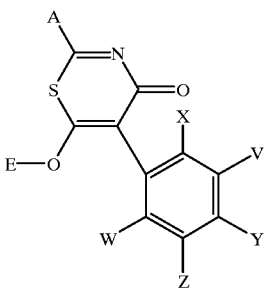

(I-5-g):

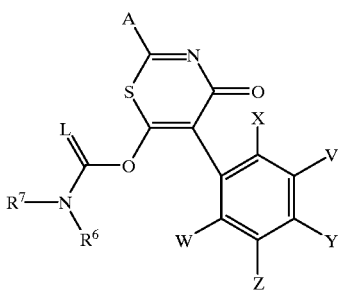

in which

A, E, L, M, V, W, X, Y, Z, $R^1$, $R^2$, $R^3$, $R^4$, $R^5$, $R^6$ and $R^7$ are each as defined above.

Furthermore, it has been found that the novel compounds of the formula (I) are obtained by one of the processes described below:

(A) Compounds of the formula (I-1-a)

(I-1-a)

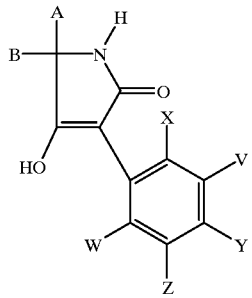

in which
A, B, V, W, X, Y and Z are each as defined above, are obtained by the intramolecular condensation of compounds of the formula (II)

(II)

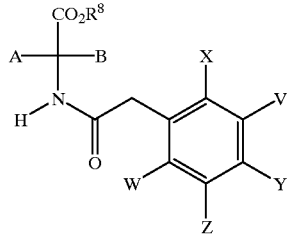

in which,
A, B, V, W, X, Y and Z are each as defined above and $R^8$ represents alkyl (preferably $C_1$–$C_6$-alkyl)
in the presence of a diluent and in the presence of a base.

(B) Furthermore, it was found that compounds of the formula (I-2-a)

(I-2-a)

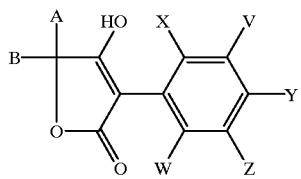

in which
A, B, V, W, X, Y and Z are each as defined above
are obtained by the intramolecular condensation of compounds of the formula (III)

(III)

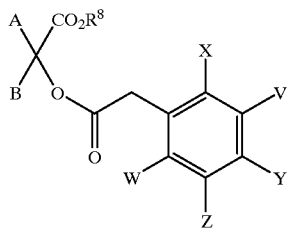

in which
A, B, V, W, X, Y, Z and $R^8$ are each as defined above
in the presence of a diluent and in the presence of a base.

(C) Furthermore, it was found that compounds of the formula (I-3-a)

(I-3-a)

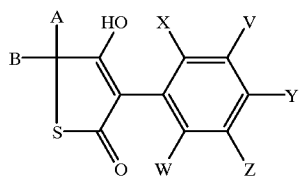

in which
A, B, V, W, X, Y and Z are each as defined above
are obtained by the intramolecular cyclization of compounds of formula (IV)

(IV)

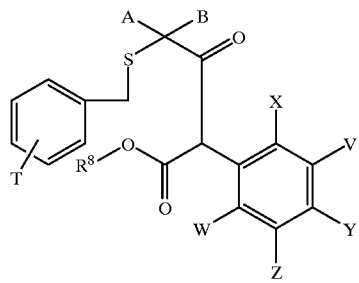

in which
A, B, V, W, X, Y, Z and $R^8$ are each as defined above and
T represents hydrogen, halogen, alkyl (preferably $C_1$–$C_6$-alkyl) or alkoxy (preferably $C_1$–$C_8$-alkoxy),
if appropriate in the presence of a diluent and in the presence of an acid.

(D) Furthermore, it was found that compounds of the formula (I-4-a)

(I-4-a)

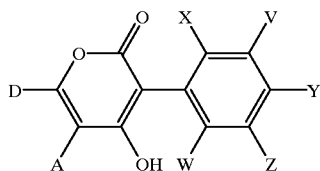

in which
A, D, V, W, X, Y and Z are each as defined above
are obtained by reacting compounds of the formula (V)

(V)

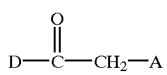

in which
A and D are each as defined above
or their silyl enol ethers of the formula (Va)

(Va)

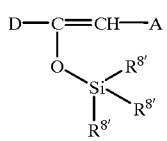

in which
A and D are each as defined above and
$R^{8'}$ represents alkyl (preferably methyl)
with compounds of the formula (VI)

(VI)

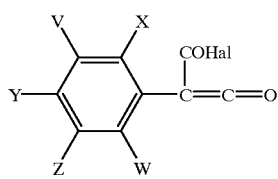

in which
V, W, X, Y and Z are each as defined above and
Hal represents halogen (preferably chlorine or bromine),
if appropriate in the presence of a diluent and if appropriate in the presence of an acid acceptor.

(E) Furthermore, it was found that compounds of the formula (I-5-a)

(I-5-a)

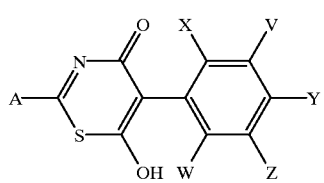

in which
A, V, W, X, Y and Z are each as defined above
are obtained by reacting compounds of the formula (VII)

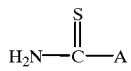
(VII)

in which
A is as defined above
with compounds of the formula (VI)

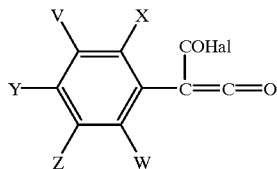
(VI)

in which
Hal, V, W, X, Y and Z are each as defined above,
if appropriate in the presence of a diluent and if appropriate in the presence of an acid acceptor.

In addition, it has been found (F) that the compounds of the formulae (I-1-b) to (I-5-b) shown above in which A, B, D, R$^1$, V, W, X, Y and Z are each as defined above are obtained by reacting compounds of the formulae (I-1-a) to (I-5-a) shown above in which A, B, D, V, W, X, Y and Z are each as defined above α) with acid halides of the formula (VIII)

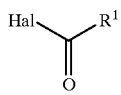
(VIII)

in which
R$^1$ is as defined above and
Hal represents halogen (in particular chlorine or bromine)

or

β) with carboxylic anhydrides of the formula (IX)

$R^1\text{—CO—O—CO—}R^1$ (IX)

in which
R$^1$ is as defined above,
if appropriate in the presence of a diluent and if appropriate in the presence of an acid-binding agent;

(G) that the compounds of the formulae (I-1-c) to (I-5-c) shown above in which A, B, D, R$^2$, V, W, M, X, Y and Z are each as defined above and L represents oxygen are obtained by reacting compounds of the formulae (I-1-a) to (I-5-a) shown above in which A, B, D, V, W, X, Y and Z are each as defined above in each case
with chloroformic esters or chloroformic thioesters of the formula (X)

$R^2\text{—M—CO—Cl}$ (X)

in which
R$^2$ and M are each as defined above,
if appropriate in the presence of a diluent and if appropriate in the presence of an acid-binding agent;

(H) that compounds of the formulae (I-1-c) to (I-5-c) shown above in which A, B, D, R$^2$, V, W, M, X, Y and Z are each as defined above and L represents sulphur are obtained by reacting compounds of the formulae (I-1-a) to (I-5-a) shown above in which A, B, D, V, W, X, Y and Z are each as defined above in each case α) with chloromonothioformic esters or chlorodithioformic esters of the formula (XI)

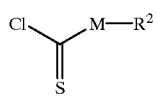
(XI)

in which
M and R$^2$ are each as defined above,
if appropriate in the presence of a diluent and if appropriate in the presence of an acid-binding agent or β) with carbon disulphide and subsequently with compounds of the formula (XII)

$R^2\text{—Hal}$ (XII)

in which
R$^2$ is as defined above and
Hal represents chlorine, bromine or iodine,
if appropriate in the presence of a diluent and if appropriate in the presence of a base, (I) that compounds of the formulae (I-1-d) to (I-5-d) shown above in which A, B, D, R$^3$, V, W, X, Y and Z are each as defined above are obtained by reacting compounds of the formulae (I-1-a) to (I-5-a) shown above in which A, B, D, V, W, X, Y and Z are each as defined above in each case
with sulphonyl chlorides of the formula (XIII)

$R^3\text{—S}_2\text{—Cl}$ (XII)

in which
R$^3$ is as defined above,
if appropriate in the presence of a diluent and if appropriate in the presence of an acid-binding agent, (J) that compounds of the formulae (I-1-e) to (I-5-e) shown above in which A, B, D, L, R$^4$, R$^5$, V, W, X, Y and Z are each as defined above are obtained by reacting compounds of the formulae (I-1-a) to (I-4-a) shown above in which A, B, D, V, W, X, Y and Z are each as defined above in each case with phosphorus compounds of the formula (XIV)

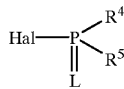
(XIV)

in which

L, $R^4$ and $R^5$ are each as defined above and

Hal represents halogen (in particular chlorine or bromine), if appropriate in the presence of a diluent and if appropriate in the presence of acid-binding agent, (K) that compounds of the formulae (I-1-f) to (I-5-f) shown above in which A, B, D, E, V, W, X, Y and Z are each as defined above are obtained by reacting compounds of the formulae (I-1-a) to (I-5-a) in which A, B, D, V, W, X, Y and Z are each as defined above in each case with metal compounds or amines of the formulae (XV) or (XVI)

$$Me(OR^{10})_t \qquad (XV)$$

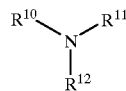
(XVI)

in which

Me represents a mono- or divalent metal (preferably an alkali metal or an alkaline earth metal such as lithium, sodium, potassium, magnesium or calcium), t represents the number 1 or 2 and $R^{10}$, $R^{11}$, $R^{12}$ each represent independently of one another hydrogen or alkyl (preferably $C_1$–$C_8$-alkyl), if appropriate in the presence of a diluent, (L) that compounds of the formulae (I-1g) to (I-5-g) shown above, in which A, B, D, L, $R^6$, $R^7$, V, W, X, Y and Z are each as defined above, are obtained by reacting compounds of the formulae (I-1-a) to (I-5-a) shown above, in which A, B, D, V, W, X, Y and Z are each as defined above, in each case α) with isocyanates or isothiocyanates of the formula (XVII)

$$R^6\text{—}N\text{=}C\text{=}L \qquad (XVII)$$

in which $R^6$ and L are each as defined above, if appropriate in the presence of a diluent and if appropriate in the presence of a catalyst or α) with carbamoyl chlorides or thiocarbamoyl chlorides of the formula (XVIII)

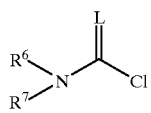
(XVIII)

in which

L, $R^6$ and $R^7$ are each as defined above, if appropriate in the presence of a diluent and if appropriate in the presence of an acid-binding agent.

Furthermore, it has surprisingly been found that the novel compounds of the formula (I) have very good activity as pesticides, preferably as insecticides, acaricides and, as herbicides, and that they additionally are very well tolerated by plants, in particular by crops.

Formula (I) provides a general definition of the compounds according to the invention. Preferred substituents or ranges of the radicals shown in the formulae mentioned hereinabove and hereinbelow are illustrated below:

V preferably represents hydrogen, halogen, $C_1$–$C_6$-alkyl or $C_1$–$C_6$-alkoxy.

W preferably represents cyano, nitro, halogen, $C_1$–$C_6$-alkyl, $C_2$–$C_6$-alkenyl, $C_2$–$C_6$-alkinyl, $C_1$–$C_6$-alkoxy, $C_1$–$C_4$-halogenoalkyl, $C_1$–$C_4$-halogenoalkoxy or respectively optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenoxy, phenylthio, phenyl-$C_1$–$C_4$-alkoxy or phenyl-$C_1$–$C_4$-alkylthio, X preferably represents hydrogen, halogen, $C_1$–$C_6$-alkyl, $C_2$–$C_6$-alkenyl, $C_2$–$C_6$-alkinyl, $C_1$–$C_6$-alkoxy, $C_1$–$C_4$-halogenoalkyl, $C_1$–$C_4$-halogenoalkoxy, cyano, nitro or respectively optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano- substituted phenyl, phenoxy, phenylthio, phenyl-$C_1$–$C_4$-alkoxy or phenyl-$C_1$–$C_4$-alkylthio, Y preferably represents hydrogen, halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, Z preferably represents halogen, $C_1$–$C_6$-alkyl, $C_1$–$C_6$-alkoxy, $C_1$–$C_4$-halogenoalkyl, $C_1$–$C_4$-halogenoalkoxy, hydroxyl, cyano, nitro or respectively optionally halogen-, $C_1$–$C_4$-alkyl-, $C_1$–$C_4$-alkoxy-, $C_1$–$C_4$-halogenoalkyl-, $C_1$–$C_4$-halogenoalkoxy-, nitro- or cyano-substituted phenoxy, phenylthio, thiazolyloxy, pyridinyloxy, pyrimidyloxy, pyrazolyloxy, phenyl-$C_1$–$C_4$-alkyloxy or phenyl-$C_1$–$C$-alkylthio, or, Y and Z together preferably represent respectively optionally halogen-, $C_1$–$C_6$-alkyl-, $C_1$–$C_6$-alkoxy- or $C_1$–$C_4$-halogenoalkyl-substituted $C_3$–$C_5$-alkanediyl or $C_3$–$C_5$-alkenediyl in which one to three members can be optionally replaced independently of one another by oxygen, sulphur, nitrogen or a carbonyl group, or W and Z together preferably represent respectively optionally halogen-, $C_1$–$C_6$-alkyl-, $C_1$–$C_6$-alkoxy- or $C_1$–$C_4$-halogenoalkyl-substituted $C_3$–$C_5$-alkanediyl or $C_3$–$C_5$-alkenediyl in which one to three members can be optionally replaced independently of one another by oxygen, sulphur, nitrogen or a carbonyl group.

Het preferably represents one of the groups (1)
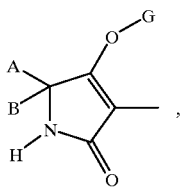

(2)
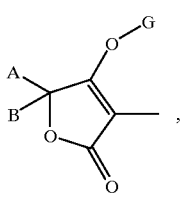

(3)
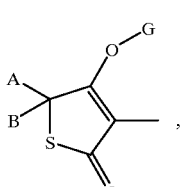

(4)
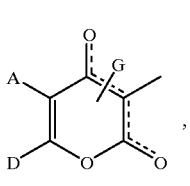

(5)
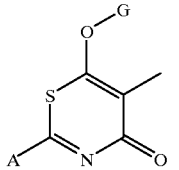

A preferably represents hydrogen, respectively optionally halogen-substituted $C_1$–$C_{12}$-alkyl, $C_2$–$C_8$-alkenyl, $C_1$–$C_{10}$-alkoxy-$C_1$–$C_8$-alkyl, poly-$C_1$–$C_8$-alkoxy-$C_1$–$C_8$-alkyl or $C_1$–$C_{10}$-alkylthio-$C_1$–$C_6$-alkyl, optionally halogen-, $C_1$–$C_6$-alkyl- or $C_1$–$C_6$-alkoxy-substituted $C_3$–$C_8$-cycloalkyl in which optionally one or two not directly adjacent methylene groups are replaced by oxygen and/or sulphur, or preferably represents respectively optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano- or nitro-substituted phenyl, naphthyl, phenyl-$C_1$–$C_6$-alkyl, naphthyl-$C_1$–$C_6$-alkyl or hetaryl having 5 or 6 ring atoms and one to three heteroatoms from the group consisting of oxygen, sulphur and nitrogen.

B preferably represents hydrogen, $C_1$–$C_{12}$-alkyl or $C_1$–$C_8$-alkoxy-$C_1$–$C_6$-alkyl or A, B and the carbon atom that they are attached to preferably represent $C_3$–$C_{10}$-cycloalkyl or $C_5$–$C_{10}$-cycloalkenyl where in each case one methylene group is optionally replaced by oxygen or sulphur and which are optionally substituted by $C_1$–$C_8$-alkyl, $C_3$–$C_{10}$-cycloalkyl, $C_1$–$C_8$halogenoalkyl, $C_1$–$C_8$-alkoxy, $C_1$–$C_8$-alkylthio, halogen or phenyl, or A, B and the carbon atom that they are attached to preferably represent $C_5$–$C_6$-cycloalkyl which is substituted by an alkylenediyl group optionally containing one or two oxygen and/or sulphur atoms, or by an alkylenedioxy group or alkylenedithioyl group forming a further five- to eight-membered ring with the carbon atom that it is attached to, or A, B and the carbon atom that they are attached to preferably represent $C_3$–$C_8$-cycloalkyl or $C_5$–$C_8$-cycloalkenyl in which two carbon atoms are connected by respectively optionally $C_1$–$C_6$-alkyl-, $C_1$–$C_6$-alkoxy- or halogen-substituted $C_3$–$C_6$-alkanediyl, $C_3$–$C_6$-alkenediyl or $C_4$–$C_6$-alkanedienediyl where in each case one methylene group is optionally replaced by oxygen or sulphur.

D preferably represents hydrogen, respectively optionally halogen-substituted $C_1$–$C_{12}$-alkyl, $C_3$–$C_8$-alkenyl, $C_3$–$C_8$-alkinyl, $C_1$–$C_{10}$-alkoxy-$C_2$–$C_8$-alkyl, poly-$C_1$–$C_8$-alkoxy-$C_2$–$C_8$-alkyl or $C_1$–$C_{10}$-alkylthio-$C_2$–$C_8$-alkyl, optionally halogen-, $C_1$–$C_4$-alkyl-, $C_1$–$C_4$-alkoxy- or $C_1$–$C_4$-halogenoalkyl-substituted $C_3$–$C_8$-cycloalkyl in which optionally one or two not directly adjacent methylene groups are replaced by oxygen and/or sulphur, or preferably represents respectively optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano- or nitro-substituted phenyl, hetaryl having 5 to 6 ring atoms and one or two heteroatoms from the group consisting of oxygen, sulphur and nitrogen, phenyl-$C_1$–$C_6$-alkyl or hetaryl-$C_1$–$C_6$-alkyl having 5 to 6 ring atoms and one or two heteroatoms from the group consisting of oxygen, sulphur and nitrogen, or A and D together preferably represent a $C_3$–$C_6$-alkanediyl, $C_3$–$C_6$-alkenediyl or $C_4$–$C_6$-alkadienediyl group in which in each case one methylene group is optionally replaced by oxygen or sulphur and which are respectively optionally substituted by halogen or by respectively optionally halogen-substituted $C_1$–$C_{10}$-alkyl, $C_1$–$C_6$-alkoxy, $C_1$–$C_6$-alkylthio, $C_3$–$C_7$-cycloalkyl, phenyl or benzyloxy or by a further $C_3$–$C_6$-alkanediyl, $C_3$–$C_6$-alkenediyl or $C_4$–$C_6$-alkadienediyl group forming a fused-on ring where in each case one methylene group is optionally replaced by oxygen or sulphur and which are optionally substituted by $C_1$–$C_6$-alkyl, or A and D together represent a $C_3$–$C_6$-alkanediyl or $C_3$–$C_6$-alkenediyl group, each of which optionally contains one of the following groups

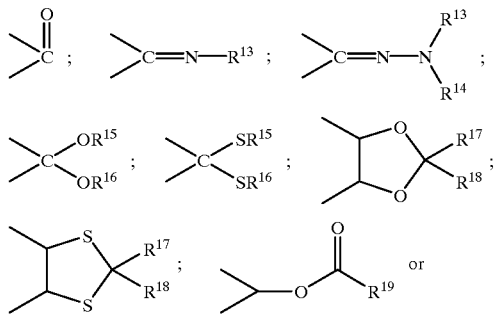

-continued

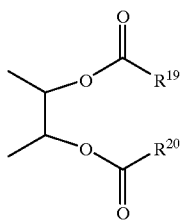

G preferably represents hydrogen (a) or one of the groups (b)

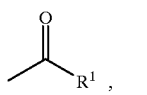

(c)

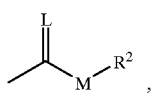

(d)

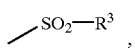

(e)

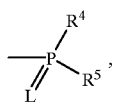

(f)

E or (g)

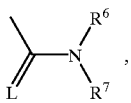

in which
E represents a metal ion equivalent or an ammonium ion,
L represents oxygen or sulphur and
M represents oxygen or sulphur.

$R^1$ preferably represents respectively optionally halogen-substituted $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or poly-$C_1$–$C_8$-alkoxy-$C_1$–$C_8$-alkyl or respectively halogen-, $C_1$–$C_6$-alkyl- or $C_1$–$C_6$-alkoxy-substituted $C_3$–$C_8$-cycloalkyl in which one or two not directly adjacent methylene groups are optionally replaced by oxygen and/or sulphur, optionally halogen-, cyano-, nitro-, $C_1$–$C_6$-alkyl-, $C_1$–$C_6$-alkoxy-, $C_1$–$C_6$-halogenoalkyl-, $C_1$–$C_6$-halogenoalkoxy-, $C_1$–$C_6$-alkylthio- or $C_1$–$C_6$-alkylsulphonyl-substituted phenyl, optionally halogen-, nitro-, cyano-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$–$C_6$-alkyl, optionally halogen- or $C_1$–$C_6$-alkyl-substituted 5- or 6-membered hetaryl having one or two heteroatoms from the group consisting of oxygen, sulphur and nitrogen, optionally halogen- or $C_1$–$C_6$-alkyl-substituted phenoxy-$C_1$–$C_6$-alkyl or optionally halogen-, amino- or $C_1$–$C_6$-alkyl-substituted 5- or 6-membered hetaryloxy-$C_1$–$C_6$-alkyl having one or two heteroatoms from the group consisting of oxygen, sulphur and nitrogen.

$R^2$ preferably represents respectively optionally halogen-substituted $C_1$–$C_{20}$-alkyl, $C_2$–$C_{20}$-alkenyl, $C_1$–$C_8$-alkoxy-$C_2$–$C_8$-alkyl or poly-$C_1$–$C_8$-alkoxy-$C_2$–$C_8$-alkyl, optionally halogen-, $C_1$–$C_6$-alkyl- or $C_1$–$C_6$-alkoxy-substituted $C_3$–$C_8$-cycloalkyl or respectively optionally halogen-, cyano-, nitro-, $C_1$–$C_6$-alkyl-, $C_1$–$C_6$-alkoxy-, $C_1$–$C_6$-halogenoalkyl or $C_1$–$C_6$-halogenoalkoxy-substituted phenyl or benzyl.

$R^3$ preferably represents optionally halogen-substituted $C_1$–$C_8$-alkyl or respectively optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, cyano- or nitro-substituted phenyl or benzyl.

$R^4$ and $R^5$ each preferably represent independently of one another respectively optionally halogen-substituted $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio or $C_3$–$C_8$-alkenylthio, respectively optionally halogen-, nitro-, cyano-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkyl- or $C_1$–$C_4$-halogeno-alkyl-substituted phenyl, phenoxy or phenylthio.

$R^6$ and $R^7$ preferably represent independently of one another hydrogen, respectively optionally halogen-substituted $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_2$–$C_8$-alkyl, respectively optionally halogen-, $C_1$–$C_8$-alkyl-, $C_1$–$C_8$-halogenoalkyl- or $C_1$–$C_8$-alkoxy-substituted phenyl or benzyl or together represent an optionally $C_1$–$C_6$-alkyl-substituted $C_3$–$C_6$-alkylene radical in which one methylene group is optionally replaced by oxygen or sulphur.

$R^{13}$ preferably represents hydrogen or respectively optionally halogen-substituted $C_1$–$C_8$-alkyl or $C_1$–$C_8$-alkoxy, optionally halogen-, $C_1$–$C_4$-alkyl- or $C_1$–$C_4$-alkoxy-substituted $C_3$–$C_8$-cycloalkyl in which one methylene group is optionally replaced by oxygen or sulphur, or respectively optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenyl-$C_1$–$C_4$-alkyl or phenyl-$C_1$–$C_4$-alkoxy.

$R^{14}$ preferably represents hydrogen or $C_1$–$C_8$-alkyl or $R^{13}$ and $R^{14}$ together preferably represent $C_4$–$C_6$-alkanediyl.

$R^{15}$ and $R^{16}$ are identical or different and preferably represent $C_1$–$C_6$-alkyl or $R^{15}$ and $R^{16}$ together preferably represent a $C_2$–$C_4$-alkanediyl radical which is optionally substituted by $C_1$–$C_6$-alkyl or by optionally halogen-, $C_1$–$C_4$-alkyl-, $C_1$–$C_4$-halogenoalkyl-, $C_1$–$C_4$-alkoxy-, $C_1$–$C_4$-halogenoalkoxy-, nitro- or cyano-substituted phenyl.

$R^{17}$ and $R^{18}$ each preferably represent independently of one another hydrogen, optionally halogen-substituted $C_1$–$C_8$-alkyl or optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl or $R^{17}$ and $R^{18}$ preferably represent together with the carbon atom that they are attached to optionally $C_1$–$C_4$-alkyl-substituted $C_5$–$C_7$-cycloalkyl in which one methylene group is optionally replaced by oxygen or sulphur.

$R^{19}$ and $R^{20}$ each preferably represent independently of one another $C_1$–$C_{10}$-alkyl, $C_1$–$C_{10}$-alkenyl, $C_1$–$C_{10}$- alkoxy, $C_1$–$C_{10}$-alkylamino, $C_3$–$C_{10}$-alkenylamino, di-($C_1$–$C_{10}$-alkyl)amino or di-($C_3$–$C_{10}$-alkenyl)amino).

V particularly preferably represents hydrogen, fluorine, chlorine, bromine, $C_1$–$C_4$-alkyl or $C_1$–$C_4$-alkoxy.

W particularly preferably represents cyano, nitro, fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy or respectively optionally fluorine-, chlorine-, bromine-, $C_1$–$C_4$-alkyl-, $C_1$–$C_4$-alkoxy-, $C_1$–$C_2$-halogenoalkyl-, $C_1$–$C_2$-halogenoalkoxy-, nitro- or cyano-substituted phenyl, phenoxy, benzyl or benzyloxy.

X particularly preferably represents hydrogen, fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano, nitro or respectively optionally fluorine-, chlorine-, bromine-, $C_1$–$C_4$-alkyl-, $C_1$–$C_4$-alkoxy-, $C_1$–$C_2$-halogenoalkyl-, $C_1$–$C_2$-halogenoalkoxy-, nitro- or cyano-substituted phenyl, phenoxy, benzyl or benzyloxy.

Y particularly preferably represents hydrogen, fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro.

Z particularly preferably represents fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, hydroxyl, cyano, nitro or respectively optionally fluorine-, chlorine-, bromine-, $C_1$–$C_4$-alkyl-, $C_1$–$C_4$-alkoxy-, $C_1$–$C_2$-halogenoalkyl-, $C_1$–$C_2$-halogenoalkoxy-, nitro- or cyano-substituted phenoxy or benzyloxy, or Y and Z together particularly preferably represent respectively optionally fluorine-, chlorine-, bromine-, $C_1$–$C_4$-alkyl-, $C_1$–$C_4$-alkoxy- or $C_1$–$C_2$-halogenoalkyl-substituted $C_3$–$C_4$-alkanediyl or $C_3$–$C_4$-alkenediyl in which optionally one or two not directly adjacent members are replaced independently of one another by oxygen, sulphur or nitrogen, or W and Z together particularly preferably represent respectively optionally fluorine-, chlorine-, bromine-, $C_1$–$C_4$-alkyl-, $C_1$–$C_4$-alkoxy- or $C_1$–$C_2$-halogenoalkyl-substituted $C_3$–$C_4$-alkanediyl or $C_3$–$C_4$-alkenyldiyl in which optionally one or two not directly adjacent members are replaced independently of one another by oxygen, sulphur or nitrogen.

Het particularly preferably represents one of the groups (1)

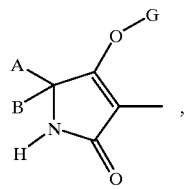

(2)

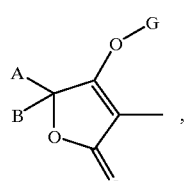

(3)

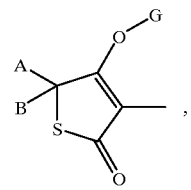

(4)

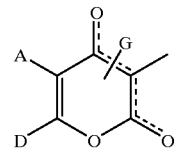

(5)

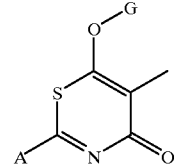

A particularly preferably represents hydrogen, respectively optionally fluorine- or chlorine-substituted $C_1$–$C_{10}$-alkyl, $C_2$–$C_6$-alkenyl, $C_1$–$C_8$-alkoxy-$C_1$–$C_6$-alkyl, poly-$C_1$–$C_6$-alkoxy-$C_1$–$C_6$-alkyl or $C_1$–$C_8$-alkylthio-$C_1$–$C_6$-alkyl or optionally fluorine-, chlorine-, $C_1$–$C_4$-alkyl- or $C_1$–$C_4$-alkoxy-substituted $C_3$–$C_7$-cycloalkyl in which one or two not directly adjacent methylene groups are optionally replaced by oxygen and/or sulphur, or respectively optionally fluorine-, chlorine-, bromine-, $C_1$–$C_4$-alkyl-, $C_1$–$C_4$-halogenoalkyl-, $C_1$–$C_4$-alkoxy-, $C_1$–$C_4$-halogenoalkoxy-, cyano- or nitro-substituted phenyl, furanyl, pyridyl, imidazolyl, triazolyl, pyrazolyl, indolyl, thiazolyl, thienyl or phenyl-$C_1$–$C_4$-alkyl.

B particularly preferably represents hydrogen, $C_1$–$C_{10}$-alkyl or $C_1$–$C_6$-alkoxy-$C_1$–$C_4$-alkyl or A, B and the carbon atom that they are attached to particularly preferably represent $C_3$–$C_8$-cycloalkyl or $C_5$–$C_8$-cycloalkenyl in which respectively optionally one methylene group is replaced by oxygen or sulphur and which are optionally substituted by $C_1$–$C_6$-alkyl, $C_3$–$C_8$-cycloalkyl, $C_1$–$C_3$-halogenoalkyl, $C_1$–$C_6$-alkoxy, $C_1$–$C_6$-alkylthio, fluorine, chlorine or phenyl, or A, B and the carbon atom that they are attached to particularly preferably represent $C_5$–$C_6$-cycloalkyl which is substituted by an alkylenediyl group optionally containing one or two oxygen or sulphur atoms, or by an alkylenedioxy or alkylenedithiol group forming a further five- to seven-membered ring with the carbon atom that it is attached to or A, B and the carbon atom that they are attached to particularly preferably represent $C_3$–$C_6$-cycloalkyl or $C_5$–$C_6$-cycloalkenyl in which two carbon atoms are connected by respectively optionally $C_1$–$C_4$-alkyl-, $C_1$–$C_4$-alkoxy-, fluorine-, chlorine- or bromine-substituted $C_3$–$C_5$-alkanediyl, $C_3$–$C_5$-alkenediyl or butadienediyl in which respectively optionally one methylene group is replaced by oxygen or sulphur.

D particularly preferably represents hydrogen, respectively optionally fluorine- or chlorine-substituted $C_1$–$C_{10}$-alkyl, $C_3$–$C_6$-alkenyl, $C_3$–$C_6$-alkinyl, $C_1$–$C_8$-alkoxy-$C_2$–$C_6$-alkyl, poly-$C_1$–$C_6$-alkoxy-$C_2$–$C_6$-alkyl or $C_1$–$C_8$-alkylthio-$C_2$–$C_6$-alkyl, optionally fluorine-, chlorine-, $C_1$–$C_4$-alkyl-, $C_1$–$C_4$-alkoxy- or $C_1$–$C_2$-halogenoalkyl-substituted $C_3$–$C_7$-cycloalkyl in which one or two not directly adjacent methylene groups are optionally replaced by oxygen and/or sulphur, or particularly preferably represents respectively optionally fluorine-, chlorine-, bromine-, $C_1$–$C_4$-alkyl-, $C_1$–$C_4$-halogenoalkyl-, $C_1$–$C_4$-alkoxy-, $C_1$–$C_4$-halogenoalkoxy-, cyano- or nitro-substituted phenyl, furanyl, imidazolyl, pyridyl, thiazolyl, pyrazolyl, pyrimidyl, pyrrolyl, thienyl, triazolyl or phenyl-$C_1$–$C_4$-alkyl or A and D together particularly preferably represent a $C_3$–$C_5$-alkanediyl or $C_3$–$C_5$-alkenediyl group in which respectively optionally one carbon atom is replaced by oxygen or sulphur and which are optionally substituted by fluorine, chlorine or respectively optionally fluorine- or chlorine-substituted $C_1$–$C_6$-alkyl, $C_1$–$C_4$-alkoxy, $C_1$–$C_4$-alkylthio, $C_3$–$C_6$-cycloalkyl, phenyl or benzyloxy or which respectively optionally contain one of the following groups:

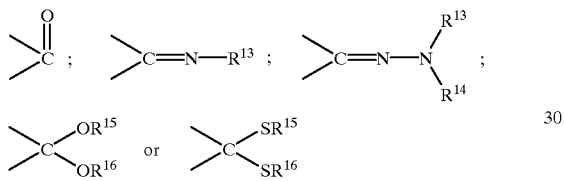

G particularly preferably represents hydrogen (a) or one of the groups (b)

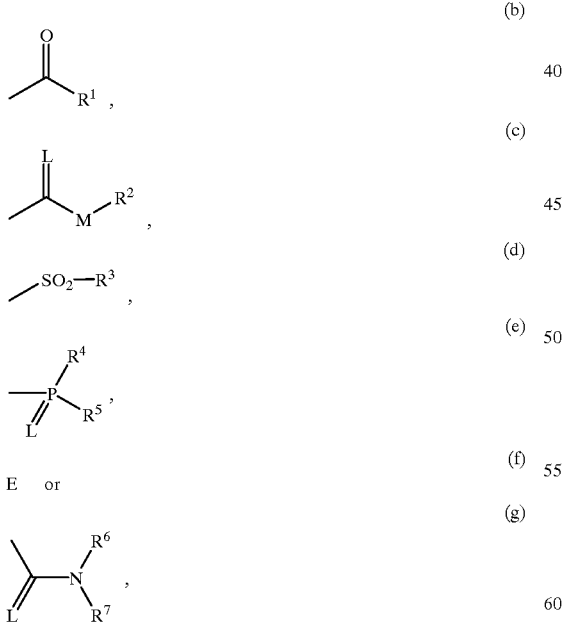

in which
E represents a metal ion equivalent or an ammonium ion,
L represents oxygen or sulphur and
M represents oxygen or sulphur.

$R^1$ particularly preferably represents respectively optionally fluorine- or chlorine-substituted $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl or poly-$C_1$–$C_6$-alkoxy-$C_1$–$C_6$-alkyl or optionally fluorine-, chlorine-, $C_1$–$C_5$-alkyl- or $C_1$–$C_5$-alkoxy-substituted $C_3$–$C_7$-cycloalkyl in which one or two not directly adjacent methylene groups are optionally replaced by oxygen and/or sulphur, optionally fluorine-, chlorine-, bromine-, cyano-, nitro-, $C_1$–$C_4$-alkyl-, $C_1$–$C_4$-alkoxy-, $C_1$–$C_3$-halogenoalkyl-, $C_1$–$C_3$-halogenoalkoxy-, $C_1$–$C_4$-alkylthio- or $C_1$–$C_4$-alkylsulphonyl-substituted phenyl, optionally fluorine-, chlorine-, bromine-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl-$C_1$–$C_4$-alkyl, optionally fluorine-, chlorine-, bromine- or $C_1$–$C_4$-alkyl-substituted pyrazolyl, thiazolyl, pyridyl, pyrimidyl, furanyl or thienyl, optionally fluorine-, chlorine-, bromine- or $C_1$–$C_4$-alkyl-substituted phenoxy-$C_1$–$C_5$-alkyl or respectively optionally fluorine-, chlorine-, bromine-, amino- or $C_1$–$C_4$-alkyl-substituted pyridyloxy-$C_1$–$C_5$-alkyl, pyrimidyloxy-$C_1$–$C_5$-alkyl or thiazolyloxy-$C_1$–$C_5$-alkyl.

$R^2$ particularly preferably represents respectively optionally fluorine- or chlorine-substituted $C_1$–$C_{16}$-alkyl, $C_2$–$C_{16}$-alkenyl, $C_1$–$C_6$-alkoxy-$C_2$–$C_6$-alkyl or poly-$C_1$–$C_6$-alkoxy-$C_2$–$C_6$-alkyl, optionally fluorine-, chlorine-, $C_1$–$C_4$-alkyl- or $C_1$–$C_4$-alkoxy-substituted $C_3$–$C_7$-cycloalkyl or respectively optionally fluorine-, chlorine-, bromine-, cyano-, nitro-, $C_1$–$C_4$-alkyl-, $C_1$–$C_3$-alkoxy-, $C_1$–$C_3$-halogenoalkyl- or $C_1$–$C_3$-halogenoalkoxy-substituted phenyl or benzyl.

$R^3$ particularly preferably represents optionally fluorine- or chlorine-substituted $C_1$–$C_6$-alkyl or respectively optionally fluorine-, chlorine-, bromine-, $C_1$–$C_4$-alkyl-, $C_1$–$C_4$-alkoxy-, $C_1$–$C_2$-halogenoalkoxy-, $C_1$–$C_2$-halogenoalkyl-, cyano- or nitro-substituted phenyl or benzyl.

$R^4$ and $R^5$ each particularly preferably represent independently of one another respectively optionally fluorine- or chlorine-substituted $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio or $C_3$–$C_4$-alkenylthio or respectively optionally fluorine-, chlorine-, bromine-, nitro-, cyano-, $C_1$–$C_3$-alkoxy-, $C_1$–$C_3$-halogenoalkoxy-, $C_1$–$C_3$-alkylthio-, $C_1$–$C_3$-halogenoalkylthio, $C_1$–$C_3$-alkyl- or $C_1$–$C_3$-halogenoalkyl-substituted phenyl, phenoxy or phenylthio.

$R^6$ and $R^7$ each particularly preferably represent independently of one another hydrogen, respectively optionally fluorine- or chlorine-substituted $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_2$–$C_6$-alkyl, respectively optionally fluorine-, chlorine-, bromine-, $C_1$–$C_5$-halogenoalkyl-, $C_1$–$C_5$-alkyl- or $C_1$–$C_5$-alkoxy-substituted phenyl or benzyl, or particularly preferably represent together an optionally $C_1$-$C_4$-alkyl-substituted $C_3$–$C_6$-alkylene radical in which one methylene group is optionally replaced by oxygen or sulphur.

$R^{13}$ particularly preferably represents hydrogen or respectively optionally fluorine- or chlorine-substituted $C_1$–$C_6$-alkyl or $C_1$–$C_6$-alkoxy, optionally fluorine-, $C_1$–$C_2$-alkyl- or $C_1$–$C_2$-alkoxy-substituted $C_3$–$C_7$- cycloalkyl in which one methylene group is optionally replaced by oxygen or sulphur, or particularly preferably represents respectively optionally fluorine-, chlorine-, bromine-, $C_1$–$C_5$-alkyl-, $C_1$–$C_5$-alkoxy-, $C_1$–$C_2$-halogenoalkyl-, $C_1$–$C_2$-halogenoalkoxy-, nitro- or cyano-substituted phenyl, phenyl-$C_1$–$C_3$-alkyl or phenyl-$C_1$–$C_2$-alkyloxy.

$R^{14}$ particularly preferably represents hydrogen or $C_1$–$C_6$-alkyl or $R^{13}$ and $R^{14}$ together particularly preferably represent $C_4$–$C_6$-alkanediyl.

$R^{15}$ and $R^{16}$ are identical or different and particularly preferably represent $C_1$–$C_4$-alkyl or $R^{15}$ and $R^{16}$ together particularly preferably represent a $C_2$–$C_3$-alkanediyl radical which is optionally substituted by $C_1$–$C_4$-alkyl or optionally fluorine-, chlorine-, bromine-, $C_1$–$C_2$-alkyl-, $C_1$–$C_2$-halogenoalkyl-, $C_1$–$C_2$-alkoxy-, $C_1$–$C_2$-halogenoalkoxy-, nitro- or cyano-substituted phenyl.

V very particularly preferably represents hydrogen, fluorine, chlorine, bromine, methyl, ethyl, propyl, isopropyl, tert-butyl, methoxy, ethoxy, propoxy or isopropoxy.

W very particularly preferably represents cyano, nitro, fluorine, chlorine, bromine, methyl, ethyl, propyl, butyl, isopropyl, isobutyl, tert-butyl, methoxy, ethoxy, propoxy, isopropoxy, trifluoromethyl, difluoromethoxy, trifluoromethoxy, phenyl or benzyloxy.

X very particularly preferably represents hydrogen, fluorine, chlorine, bromine, methyl, ethyl, propyl, butyl, isobutyl, isopropyl, tert-butyl, methoxy, ethoxy, propoxy, isopropoxy, trifluoromethyl, trifluoromethoxy, difluoromethoxy, cyano, nitro, phenyl or benzyloxy.

Y very particularly preferably represents hydrogen, fluorine, chlorine, bromine, methyl, ethyl, propyl, isopropyl, butyl, isobutyl, tert-butyl, methoxy, ethoxy, propoxy, isopropoxy, trifluoromethyl, trifluoromethoxy, difluoromethoxy, cyano or nitro.

Z very particularly preferably represents fluorine, chlorine, bromine, methyl, ethyl, propyl, butyl, isobutyl, isopropyl, tert-butyl, methoxy, ethoxy, propoxy, isopropoxy, trifluoromethyl, trifluoromethoxy, difluoromethoxy, cyano or nitro, or Y and Z together very particularly preferably represent optionally fluorine-, chlorine-, methyl-, ethyl-, propyl-, isopropyl-, methoxy-, ethoxy-, propoxy-, isopropoxy- or trifluoromethyl-substituted $C_3$–$C_4$-alkanediyl in which two not directly adjacent members are optionally replaced by oxygen, or W and Z together very particularly preferably represent optionally fluorine-, chlorine-, methyl-, ethyl-, propyl-, isopropyl-, methoxy-, ethoxy-, propoxy-, isopropoxy- or trifluoromethyl-substituted $C_3$–$C_4$-alkanediyl in which two not directly adjacent members are optionally replaced by oxygen.

Het very particularly preferably represents one of the groups

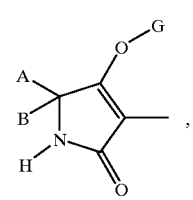

(1)

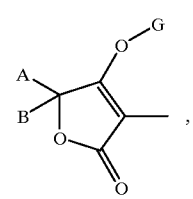

(2)

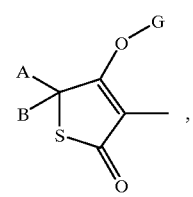

(3)

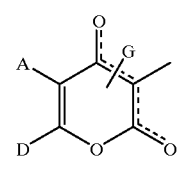

(4)

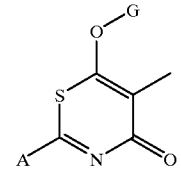

(5)

A very particularly preferably represents hydrogen, respectively optionally fluorine- or chlorine-substituted $C_1$–$C_8$-alkyl, $C_2$–$C_4$-alkenyl, $C_1$–$C_6$-alkoxy-$C_1$–$C_4$-alkyl, poly-$C_1$–$C_4$-alkoxy-$C_1$–$C_4$-alkyl or $C_1$-$C_6$-alkylthio-$C_1$–$C_4$-alkyl or optionally fluorine-, chlorine-, methyl- or methoxy-substituted $C_3$–$C_6$-cycloalkyl in which one or two not directly adjacent methylene groups are optionally replaced by oxygen and/or sulphur, or very particularly preferably represents respectively optionally fluorine-, chlorine-, bromine-, methyl-, ethyl-, n-propyl-, isopropyl-, methoxy-, ethoxy-, trifluoromethyl-, trifluoromethoxy-, cyano- or nitro-substituted phenyl, pyridyl or benzyl.

B very particularly preferably represents hydrogen, $C_1$–$C_8$-alkyl or $C_1$–$C_4$-alkoxy-$C_1$–$C_2$-alkyl or A, B and the carbon atom that they are attached to very particularly preferably represent $C_3$–$C_8$-cycloalkyl or $C_5$–$C_8$-cycloalkenyl where in each case one methylene group is optionally replaced by oxygen or sulphur and which are optionally substituted by methyl, ethyl, n-propyl, isopropyl, butyl, isobutyl, sec-butyl, tert-butyl, cyclohexyl, trifluoromethyl, methoxy, ethoxy, n-propoxy, isopropoxy, butoxy, isobutoxy, sec-butoxy, tert-butoxy, methylthio, ethylthio, fluorine, chlorine or phenyl or A, B and the carbon atom that they are attached to very particularly preferably represent $C_5$–$C_6$-cycloalkyl which is substituted by an alkylenediyl group optionally containing an oxygen or sulphur atom, or by an alkylenedioxy group forming a further five- or six-membered ring with the carbon atom that it is attached to or A, B and the carbon atom that they are attached to very particularly preferably represent $C_3$–$C_6$-cycloalkyl or $C_5$–$C_6$-cycloalkenyl in which two carbon atoms are connected by $C_3$–$C_4$-alkanediyl, $C_3$–$C_4$-alkenediyl or butadienediyl.

D very particularly preferably represents hydrogen, respectively optionally fluorine- or chlorine-substituted $C_1$–$C_8$-alkyl, $C_3$–$C_4$-alkenyl, $C_3$–$C_4$-alkinyl, $C_1$–$C_6$-alkoxy-$C_2$–$C_4$-alkyl, poly-$C_1$–$C_4$-alkoxy-$C_2$–$C_4$-alkyl, $C_1$–$C_4$-alkylthio-$C_2$–$C_4$-alkyl or $C_3$–$C_6$-cycloalkyl in which one or two not directly adjacent methylene groups are optionally replaced by oxygen and/or sulphur, or very particularly preferably represents respectively optionally fluorine-, chlorine-, bromine-, methyl-, ethyl-, n-propyl-, isopropyl-, methoxy-, ethoxy-, trifluoromethyl-, trifluoromethoxy-, cyano- or nitro-substituted phenyl, furanyl, pyridyl, thienyl or benzyl, or A and D together very particularly preferably represent a $C_3$–$C_5$-alkanediyl or $C_3$–$C_5$-alkenediyl group where in each case one methylene group is optionally replaced by oxygen or sulphur and which are optionally substituted by fluorine, chlorine or respectively optionally fluorine- or chlorine-substituted $C_1$–$C_6$-alkyl or $C_1$–$C_4$-alkoxy.

G very particularly preferably represents hydrogen (a) or one of the groups

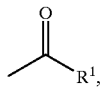

(b)

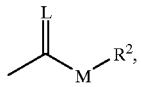

(c)

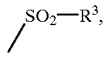

(d)

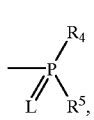

(e)

E or (f)

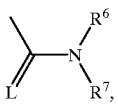

(g)

in which

E represents a metal ion equivalent or an ammonium ion,

L represents oxygen or sulphur and

M represents oxygen or sulphur.

$R^1$ very particularly preferably represents respectively optionally fluorine- or chlorine-substituted $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, poly-$C_1$–$C_4$-alkoxy-$C_1$–$C_4$-alkyl or optionally fluorine-, chlorine-, methyl-, ethyl-, n-propyl-, i-propyl-, n-butyl-, i-butyl-, tert-butyl-, methoxy-, ethoxy-, n-propoxy- or isopropoxy-substituted $C_3$–$C_6$-cycloalkyl in which one or two not directly adjacent methylene groups are optionally replaced by oxygen and/or sulphur, optionally fluorine-, chlorine-, bromine-, cyano-, nitro-, methyl-, ethyl-, n-propyl-, i-propyl-, methoxy-, ethoxy-, trifluoromethyl-, trifluoromethoxy-, methylthio-, ethylthio-, methylsulphonyl- or ethylsulphonyl-substituted phenyl, optionally fluorine-, chlorine-, bromine-, methyl-, ethyl-, n-propyl-, i-propyl-, methoxy-, ethoxy-, trifluoromethyl- or trifluoromethoxy-substituted benzyl, respectively optionally fluorine-, chlorine-, bromine-, methyl- or ethyl-substituted furanyl, thienyl or pyridyl, optionally fluorine-, chlorine-, methyl- or ethyl-substituted phenoxy-$C_1$–$C_4$-alkyl or respectively optionally fluorine-, chlorine-, amino-, methyl- or ethyl-substituted pyridyloxy-$C_1$–$C_4$-alkyl, pyrimidyloxy-$C_1$–$C_4$-alkyl or thiazolyloxy-$C_1$–$C_4$-alkyl.

$R^2$ very particularly preferably represents respectively optionally fluorine- or chlorine-substituted $C_1$–$C_{14}$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl, optionally fluorine-, chlorine-, methyl-, ethyl-, n-propyl-, isopropyl- or methoxy-substituted $C_3$–$C_6$-cycloalkyl, or respectively optionally fluorine-, chlorine-, cyano-, nitro-, methyl-, ethyl-, n-propyl-, i-propyl-, methoxy-, ethoxy-, trifluoromethyl- or trifluoromethoxy-substituted phenyl or benzyl.

$R^3$ very particularly preferably represents optionally fluorine- or chlorine-substituted methyl, ethyl, propyl, isopropyl, butyl, tert-butyl, or respectively optionally fluorine-, chlorine-, bromine-, methyl-, ethyl-, isopropyl-, tert-butyl-, methoxy-, ethoxy-, isopropoxy-, trifluoromethyl-, trifluoromethoxy-, cyano- or nitro-substituted phenyl or benzyl.

$R^4$ and $R^5$ each very particularly preferably represent independently of one another respectively optionally fluorine- or chlorine-substituted $C_1$–$C_4$-alkyl, $C_1$–$C_4$-alkoxy, $C_1$–$C_4$-alkylamino, di-($C_1$–$C_4$-alkyl)amino or $C_1$–$C_4$-alkylthio or respectively optionally fluorine-, chlorine-, bromine-, nitro-, cyano-, methyl-, methoxy-, trifluoromethyl- or trifluoromethoxy-substituted phenyl, phenoxy or phenylthio.

$R^6$ and $R^7$ each very particularly preferably represent independently of one another hydrogen, respectively optionally fluorine- or chlorine-substituted $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_2$–$C_4$-alkyl, respectively optionally fluorine-, chlorine-, bromine-, methyl-, methoxy- or trifluoromethyl-substituted phenyl or benzyl or together represent an optionally methyl- or ethyl-substituted $C_5$–$C_6$-alkylene radical in which one methylene group is optionally replaced by oxygen or sulphur.

Excluded are in each case the following compounds (disclosed in EP-0 528 156):

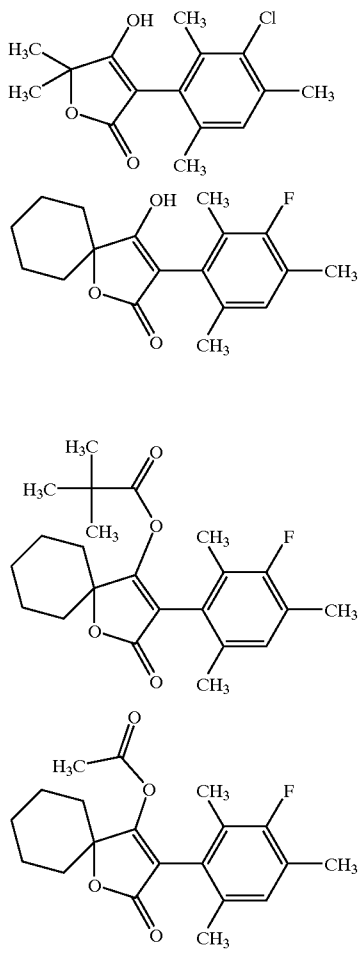

If, in the compounds of the formula (I-2), only the substituent V of the substituents X, V, Y, Z and W represents hydrogen and X, Y, Z and W have a meaning different from hydrogen, then preference is given to such compounds of the formula (I-2) in which Z does not represent halogen.

The abovementioned definitions or illustrations of radicals mentioned generally or in preferred ranges can be combined with each other as desired, i.e. also between the respective ranges and preferred ranges. They apply correspondingly to the final products and to the precursors and intermediates.

For the purpose of the invention, preference is given to compounds of the formula (I) in which there exists a combination of the meanings mentioned above as preferred (preferable).

For the purpose of the invention, particular preference is given to compounds of the formula (I) in which there exists a combination of the meanings mentioned above as particularly preferred.

For the purpose of the invention, very particular preference is given to the compounds of the formula (I) in which there exists a combination of the meanings mentioned above as very particularly preferred.

Saturated or unsaturated hydrocarbon radicals such as alkyl or alkenyl can, as far as possible, in each case be straight-chain or branched, also in combination with heteroatoms, e.g. in alkoxy.

Optionally substituted radicals can be mono- or polysubstituted, it being possible in the case of polysubstitution for the substituents to be identical or different.

Particular preference is given to compounds of the formula I-1 to I-3 in which a) A, B and the carbon atom that they are attached to have the meanings mentioned as very particularly preferred and V represents hydrogen, b) A, B and the carbon atom that they are attached to have the meanings mentioned as very particularly preferred and V and Y represent hydrogen.

In addition to the compounds mentioned in the Preparation Examples, the following compounds of the formula (I-1-a) may be specifically mentioned:

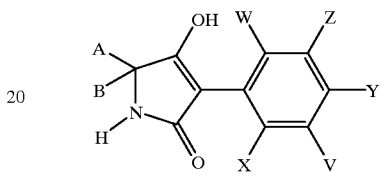

TABLE 1

$V = H; W = CH_3; X = CH_3; Y = CH_3; Z = CH_3$

| A | B |
|---|---|
| $CH_3$ | H |
| $C_2H_5$ | H |
| $C_3H_7$ | H |
| $i\text{-}C_3H_7$ | H |
| $C_4H_9$ | H |
| $i\text{-}C_4H_9$ | H |
| $s\text{-}C_4H_9$ | H |
| $t\text{-}C_4H_9$ | H |
| $CH_3$ | $CH_3$ |
| $C_2H_5$ | $CH_3$ |
| $C_3H_7$ | $CH_3$ |
| $i\text{-}C_3H_7$ | $CH_3$ |
| $C_4H_9$ | $CH_3$ |
| $i\text{-}C_4H_9$ | $CH_3$ |
| $s\text{-}C_4H_9$ | $CH_3$ |
| $t\text{-}C_4H_9$ | $CH_3$ |
| $C_2H_5$ | $C_2H_5$ |
| $C_3H_7$ | $C_3H_7$ |
| cyclopropyl | $CH_3$ |
| cyclopentyl | $CH_3$ |
| cyclohexyl | $CH_3$ |
| $-(CH_2)_2-$ | |
| $-(CH_2)_4-$ | |
| $-(CH_2)_5-$ | |
| $-(CH_2)_6-$ | |
| $-(CH_2)_7-$ | |
| $-(CH_2)_2-O-(CH_2)_2-$ | |
| $-(CH_2)_2-S-(CH_2)_2-$ | |
| $-CH_2-CHCH_3-(CH_2)_3-$ | |
| $-(CH_2)_2-CHCH_3-(CH_2)_2-$ | |
| $-(CH_2)_2-CHC_2H_5-(CH_2)_2-$ | |
| $-(CH_2)_2-CHC_3H_7-(CH_2)_2-$ | |
| $-(CH_2)_2-CHi\text{-}C_3H_7-(CH_2)_2-$ | |

TABLE 1-continued

V = H; W = CH₃; X = CH₃; Y = CH₃; Z = CH₃

| A | B |
|---|---|
| —(CH₂)₂—CHOCH₃—(CH₂)₂— | |
| —(CH₂)₂—CHOC₂H₅—(CH₂)₂— | |
| —(CH₂)₂—CHOC₃H₇—(CH₂)₂— | |
| —(CH₂)₂—CHOi-C₃H₇—(CH₂)₂— | |
| —(CH₂)₂—C(CH₃)₂—(CH₂)₂— | |
| —CH₂—(CHCH₃)₂—(CH₂)₂— | |

—CH₂—CH—(CH₂)₂—CH—
         └—CH₂—┘

—CH₂—CH—————CH—CH₂—
         └—(CH₂)₄—┘

—CH₂—CH—————CH—(CH₂)₂—
         └—(CH₂)₃—┘

(indane structure)

(tetralin structure)

Table 2
A and B are as defined in Table 1 with V=H; W=CH₃; X=CH₃; Y=H; Z=Cl

Table 3
A and B are as defined in Table 1 with V=H; W=CH₃; X=CH₃; Y=CH₃; Z=F

Table 4
A and B are as defined in Table 1 with V=H; W=CH₃; X=CH₃; Y=C₃; Z=Cl

Table 5
A and B are as defined in Table 1 with V=H; W=CH₃; X=CH₃; Y=CH₃; Z=Br

Table 6
A and B are as defined in Table 1 with V=CH₃; W=CH₃; X=CH₃; Y=H; Z=CH₃

Table 7
A and B are as defined in Table 1 with V=CH₃; W=CH₃; X=H; Y=CH₃; Z=CH₃

Table 8
A and B are as defined in Table 1 with V=H; W=CH₃; X=CH₃; Y=H; Z=Br

Table 9
A and B are as defined in Table 1 with V=H; W=Cl; X=Cl; Y=H; Z=Br

Table 10
A and B are as defined in Table 1 with V=H; W=Br; X=Br; Y, Z=—(CH₂)₃—

Table 11
A and B are as defined in Table 1 with V=H; W=CH₃; X=OCH₃; Y=H; Z=Br

Table 12
A and B are as defined in Table 1 with V=CH₃; W=CH₃; X=CH₃; Y=CH₃; Z=CH₃

Table 13
A and B are as defined in Table 1 with V=H; W=Cl; X=Cl; Y=Cl; Z=CH₃

Table 14
A and B are as defined in Table 1 with V=H; W=Br; X=Br; Y=Br; Z=CH₃

In addition to the compounds mentioned in the Preparation Examples, the following compounds of the formula (I-2-a) may be specifically mentioned:

(structure of formula I-2-a with OH, W, Z, Y, V, X substituents on fused furan-phenyl system)

TABLE 15

V = H, W = CH₃; X = CH₃; Y = CH₃; Z = CH₃

| A | B |
|---|---|
| CH₃ | H |
| C₂H₅ | H |
| C₃H₇ | H |
| i-C₃H₇ | H |
| C₄H₉ | H |
| i-C₄H₉ | H |
| s-C₄H₉ | H |
| t-C₄H₉ | H |
| CH₃ | CH₃ |
| C₂H₅ | CH₃ |
| C₃H₇ | CH₃ |
| i-C₃H₇ | CH₃ |
| C₄H₉ | CH₃ |
| i-C₄H₉ | CH₃ |
| s-C₄H₉ | CH₃ |
| t-C₄H₉ | CH₃ |
| C₂H₅ | C₂H₅ |
| C₃H₇ | C₃H₇ |
| cyclopropyl | CH₃ |
| cyclopentyl | CH₃ |
| cyclohexyl | CH₃ |
| —(CH₂)₂— | |
| —(CH₂)₄— | |
| —(CH₂)₅— | |
| —(CH₂)₆— | |
| —(CH₂)₇— | |
| —(CH₂)₂—O—(CH₂)₂— | |
| —(CH₂)₂—S—(CH₂)₂— | |
| —CH₂—CHCH₃—(CH₂)₃— | |
| —(CH₂)₂—CHCH₃—(CH₂)₂— | |
| —(CH₂)₂—CHC₂H₅—(CH₂)₂— | |
| —(CH₂)₂—CHC₃H₇—(CH₂)₂— | |
| —(CH₂)₂—CHi-C₃H₇—(CH₂)₂— | |
| —(CH₂)₂—CHOCH₃—(CH₂)₂— | |
| —(CH₂)₂—CHOC₂H₅—(CH₂)₂— | |
| —(CH₂)₂—CHOC₃H₇—(CH₂)₂— | |
| —(CH₂)₂—CHOi-C₃H₇—(CH₂)₂— | |
| —(CH₂)₂—C(CH₃)₂—(CH₂)₂— | |
| —CH₂—(CHCH₃)₂—(CH₂)₂— | |

TABLE 15-continued

V = H; W = CH₃; X = CH₃; Y = CH₃; Z = CH₃

| A | B |
|---|---|
| —CH₂—CH—(CH₂)₂—CH—<br>└—CH₂—┘ | |
| —CH₂—CH————CH—CH₂—<br>└—(CH₂)₄—┘ | |
| —CH₂—CH————CH—(CH₂)₂—<br>└—(CH₂)₃—┘ | |

(indane diyl structure)

(tetralin diyl structure)

Table 16

A and B are as defined in Table 15 with V=H; W=CH₃; X=CH₃; Y=H; Z=Cl

Table 17

A and B are as defined in Table 15 with V=CH₃; W=CH₃; X=CH₃; Y=H; Z=CH₃

Table 18

A and B are as defined in Table 15 with V=CH₃; W=CH₃; X=H; Y=CH₃; Z=CH₃

Table 19

A and B are as defined in Table 15 with V=H; W=CH₃; X=CH₃; Y=H; Z=Br

Table 20

A and B are as defined in Table 15 with V=H; W=Cl; X=Cl; Y=H; Z=Br

Table 21

A and B are as defined in Table 15 with V=H; W=Br; X=Br; Y, Z=—(CH₃)₂—

Table 22

A and B are as defined in Table 15 with V=H; W=CH₃; X=OCH₃; Y=H; Z=Br

Table 23

A and B are as defined in Table 15 with V=CH₃; W=CH₃; X=CH₃; Y=CH₃; Z=CH₃

Table 24

A and B are as defined in Table 15 with V=H; W=Cl; X=Cl; Y=Cl; Z=CH₃

Table 25

A and B are as defined in Table 15 with V=H; W=Br; X=Br, Z=CH₃

In addition to the compounds mentioned in the Preparation Examples, the following compounds of the formula (I-3-a) may be specifically mentioned:

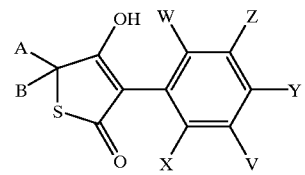

TABLE 26

V = H; W = CH₃; X = CH₃; Y = CH₃; Z = CH₃

| A | B |
|---|---|
| CH₃ | H |
| C₂H₅ | H |
| C₃H₇ | H |
| i-C₃H₇ | H |
| C₄H₉ | H |
| i-C₄H₉ | H |
| s-C₄H₉ | H |
| t-C₄H₉ | H |
| CH₃ | CH₃ |
| C₂H₅ | CH₃ |
| C₃H₇ | CH₃ |
| i-C₃H₇ | CH₃ |
| C₄H₉ | CH₃ |
| i-C₄H₉ | CH₃ |
| s-C₄H₉ | CH₃ |
| t-C₄H₉ | CH₃ |
| C₂H₅ | C₂H₅ |
| C₃H₇ | C₃H₇ |
| cyclopropyl | CH₃ |
| cyclopentyl | CH₃ |
| cyclohexyl | CH₃ |
| —(CH₂)₂— | |
| —(CH₂)₄— | |
| —(CH₂)₅— | |
| —(CH₂)₆— | |
| —(CH₂)₇— | |
| —(CH₂)₂—O—(CH₂)₂— | |
| —(CH₂)₂—S—(CH₂)₂— | |
| —CH₂—CHCH₃—(CH₂)₃— | |
| —(CH₂)₂—CHCH₃—(CH₂)₂— | |
| —(CH₂)₂—CHC₂H₅—(CH₂)₂— | |
| —(CH₂)₂—CHC₃H₇—(CH₂)₂— | |
| —(CH₂)₂—CHi-C₃H₇—(CH₂)₂— | |
| —(CH₂)₂—CHOCH₃—(CH₂)₂— | |
| —(CH₂)₂—CHOC₂H₅—(CH₂)₂— | |
| —(CH₂)₂—CHOC₃H₇—(CH₂)₂— | |
| —(CH₂)₂—CHOi-C₃H₇—(CH₂)₂— | |
| —(CH₂)₂—C(CH₃)₂—(CH₂)₂— | |
| —CH₂—(CHCH₃)₂—(CH₂)₂— | |
| —CH₂—CH—(CH₂)₂—CH—<br>└—CH₂—┘ | |
| —CH₂—CH————CH—CH₂—<br>└—(CH₂)₄—┘ | |

TABLE 26-continued

V = H; W = CH₃; X = CH₃; Y = CH₃; Z = CH₃

| A | B |
|---|---|
| —CH₂—CH(—(CH₂)₃—)—CH—(CH₂)₂— (indane fused) | |
| (tetralin fused) | |

Table 27
A and B are as defined in Table 26 with V=H; W=CH₃; X=CH₃; Y=H; Z=Cl

Table 28
A and B are as defined in Table 26 with V=H; W=CH₃; X=CH₃; Y=CH₃; Z=Cl

Table 29
A and B are as defined in Table 26 with V=H; W=CH₃; X=CH₃; Y=CH₃; Z=F

Table 30
A and B are as defined in Table 26 with V=H; W=CH₃; X=CH₃; Y=CH₃; Z=Br

Table 31
A and B are as defined in Table 26 with V=CH₃; W=CH₃; X=CH₃; Y=H; Z=CH₃

Table 32
A and B are as defined in Table 26 with V=CH₃; W=CH₃; X=H; Y=CH₃; Z=CH₃

Table 33
A and B are as defined in Table 26 with V=H; W=CH₃; X=CH₃; Y=H; Z=Br

Table 34
A and B are as defined in Table 26 with V=H; W=Cl; X=Cl; Y=H; Z=Br

Table 35
A and B are as defined in Table 26 with V=H; W=Br; X=Br; Y, Z=—(CH₂)₃—

Table 36
A and B are as defined in Table 26 with V=H; W=CH₃; X=OCH₃; Y=H; Z=Br

Table 37
A and B are as defined in Table 26 with V=CH₃; W=CH₃; X=CH₃; Y=CH₃; Z=CH₃

Table 38
A and B are as defined in Table 26 with V=H; W=Cl; X=Cl; Y=Cl; Z=CH₃

Table 39
A and B are as defined in Table 26 with V=H; W=Br; X=Br; Y=Br; Z=CH₃

In addition to the compounds mentioned in the Preparation Examples, the following compounds of the formula (I-4-a) may be specifically mentioned:

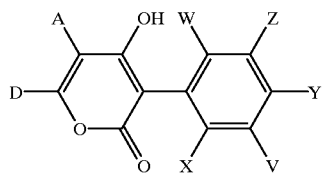

TABLE 40

V = H; W = CH₃; X = CH₃; Y = CH₃; Z = CH₃

| A | D |
|---|---|
| H | CH₃ |
| H | C(CH₃)₃ |
| H | C(CH₃)₂CH₂Cl |
| CH₃ | CH₃ |
| CH₃ | CH₂CHCH₃CH₂CH₃ |
| H | CH=C(CH₃)₂ |
| CH₃ | 4-F-phenyl |
| CH₃ | 4-Cl-phenyl |
| CH₃ | 2,4-F₂-phenyl |
| CH₃ | 3,4-Cl₂-phenyl |
| CH₃ | 4-OCF₃-phenyl |
| CH₃ | phenyl |
| H | 2-furyl |
| CH₃ | 2-thienyl |
| CH₃ | 2-pyridyl |

TABLE 40-continued

V = H; W = CH₃; X = CH₃; Y = CH₃; Z = CH₃

| A | D |
|---|---|
| CH₃ | 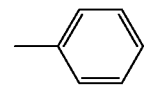 |
| CH₃ | 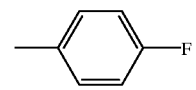 |
| H | 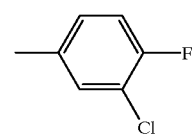 |
| CH₃ | C₅H₉ |
| CH₃ | C₃H₅ |
| H | C₃H₄Cl |
| | (CH₂)₃ |
| | (CH₂)₄ |
| | C(CH₃)₂OC(CH₃)₂ |

Table 41

A and D are as defined in Table 40 with V=H; W=CH₃; X=CH₃; Y=H; Z=Cl

Table 42

A and D are as defined in Table 40 with V=H; W=CH₃; X=CH₃; Y=CH₃; Z=Cl

Table 43

A and D are as defined in Table 40 with V=H; W=CH₃; X=C₃; Y=CH₃; Z=F

Table 44

A and D are as defined in Table 40 with V=H; W=CH₃; X=CH₃; Y=CH₃; Z=Br

Table 45

A and D are as defined in Table 40 with V=CH₃; W=CH₃; X=CH₃; Y=H; Z=CH₃

Table 46

A and D are as defined in Table 40 with V=CH₃; W=CH₃; X=H; Y=CH₃; Z=CH₃

Table 47

A and D are as defined in Table 40 with V=H; W=CH₃; X=CH₃; Y=H; Z=Br

Table 48

A and D are as defined in Table 40 with V=H; W=Cl; X=Cl; Y=H; Z=Br

Table 49

A and D are as defined in Table 40 with V=H; W=Br; X=Br; Y, Z=—(CH₂)₃—

Table 50

A and D are as defined in Table 40 with V=H; W=CH₃; X=OCH₃; Y=H; Z=Br

Table 51

A and D are as defined in Table 40 with V=CH₃; W=CH₃; X=CH₃; Y=CH₃; Z=CH₃

Table 52

A and D are as defined in Table 40 with V=H; W=Cl; X=Cl; Y=Cl; Z=CH₃

In addition to the compounds mentioned in the Preparation Examples, the following compounds of the formula (I-5-a) may be specifically mentioned:

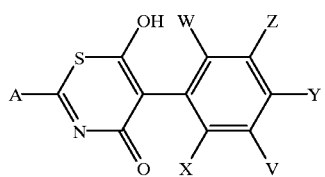

TABLE 54

V = H; W = CH₃; X = CH₃; Y = CH₃; Z = CH₃

A

CH₃
CH(CH₃)₂

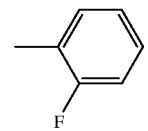

Table 55

A is as defined in Table 54 with V=H; W=CH₃; X=CH₃; Y=H; Z=Cl

Table 56

A is as defined in Table 54 with V=H; W=CH₃; X=CH₃; Y=CH₃; Z=Cl

If according to process (A) ethyl N-[(3,4-dichloro-2,6-dimethyl)-phenylacetyl]-1-amino-4-ethyl-cyclohexane-carboxylate is used as starting material, the course of the process according to the invention can be represented by the following reaction scheme:

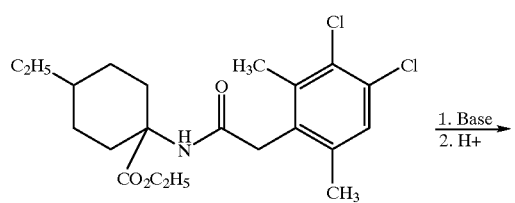

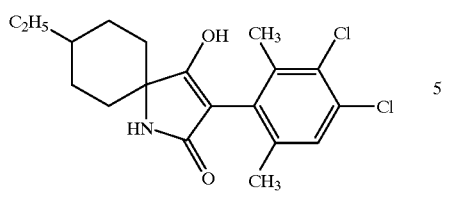

If according to process (B) ethyl O-[(2,5-dichloro-6-methyl)-phenylacetyl]hydroxyacetate is used, the course of the process according to the invention can be represented by the following reaction scheme:

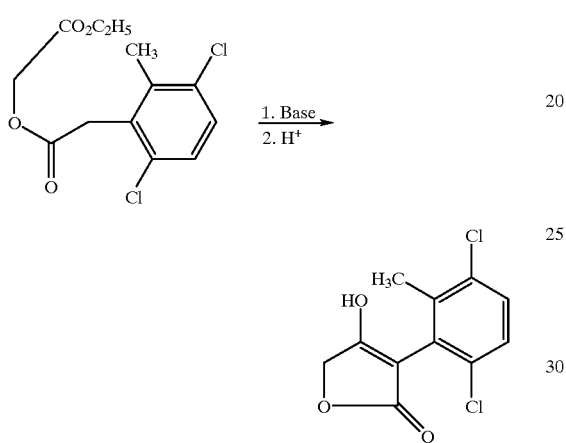

If according to process (C) ethyl 2-[(2-chloro-4,5,6-trimethyl)-phenyl]-4-(4-methoxy)-benzylmercapto-4-methyl-3-oxo-valerate is used, the course of the process according to the invention can be represented by the following reaction scheme:

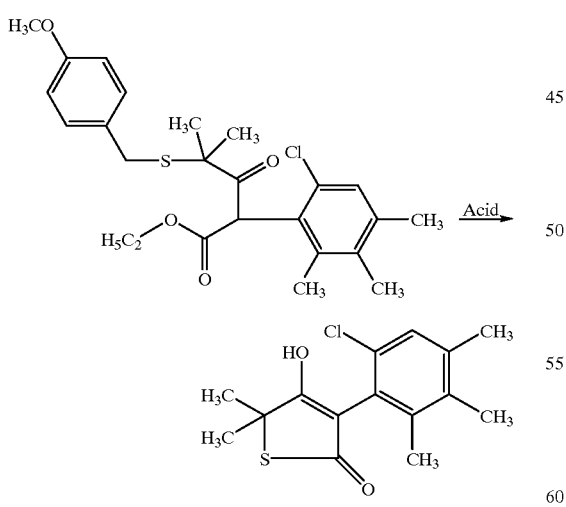

If, for example, according to process (D) chlorocarbonyl 2-[(3,4-dichloro-2,6-dimethyl)-phenyl]ketene and acetone are used as starting materials, the course of the process according to the invention can be represented by the following reaction scheme:

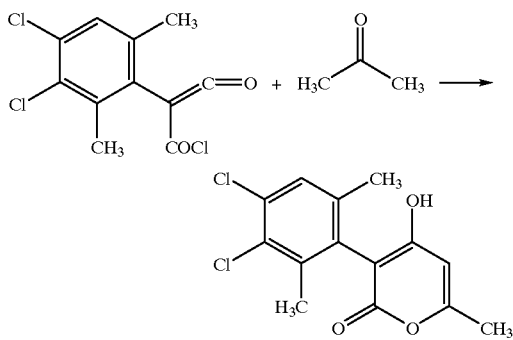

If, for example, according to process (E) chlorocarbonyl 2-[(2,3,4,6-tetramethyl)-phenyl]ketene and thiobenzamide are used as starting materials, the course of the process according to the invention can be represented by the following reaction scheme:

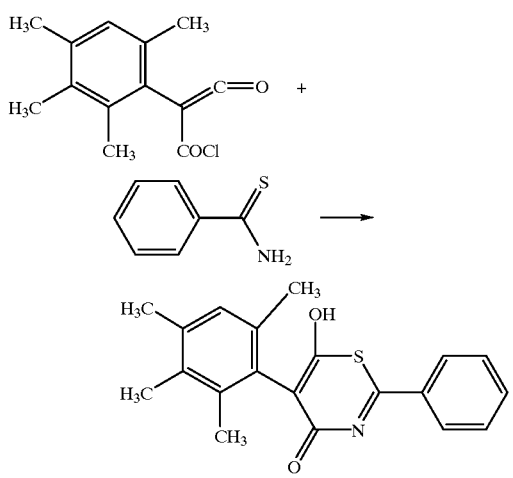

If according to process (Fα) 3-[(2,5-dichloro-4,6-dimethyl)-phenyl]-5,5-dimethylpyrrolidine-2,4-dione and pivaloyl chloride are used as starting materials, the course of the process according to the invention can be represented by the following reaction scheme:

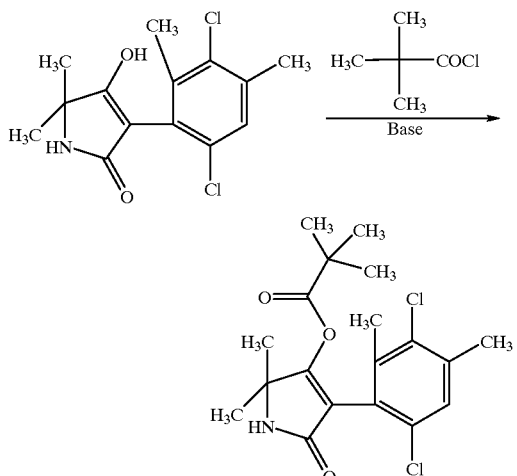

If according to process (F) (variant β) 3-[(2,3-dichloro)-phenyl]-4-hydroxy-5-phenyl-Δ³-dihydrofuran-2-one and acetic anhydride are used as starting materials, the course of the process according to the invention can be represented by the following reaction scheme:

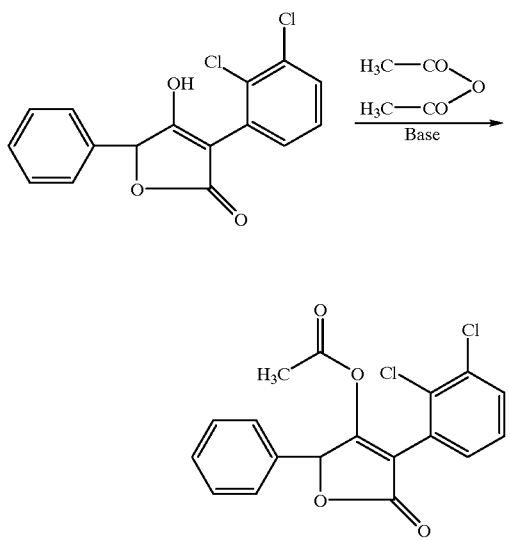

If according to process (G) 8-[(2,4-dichloro-3-methyl)-phenyl]-5,5-pentamethylenepyrrolidine-2,4-dione and ethoxyethyl chloroformate are used as starting materials, the course of the process according to the invention can be represented by the following reaction scheme:

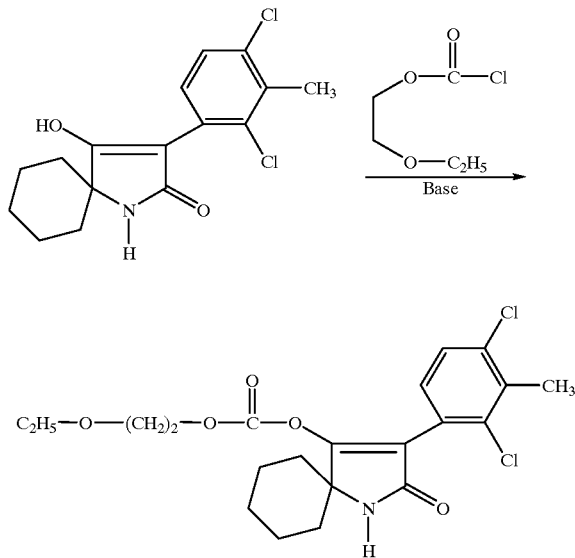

If according to the process (H), (variant α) 3-[(2,6-dibromo-3,4-dimethyl)-phenyl]-4-hydroxy-6-(3-pyridyl)-pyrone and methyl chloromonothioformate are used as starting materials, the course of the reaction can be represented in the following manner:

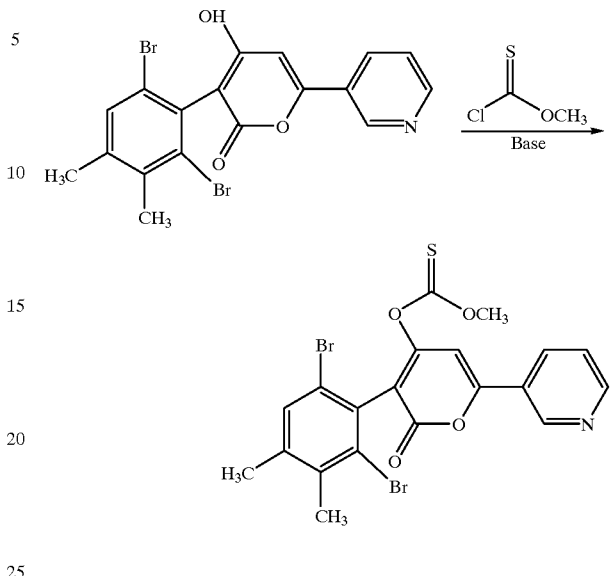

If according to process (H), (variant β) 5-[(3-chloro-2,6-dimethyl)-phenyl]-6-hydroxy-2-(4-chlorophenyl)-thiazin-4-one, carbon disulphide and methyl iodide are used as starting materials, the course of the reaction can be represented as follows:

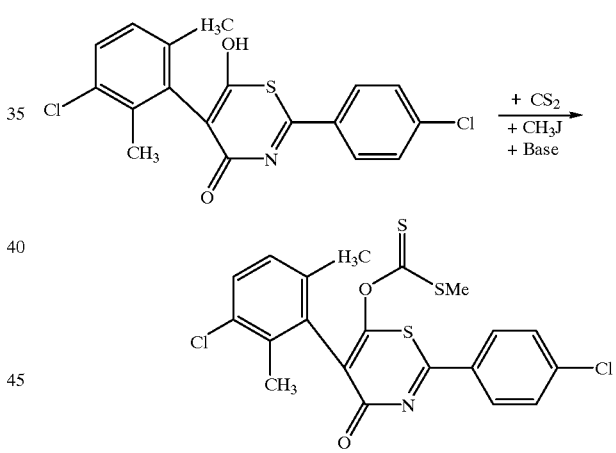

If according to process (I) 2-[(2,3,4,6-tetramethyl)-phenyl]-5,5-[(3-methyl)pentamethylene]-pyrrolidine-2,4-dione and methanesulphonyl chloride are used as starting materials, the course of the reaction can be represented by the following reaction scheme:

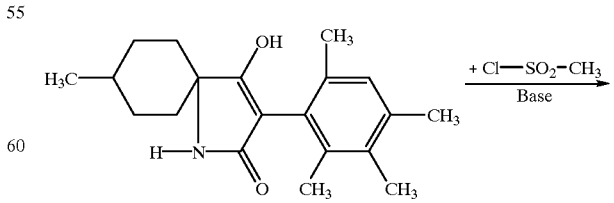

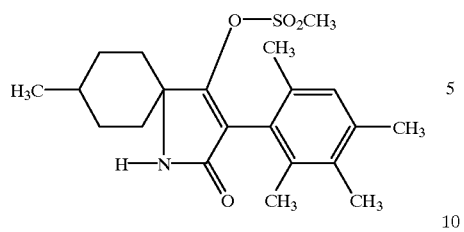

If according to process (J) 2-[(2-chloro-5,6-dimethyl)-phenyl]-4-hydroxy-5-methyl-6-(2-pyridyl)-pyrone and 2,2,2-trifluoroethyl chloromethanethio-phosphonate are used as starting materials, the course of the reaction can be represented by the following reaction scheme:

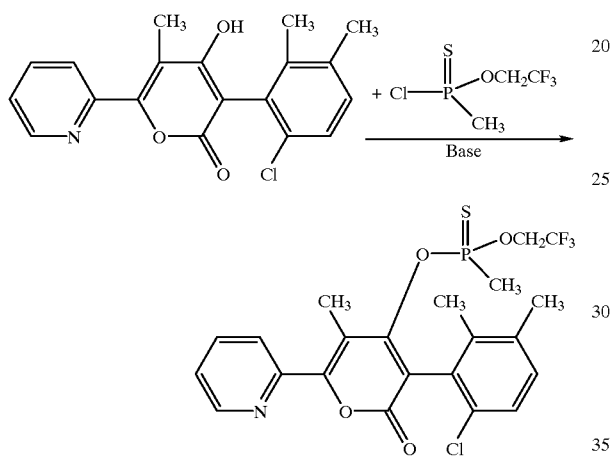

If according to process (K) 3-[(2,4,5-trichloro)-6-methylphenyl]-5-cyclopropyl-5-methyl-pyrrolidine-2,4-dione and NaOH are used as components, the course of the process according to the invention can be represented by the following reaction scheme:

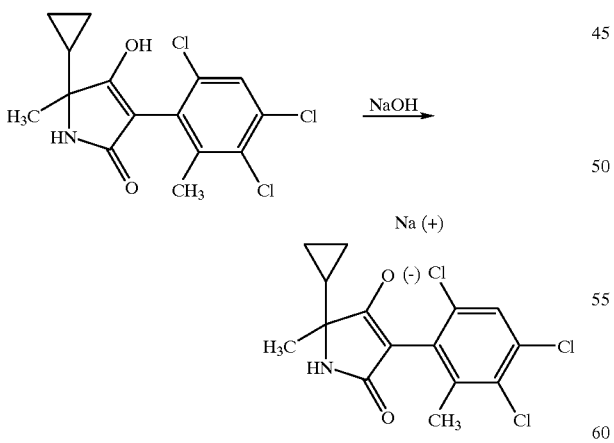

If according to process (L) (variant α) 3-[(2,6-dichloro-4-bromo-3-methyl)-phenyl]-4-hydroxy-5,5-tetramethylene-Δ³-dihydro-furan-2-one and ethyl isocyanate are used as starting materials, the course of the reaction can be represented by the following reaction scheme:

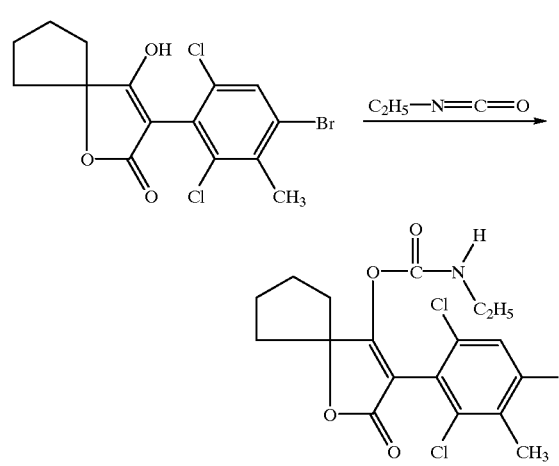

If according to process (L) (variant β) 3-[(2-chloro-5,6-dimethyl)-phenyl]-5-methyl-pyrrolidine-2,4-dione and dimethylcarbamoyl chloride are used as starting materials, the course of the reaction can be represented by the following scheme:

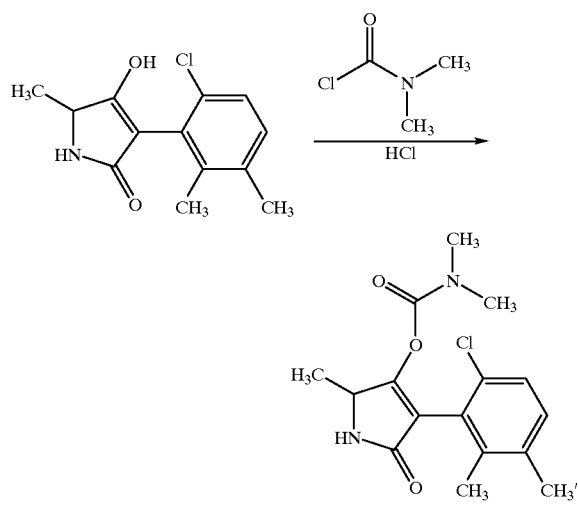

The compounds of the formula (II)

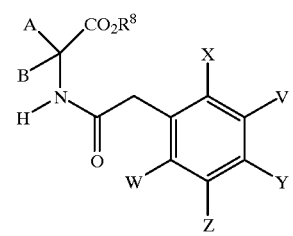

in which
A, B, V, W, X, Y, Z and $R^8$ have the meanings given above,
needed as starting substances in process (A) according to the invention are novel.
The acylamino acid esters of the formula (II) are obtained, for example, when amino acid derivatives of the formula (XIX)

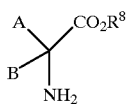
(XIX)

in which

A, B and $R^8$ are each as defined above, are acylated using substituted phenylacetyl halides of the formula (XX)

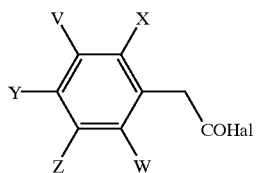
(XX)

in which
V, W, X, Y and Z are each as defined above and
Hal represents chlorine or bromine, (Chem. Reviews 52 237–416 (1953); Bhattacharya, Indian J. Chem. 6, 341–5, 1968)

or when acylamino acids of the formula (XXI)

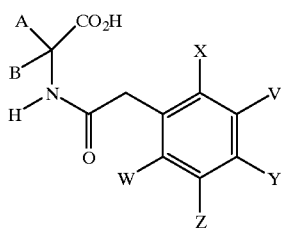
(XXI)

in which
A, B, V, W, X, Y and Z are each as defined above,
are esterified (Chem. Ind. (London) 1568 (1968)).

The compounds of the formula (XXI)

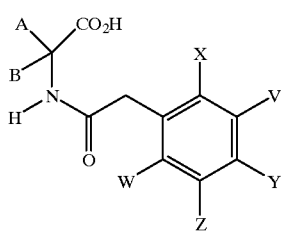
(XXI)

in which

A, B, V, W, X, Y and Z are each as defined above, are novel

The compounds of the formula (XXI) are obtained when amino acids of the formula (XXII)

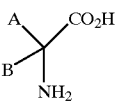
(XXII)

in which

A and B are each defined as above, are acylated using substituted phenylacetyl halides of the formula (XX)

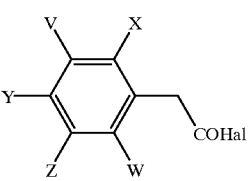
(XX)

in which

V, W, X, Y and Z are each as defined above and

Hal represents chlorine or bromine, according to Schotten-Baumann (Organikum, VEB Deutscher Verlag der Wissenschaften, Berlin 1977, p. 505).

Some of the compounds of the formula (XX) are novel and can be prepared by known methods.

The compounds of the formula (XX) are obtained, for example, by reacting substituted phenylacetic acids of the formula (XXIII)

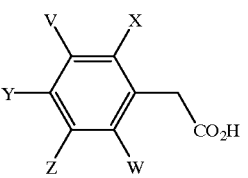
(XXIII)

in which

V, W, X, Y and Z are each as defined above, with halogenating agents (e.g. thionyl chloride, thionyl bromide, oxalyl chloride, phosgene, phosphorus trichloride, phosphorus tribromide or phosphorus pentachloride), if appropriate in the presence of a diluent (e.g. optionally chlorinated aliphatic or aromatic hydrocarbons such as toluene or methylene chloride) at temperatures from −20° C. to 150° C., preferably from −10° C. to 100° C.

Some of the compounds of the formula (XXIII) are novel, they can be prepared by methods known from the literature (Organikum 15th edition, p. 533, VEB Deutscher Verlag der Wissenschaften, Berlin 1977). The compounds of the formula (XXIII) are obtained, for example, by hydrolysing substituted phenylacetic acid esters of the formula (XXIV)

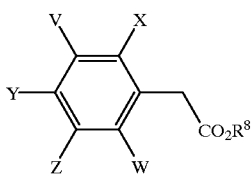
(XXIV)

in which

V, W, X, Y, Z and $R^8$ are each as defined above,
at temperatures between 0° C. and 150° C., preferably between 20° C. and 100° C., in the presence of an acid (e.g. of an inorganic acid such as hydrochloric acid) or of a base (e.g. of an alkali metal hydroxide such as sodium or potassium hydroxide) and, if appropriate, of a diluent (e.g. of an aqueous alcohol such as methanol or ethanol).

Some of the compounds of the formula (XXIV) are novel, they can be prepared by methods known in principle.

The compounds of the formula (XXIV) are obtained, for example, by reacting substituted 1,1,1-trichloro-2-phenylethanes of the formula (XXV)

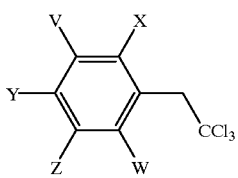
(XXV)

in which

V, W, X, Y and Z are each as defined above,
first with alkoxides (e.g. alkali metal alkoxides such as sodium methoxide or sodium ethoxide) in the presence of a diluent (e.g. the alcohol derived from the alkoxide) at temperatures between 0° C. and 150° C., preferably between 20° C. and 120° C., and then reacting with an acid (preferably an inorganic acid, e.g. sulphuric acid) at temperatures between –20° C. and 150° C., preferably 0° C. and 100° C. (cf. DE-33 14 249).

Some of the compounds of the formula (XXV) are novel, they can be prepared by methods known in principle.

The compounds of the formula (XXV) are obtained, for example, when anilines of the formula (XXVI)

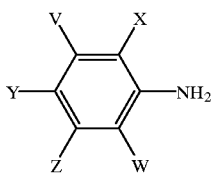
(XXVI)

in which

V, W, X, Y and Z are each as defined above,
are reacted with vinylidene chloride ($CH_2=CCl_2$) in the presence of an alkyl nitrite of the formula (XXVII)

$$R^{21}-ONO \quad (XXVII)$$

in which $R^{21}$ represents alkyl, preferably $C_1-C_6$-alkyl, in the presence of copper(II) chloride and if appropriate in the presence of a diluent (e.g. of an aliphatic nitrile such as acetonitrile) at a temperature of –20° C. to 80° C., preferably 0° C. to 60° C.

Some of the compounds of the formula (XXVI) are known compounds, or they can be prepared by methods known in principle. The compounds of the formula (XXVII) are known compounds of organic chemistry. Copper(II) chloride and vinylidene chloride have long been known and are commercially available.

The compounds of the formulae (XIX) and (XXII) are known in some cases and/or can be prepared by known processes (see, for example, Compagnon, Miocque, Ann. Chim. (Paris) [14] 5, p. 11–22, 23–27 (1970)).

The substituted cyclic aminocarboxylic acids of the formula (XXIIa), in which A and B form a ring, are in general obtainable by the Bucherer-Bergs synthesis or by the Strecker synthesis and are in each case obtained here in different isomeric forms. Thus, according to the conditions of the Bucherer-Bergs synthesis mainly the isomers (in the following designated as β for the sake of simplicity) in which the radicals R and the carboxyl group are equatorial are obtained, while according to the conditions of the Strecker synthesis mainly the isomers (in the following designated as α for the sake of simplicity) are obtained in which the amino group and the radicals R are equatorial.

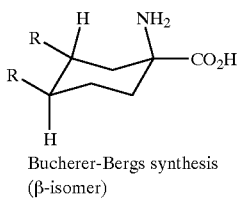 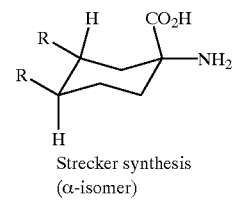

Bucherer-Bergs synthesis (β-isomer)  Strecker synthesis (α-isomer)

(L. Munday, J. Chem. Soc. 4372 (1961); J. T. Eward, C. Jitrangeri, Can. J. Chem. 53, 3339 (1975)).

Furthermore, the starting materials of the formula (II)

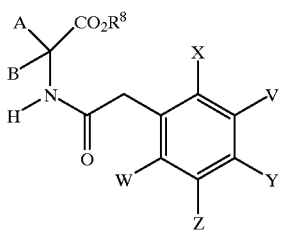
(II)

in which

A, B, V, W X, Y, Z and $R^8$ are each as defined above, used in the above process (A) can be prepared by reacting aminonitriles of the formula (XXVIII)

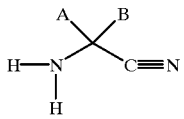
(XXVIII)

in which

A and B are as defined above, with substituted phenylacetyl halides of the formula (XX)

(XX)

in which

V, W, X, Y, Z and Hal are each as defined above,
to give compounds of the formula (XXIX)

(XXIX)

in which

A, B, V, W, X, Y and Z are each as defined above,
and these are then subjected to an acidic alcoholysis.

The compounds of the formula (XXIX) are also novel.

The compounds of the formula (III)

(III)

in which

A, B, V, W, X, Y, Z and $R^8$ are each as defined above,
needed as starting materials in process (B) according to the invention are novel.

They can be prepared in a simple manner by methods known in principle.

The compounds of the formula (III) are obtained, for example, when 2-hydroxycarboxylic acid esters of the formula (XXX)

(XXX)

in which

A, B and $R^8$ are each as defined above,
are acylated using substituted phenylacetyl halides of the formula (XX)

(XX)

in which

V, W, X, Y, Z and Hal are each as defined above,
(Chem. Reviews 52, 237–416 (1953)).

Furthermore, compounds of the formula (III) are obtained when substituted phenylacetic acids of the formula (XXIII)

(XXIII)

in which

V, W, X, Y and Z are each as defined above,
are alkylated using α-halogenocarboxylic acid esters of the formula (XXXI)

(XXXI)

in which

A, B and $R^8$ are each as defined above and

Hal represents chlorine or bromine.

The compounds of the formula (XXXI) are commercially available.

The compounds of the formula (IV)

(IV)

in which

A, B, T, V, W, X, Y, Z and $R^8$ are each as defined above,
to needed as starting substances in the above process (C) are novel.

They can be prepared by methods known in principle.

The compounds of the formula (IV) are obtained, for example, when substituted phenylacetic acid esters of the formula (XXIV)

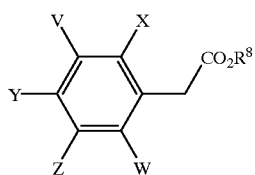

in which

V, W, X, Y, $R^8$ and Z are each as defined above, are acylated using 2-benzylthio-carbonyl halides of the formula (XXXII)

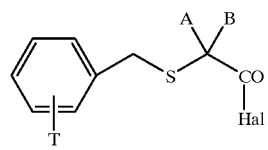

in which

A, B and T are each as defined above and

Hal represents halogen (in particular chlorine or bromine), in the presence of strong bases (see, for example, M. S. Chambers, E. J. Thomas, D. J. Williams, J. Chem. Soc. Chem. Commun., (1987), 1228).

The benzylthio-carbonyl halides of the formula (XXXII) are known in some cases and/or can be prepared by known methods (J. Antibiotics (1983), 26, 1589).

The halogenocarbonylketenes of the formula (VI) needed as starting materials in process (D) are novel. They can be prepared in a simple manner by methods known in principle (cf., for example, Org. Prep. Proced. Int., 7, (4), 155–158, 1975 and DE 1 945 703). The compounds of the formula (VI)

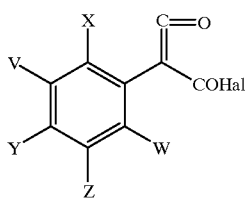

in which

V, W, X, Y and Z are each as defined above and

Hal represents chlorine or bromine, are obtained when substituted phenylmalonic acids of the formula (XXXIII)

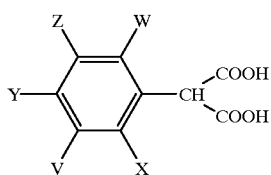

in which

V, W, X, Y and Z are each as defined above, are reacted with acid halides, for example thionyl chloride, phosphorus(V) chloride, phosphorus(III) chloride, oxalyl chloride, phosgene or thionyl bromide, if appropriate in the presence of catalysts, for example diethylformamide, methylsterylformamide or triphenylphosphine and if appropriate in the presence of bases, e.g. pyridine or triethylamine, at a temperature between −20° C. and 200° C., preferably between 0° C. and 150° C.

The substituted phenylmalonic acids of the formula (XXXIII) are novel. However, they can be prepared by known processes in a simple manner (cf., for example Organikum, VEB Deutscher Verlag der Wissenschaften, Berlin 1977, p. 517 ff), for example by saponification of substituted phenylmalonic esters of the formula (XXXIV)

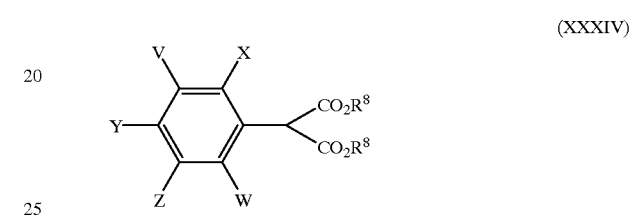

in which

V, W, X, Y, Z and $R^8$ are each as defined above.

The carbonyl compounds of the formula (V) or their silyl enol ethers of the formula (Va)

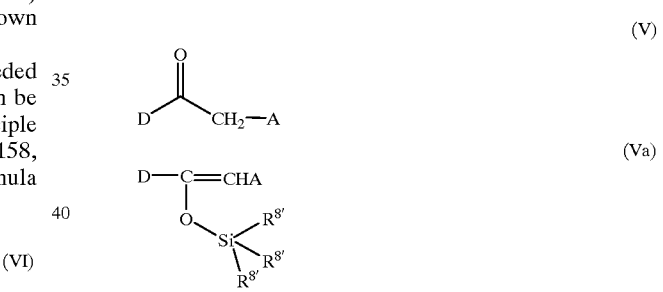

in which

A, D and $R^{8'}$ are each as defined above, needed as starting materials for process (E) according to the invention are compounds which are commercially available, generally known or accessible by known processes.

The preparation of the ketene acid chlorides of the formula (VI) needed as starting materials for carrying out process (E) according to the invention has already been described for process (D) according to the invention. The thioamides of the formula (VII)

in which

A is as defined above, needed for carrying out process (E) according to the invention are compounds which are generally known in organic chemistry.

The malonic acid esters of the formula (XXXIV)

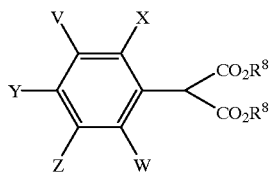

(XXXIV)

in which
$R^8$, V, W, X, Y and Z are each as defined above,
are novel and can be prepared by generally known methods of organic chemistry (cf., for example, Tetrahedron Lett. 27, 2763 (1986) and Organikum VEB Deutscher Verlag der Wissenschaften, Berlin 1977, p. 587 ff.).

The acid halides of the formula (VIII), carboxylic anhydrides of the formula (IX), chloroformic acid esters or chloroformic acid thioesters of the formula (X), chloromonothioformic acid esters or chlorodithioformic acid esters of the formula (XI), alkyl halides of the formula (XII), sulphonyl chlorides of the formula (XIII), phosphorus compounds of the formula (XIV) and metal hydroxides, metal alkoxides or amines of the formula (XV) and (XVI) and isocyanates of the formula (XVII) and carbamoyl chlorides of the formula (XVIII) additionally needed as starting substances for carrying out processes (F), (G), (H), (I), (J), (K) and (L) according to the invention are generally known compounds of organic or inorganic chemistry.

The compounds of the formulae (V), (VII) to (XVIII), (XIX), (XXII), (XXVIII), (XXX), (XXXI), (XXXII), (XXXIII) and (XXXIV) are moreover disclosed in the patent applications cited at the outset and/or can be prepared by the methods given there.

Process (A) is characterized in that compounds of the formula (II), in which A, B, V, W, X, Y, Z and $R^8$ are each as defined above, are subjected to an intramolecular condensation in the presence of a diluent and in the presence of a base.

Diluents employed in process (A) according to the invention can be all organic solvents which are inert to the reaction participants. Those preferably utilizable are hydrocarbons, such as toluene and xylene, further ethers, such as dibutyl ether, tetrahydrofuran, dioxane, glycol dimethyl ether and diglycol dimethyl ether, additionally polar solvents, such as dimethyl sulphoxide, sulpholane, dimethylformamide and N-methyl-pyrrolidone, and also alcohols such as methanol, ethanol, propanol, iso-propanol, butanol, iso-butanol and tert-butanol.

Suitable bases (deprotonating agents) employed in carrying out process (A) according to the invention can be all customary proton acceptors. Those preferably utilizable are alkali metal and alkaline earth metal oxides, hydroxides and carbonates, such as sodium hydroxide, potassium hydroxide, magnesium oxide, calcium oxide, sodium carbonate, potassium carbonate and calcium carbonate, each of which can also be employed in the presence of phase-transfer catalysts, e.g. triethylbenzylammonium chloride, tetrabutylammonium bromide, Adogen 464 (=methyltrialkyl($C_8$–$C_{10}$) ammonium chloride) or TDA 1 (=tris-(methoxyethoxyethyl)-amine). Alkali metals such as sodium or potassium can furthermore be used. Alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can further be employed.

When carrying out process (A) according to the invention, the reaction temperature can be varied within a relatively wide range. In general, the reaction is carried out at temperatures between −50° C. and 250° C., preferably between −30° C. and 150° C.

Process (A) according to the invention is in general carried out under atmospheric pressure.

When carrying out process (A) according to the invention, the reaction component of the formula (II) and the deprotonating base are in general employed in equimolar to approximately double equimolar amounts. However, it is also possible to use one component or the other in a relatively large excess (up to 3 mol).

Process (B) is characterized in that compounds of the formula (III), in which A, B, V, W, X, Y, Z and $R^8$ are each as defined above, are condensed intramolecularly in the presence of a diluent and in the presence of a base.

The diluents employed in process (B) according to the invention can be all organic solvents which are inert to the reaction participants. Those preferably utilizable are hydrocarbons, such as toluene and xylene, furthermore ethers, such as dibutyl ether, tetrahydrofuran, dioxane, glycol dimethyl ether and diglycol dimethyl ether, and additionally polar solvents, such as dimethyl sulphoxide, sulpholane, dimethylformamide and N-methyl-pyrrolidone. Alcohols such as methanol, ethanol, propanol, iso-propanol, butanol, iso-butanol and tert-butanol can furthermore be employed.

The bases (deprotonating agents) employed in carrying out process (B) according to the invention can be all customary proton acceptors. Those preferably utilizable are alkali metal and alkaline earth metal oxides, hydroxides and carbonates, such as sodium hydroxide, potassium hydroxide, magnesium oxide, calcium oxide, sodium carbonate, potassium carbonate and calcium carbonate, each of which can also be employed in the presence of phase-transfer catalysts, e.g. triethylbenzylammonium chloride, tetrabutylammonium bromide, Adogen 464 (=methyltrialkyl($C_8$–$C_{10}$) ammonium chloride) or TDA 1 (=tris-(methoxyethoxyethyl)-amine). Alkali metals such as sodium or potassium can furthermore be used. Alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can additionally also be employed.

When carrying out process (B) according to the invention, the reaction temperature can be varied within a relatively wide range. In general, the reaction is carried out at temperatures between −50° C. and 250° C., preferably between −30° C. and 150° C.

Process (B) according to the invention is in general carried out under atmospheric pressure.

When carrying out process (B) according to the invention, the reaction components of the formula (III) and the deprotonating bases are in general employed in approximately equimolar amounts. However, it is also possible to use one component or the other in a relatively large excess (up to 3 mol).

Process (C) is characterized in that compounds of the formula (IV), in which A, B, T, V, W, X, Y, Z and $R^8$ are each as defined above, are cyclized intramolecularly in the presence of an acid and if appropriate in the presence of a diluent.

Diluents which can be employed in process (C) according to the invention are all organic solvents which are inert to the reaction participants. Those preferably utilizable are hydrocarbons, such as toluene and xylene, further halogenated hydrocarbons such as dichloromethane, chloroform, ethylene chloride, chlorobenzene, dichlorobenzene, additionally polar solvents, such as dimethyl sulphoxide, sulpholane, dimethylformamide and N-methyl-pyrrolidone. Alcohols such as methanol, ethanol, propanol, iso-propanol, butanol, isobutanol, tert-butanol can furthermore be employed.

The acid employed can optionally also be used as a diluent.

Acids which can be employed in process (C) according to the invention are all customary inorganic and organic acids, e.g. hydrohalic acids, sulphuric acid, alkyl-, aryl- and haloalkylsulphonic acids; halogenated alkylcarboxylic acids, e.g. trifluoroacetic acid, are used in particular.

When carrying out process (C) according to the invention, the reaction temperature can be varied within a relatively wide range. In general, the reaction is carried out at temperatures between −30° C. and 250° C., preferably between 0° C. and 150° C.

Process (C) according to the invention is in general carried out under atmospheric pressure.

When carrying out process (C) according to the invention, the reaction components of the formulae (IV) and the acid are employed, for example, in equimolar amounts. However, it is optionally also possible to employ the acid in catalytic amounts.

Process (D) according to the invention is characterized in that carbonyl compounds of the formula (V) or their silyl enol ethers of the formula (Va) in which A and B are each as defined above are reacted with ketene acid halides of the formula (VI) in which V, W, X, Y and Z are each as defined above, if appropriate in the presence of a diluent and if appropriate in the presence of an acid acceptor.

Diluents which can be employed in process (D) according to the invention are all organic solvents which are inert to the reaction participants. Those preferably utilizable are hydrocarbons, such as o-dichlorobenzene, tetralin, toluene and xylene, furthermore ethers, such as dibutyl ether, glycol dimethyl ether and diglycol dimethyl ether, and additionally polar solvents, such as dimethyl sulphoxide, sulpholane, dimethylformamide or N-methyl-pyrrolidone.

Acid acceptors which can be used when carrying out process (D) according to the invention are all customary acid acceptors.

Those preferably utilizable are tertiary amines, such as triethylamine, pyridine, diazabicyclooctane (DABCO), diazabicycloundecene (DBU), diazabicyclononene (DBN), Hünig base or N,N-dimethyl-aniline.

When carrying out process (D) according to the invention, the reaction temperature can be varied within a relatively wide range. The reaction is expediently carried out at temperatures between 0° C. and 250° C., preferably between 50° C. and 220° C.

Process (D) according to the invention is preferably carried out under atmospheric pressure.

When carrying out process (D) according to the invention, the reaction components of the formulae (V) and (VI) and, if appropriate, the acid acceptor are in general employed in approximately equimolar amounts. However, it is also possible to use one component or the other in a relatively large excess (up to 5 mol).

Process (E) according to the invention is characterized in that thioamides of the formula (VII) in which A is as defined above are reacted with ketene acid halides of the formula (VI), in which V, W, X, Y and Z are as defined above, if appropriate in the presence of a diluent and if appropriate in the presence of an acid acceptor.

Diluents which can be employed in process variant (E) according to the invention are all inert organic solvents. Those preferably utilizable are hydrocarbons, such as o-dichlorobenzene, tetralin, toluene and xylene, furthermore ethers, such as dibutyl ether, glycol dimethyl ether and diglycol dimethyl ether, and additionally polar solvents, such as dimethyl sulphoxide, sulpholane, dimethylformamide and N-methyl-pyrrolidone.

Acid acceptors which can be used in carrying out process (E) according to the invention are all customary acid acceptors.

Those preferably utilizable are tertiary amines, such as triethylamine, pyridine, diazabicyclooctane (DABCO), diazabicycloundecane (DBU), diazabicyclononene (DBN), Hünig base and N,N-dimethyl-aniline.

When carrying out process (E) according to the invention, the reaction temperature can be varied within a relatively wide range. The reaction is expediently carried out at temperatures between 0° C. and 250° C., preferably between 20° C. and 220° C.

Process (E) according to the invention is expediently carried out under atmospheric pressure.

When carrying out process (E) according to the invention, the reaction components of the formulae (VII) and (VI) and, if appropriate, the acid acceptors are in general employed in approximately equimolar amounts. However, it is also possible to use one component or the other in a relatively large excess (up to 5 mol).

Process (Fα) is characterized in that compounds of the formulae (I-1-a) to (I-5-a) are in each case reacted with carboxylic acid halides of the formula (VIII), if appropriate in the presence of a diluent and if appropriate in the presence of an acid-binding agent.

Diluents which can be employed in process (Fα) according to the invention are all solvents inert to the acid halides. Those preferably utilizable are hydrocarbons, such as benzine, benzene, toluene, xylene and tetralin, furthermore halogenohydrocarbons, such as methylene chloride, chloroform, carbon tetrachloride, chlorobenzene and o-dichlorobenzene, additionally ketones, such as acetone and methyl isopropyl ketone, furthermore ethers, such as diethyl ether, tetrahydrofuran and dioxane, moreover carboxylic acid esters, such as ethyl acetate, and also strongly polar solvents, such as dimethylformamide, dimethyl sulphoxide and sulpholane. If the stability to hydrolysis of the acid halide permits, the reaction can also be carried out in the presence of water.

In the reaction by process (Fα) according to the invention, suitable acid-binding agents are all customary acid acceptors. Those preferably utilizable are tertiary amines, such as triethylamine, pyridine, diazabicyclooctane (DABCO), diazabicycloundecene (DBU), diazabicyclononene (DBN), Hünig base and N,N-dimethyl-aniline, furthermore alkaline earth metal oxides, such as magnesium and calcium oxide, additionally alkali metal and alkaline earth metal carbonates, such as sodium carbonate, potassium carbonate and calcium carbonate and also alkali metal hydroxides such as sodium hydroxide and potassium hydroxide.

In process (Fα) according to the invention, the reaction temperature can be varied within a relatively wide range. In general, the reaction is carried out at temperatures between −20° C. and +150° C., preferably between 0° C. and 100° C.

When carrying out process (Fα) according to the invention, the starting substances of the formulae (I-1-a) to (I-5-a) and the carboxylic acid halide of the formula (VIII) are in general each used in approximately equivalent amounts. However, it is also possible to employ the carboxylic acid halide in a relatively large excess (up to 5 mol). Work-up is carried out according to customary methods.

Process (Fβ) is characterized in that compounds of the formulae (I-1-a) to (I-5-a) are each reacted with carboxylic anhydrides of the formula (IX), if appropriate in the presence of a diluent and if appropriate in the presence of an acid-binding agent.

Diluents which can be used in process (Fβ) according to the invention are preferably those diluents which are also suitable when using acid halides. Otherwise, a carboxylic anhydride employed in excess can also simultaneously function as diluent.

Possible acid-binding agents optionally added in process (Fβ) are preferably those acid-binding agents which are also suitable when using acid halides.

The reaction temperature in process (Fβ) according to the invention can be varied within a relatively wide range. In general, the reaction is carried out at temperatures between $-20°$ C. and $+150°$ C., preferably between $0°$ C. and $100°$ C.

When carrying out process (Fβ) according to the invention, the starting substances of the formulae (I-1-a) to (I-5-a) and the carboxylic anhydride of the formula (XI) are in (general used in approximately equivalent amounts in each case. However, it is also possible to employ the carboxylic anhydride in a relatively large excess (up to 5 mol). Work-up is carried out according to customary methods.

In general, a procedure is used in which diluent and carboxylic anhydride present in excess and also the resulting carboxylic acid are removed by distillation or by washing with an organic solvent or with water.

Process (G) is characterized in that compounds of the formulae (I-1-a) to (I-5-a) are each reacted with chloroformic acid esters or chloroformic acid thioesters of the formula (X), if appropriate in the presence of a diluent and if appropriate in the presence of an acid-binding agent.

Possible acid-binding agents in process (G) according to the invention are all customary acid acceptors. Those preferably utilizable are tertiary amines, such as triethylamine, pyridine, DABCO, DBU, DBA, Huinig base and N,N-dimethylaniline, furthermore alkaline earth metal oxides, such as magnesium and calcium oxide, additionally alkali metal and alkaline earth metal carbonates, such as sodium carbonate, potassium carbonate and calcium carbonate and also alkali metal hydroxides such as sodium hydroxide and potassium hydroxide.

Diluents which can be employed in process (G) according to the invention are all solvents which are inert to the chloroformic acid esters or chloroformic acid thioesters. Those preferably utilizable are hydrocarbons, such as benzine, benzene, toluene, xylene and tetralin, further halogenohydrocarbons, such as methylene chloride, chloroform, carbon tetrachloride, chlorobenzene and o-dichlorobenzene, additionally ketones, such as acetone and methyl isopropyl ketone, furthermore ethers, such as diethyl ether, tetrahydrofuran and dioxane, moreover carboxylic acid esters, such as ethyl acetate, furthermore nitriles, such as acetonitrile, and also strongly polar solvents, such as dimethylformamide, dimethyl sulphoxide and sulpholane.

When carrying out process (G) according to the invention, the reaction temperature can be varied within a relatively wide range. The reaction temperature is in (general between $-20°$ C. and $+100°$ C., preferably between $0°$ C. and $50°$ C.

Process (G) according to the invention is in general carried out under atmospheric pressure.

When carrying out process (G) according to the invention, the starting substances of the formulae (I-1-a) to (I-5-a) and the appropriate chloroformic acid esters or chloroformic acid thioesters of the formula (X) are in general each used in approximately equivalent amounts. However, it is also possible to employ one component or the other in a relatively large excess (up to 2 mol). Work-up is carried out according to customary methods. In general, a procedure is used in which precipitated salts which are deposited are removed and the reaction mixture which remains is concentrated by stripping off the diluent.

Process (H) according to the invention is characterized in that compounds of the formulae (I-1-a) to (I-5-a) are each reacted with (Hα) compounds of the formula (XI) in the presence of a diluent and if appropriate in the presence of an acid-binding, agent or (Hβ) carbon disulphide and then with alkyl halides of the formula (XII), if appropriate in the presence of a diluent and if appropriate in the presence of a base.

In preparation process (Hα), about 1 mol of chloromonothioformic acid ester or chlorodithioformic acid ester of the formula (XI) is reacted at 0 to $120°$ C., preferably at 20 to $60°$ C., per mole of starting compound of the formulae (I-1-a) to (I-5-a).

Possible diluents optionally added are all inert polar organic solvents, such as ethers, amides, sulphones, sulphoxides, but also halogenoalkanes.

Dimethyl sulphoxide, tetrahydrofuran, dimethylformamide or methylene chloride are preferably employed.

If, in a preferred embodiment, the enolate salt of the compounds (I-1-a) to (I-5-a) is prepared by addition of strong deprotonating agents, e.g. sodium hydride or potassium tertiary butoxide, the further addition of acid-binding agents can be dispensed with.

If acid-binding agents are employed, customary inorganic or organic bases are suitable; sodium hydroxide, sodium carbonate, potassium carbonate, pyridine and triethiylamine may be mentioned by way of example.

The reaction can be carried out at atmospheric pressure or at elevated pressure; it is preferably carried out at normal pressure. Work-up takes place according to customary methods.

In preparation process (Hβ), the equimolar amount or an excess of carbon disulphide is in each case added per mole of starting compounds of the formulae (I-1-a) to (I-5-a). The reaction is in this case preferably carried out at temperatures from 0 to $50°$ C. and in particular at 20 to $30°$ C.

Often it is expedient first to prepare the corresponding salt from the compounds of the formulae (I-1-a) to (I-5-a) by addition of a base (e.g. potassium tertiary to butoxide or sodium hydride). The compounds (I-1-a) to (I-5-a) are each reacted with carbon disulphide until the formation of the intermediate compound is complete, e.g. after stirring at room temperature for several hours.

Bases which can be employed in process (HO are all customary proton acceptors. Those preferably utilizable are alkali metal hydrides, alkali metal alkoxides, alkali metal or alkaline earth metal carbonates or hydrogen carbonates or nitrogen bases. Those which may be mentioned, for example, are sodium hydride, sodium methoxide, sodium hydroxide, calcium hydroxide, potassium carbonate, sodium hydrogen carbonate, triethylamine, dibenzylamine, diisopropylamine, pyridine, quinoline, diazabicyclooctane (DABCO), diazabicyclononene (DBN) and diazabicycloundecene (DBU).

Diluents which can be used in this process are all customary solvents.

Those preferably utilizable are aromatic hydrocarbons such as benzene or toluene, alcohols such as methanol, ethanol, isopropanol or ethylene glycol, nitrites such as acetonitrile, ethers such as tetrahydrofuran or dioxane, amides such as dimethylformamide or other polar solvents such as dimethyl sulphoxide or sulpholane.

Further reaction with the alkyl halide of the formula (XII) is preferably carried out at 0 to 70° C. and in particular at 20 to 50° C. In this case, at least the equimolar amount of alkyl halide is employed.

The reaction is carried out at atmospheric pressure or at elevated pressure, preferably at atmospheric pressure.

Work-up is in turn carried out according to customary methods.

Process (I) according to the invention is characterized in that compounds of the formulae (I-1-a) to (I-5-a) are each reacted with sulphonyl chlorides of the formula (XIII), if appropriate in the presence of a diluent and if appropriate in the presence of an acid-binding agent.

In preparation process (1), about 1 mol of sulphonyl chloride of the formula (XIII) is reacted at −20 to 150° C., preferably at 0 to 70° C., per mole of starting compound of the formula (I-1-a to I-5-a).

Process (I) is preferably carried out in the presence of a diluent.

Possible diluents are all inert polar organic solvents, such as ethers, amides, ketones, carboxylic acid esters, nitriles, sulphones, sulphoxides or halogenated hydrocarbons such as methylene chloride.

Dimethyl sulphoxide, tetrahydrofuran, dimethylformamide and methylene chloride are preferably employed.

If, in a preferred embodiment, the enolate salt of the compounds (I-1-a) to (I-5-a) is prepared by addition of strong deprotonating agents (e.g. sodium hydride or potassium tertiary butoxide), the further addition of acid-binding agents can be dispensed with.

If acid-binding agents are employed, customary inorganic or organic bases are suitable; those which may be mentioned by way of example are sodium hydroxide, sodium carbonate, potassium carbonate, pyridine and triethylamine.

The reaction can be carried out at atmospheric pressure or at elevated pressure, preferably it is carried out at atmospheric pressure. Work-up takes place according to customary methods.

Process (J) according to the invention is characterized in that compounds of the formulae (I-1-a) to (I-5-a) are each reacted with phosphorus compounds of the formula (XIV), if appropriate in the presence of a diluent and if appropriate in the presence of an acid-binding agent.

In preparation process (J), to obtain compounds of the formulae (I-1-e) to (I-5-e), 1 to 2, preferably 1 to 1.3, mol of the phosphorus compound of the formula (XIV) are reacted at temperatures between −40° C. and 150° C., preferably between −10 and 110° C., relative to 1 mol of the compounds (I-1-a) to (I-5-a).

Process (J) is preferably carried out in the presence of a diluent.

Possible diluents are all inert, polar organic solvents, such as ethers, carboxylic acid esters, halogenated hydrocarbons, ketones, amides, nitrites, sulphones, sulphoxides etc.

Acetonitrile, dimethyl sulphoxide, tetrahydrofuran, dimethylformamide and methylene chloride are preferably employed.

Possible acid-binding agents optionally added are customary inorganic or organic bases such as hydroxides, carbonates or amines. Those which may be mentioned by way of example are sodium hydroxide, sodium carbonate, potassium carbonate, pyridine and triethylamine.

The reaction can be carried out at atmospheric pressure or at elevated pressure, preferably at atmospheric pressure.

Work-up takes place according to customary methods of organic chemistry. The final products are preferably purified by crystallization, chromatographic purification or by so-called "incipient distillation", i.e. removal of the volatile constituents in vacuo.

Process (K) is characterized in that compounds of the formulae (I-1-a) to (I-5-a) are each reacted with metal hydroxides or metal alkoxides of the formula (XV) or amines of the formula (XVI), if appropriate in the presence of a diluent.

Diluents which can be employed in process (K) according to the invention are preferably ethers such as tetrahydrofuran, dioxane, diethyl ether or else alcohols such as methanol, ethanol, isopropanol, but also water. Process (K) according to the invention is in general carried out under atmospheric pressure. The reaction temperature is in general between −20° C. and 100° C., preferably between 0° C. and 50° C.

Process (L) according to the invention is characterized in that compounds of the formulae (I-1-a) to (I-5-a) are each reacted with (Lα) compounds of the formula (XVII), if appropriate in the presence of a diluent and if appropriate in the presence of a catalyst, or (Lβ) with compounds of the formula (XVIII), if appropriate in the presence of a diluent and if appropriate in the presence of an acid-binding agent.

In preparation process (Lα), about 1 mol of isocyanate of the formula (XVII) is reacted at 0 to 100° C., preferably at 20 to 50° C., per mole of starting compound of the formulae (I-1-a) to (I-5-a).

Process (Lα) is preferably carried out in the presence of a diluent.

Possible diluents are all inert organic solvents, such as aromatic hydrocarbons, halogenated hydrocarbons, ethers, amides, nitriles, sulphones or sulphoxides.

Catalysts can optionally be added to accelerate the reaction. The catalysts employed can very advantageously be organotin compounds, e.g. dibutyltin dilaurate.

The reaction is preferably carried out at atmospheric pressure.

In preparation process (Lβ), about 1 mol of carbamoyl chloride of the formula (XVIII) is reacted at 0 to 150° C., preferably at 20 to 70° C., per mole of starting compound of the formulae (I-1-a) to (I-5-a).

Possible diluents optionally added are all inert polar organic solvents, such as ethers, carboxylic acid esters, nitrites, ketones, amides, sulphones, sulphoxides or halogenated hydrocarbons.

Dimethyl sulphoxide, tetrahydrofuran, dimethylformamide or methylene chloride are preferably employed.

If, in a preferred embodiment, the enolate salt of the compound (I-1-a) to (I-5-a) is prepared by addition of strong deprotonating agents (e.g. sodium hydride or potassium tertiary butoxide), the further addition of acid-binding agents can be dispensed with.

If acid-binding agents are employed, customary inorganic or organic bases are suitable; those which may be mentioned by way of example are sodium hydroxide, sodium carbonate, potassium carbonate, triethylamine or pyridine.

The reaction can be carried out at atmospheric pressure or at elevated pressure, preferably at atmospheric pressure. Work-up takes place according to customary methods.

The active compounds are suitable for controlling animal pests, preferably arthropods and nematodes, in particular insects and arachnida, which are encountered in agriculture, in forestry, in the protection of stored products and of materials, and in the hygiene field. They are active against normally sensitive and resistant species and against all or some stages of development. The above-mentioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus zarundinis, Macrosiphum avenae, Myzus* spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon soistitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds according to the invention are distinguished by a high insecticidal and acaricidal activity.

They can be used to particularly good effect for controlling insects which are injurious to plants, such as, for example, against the larvae of the mustard beetle (*Phaedon cochleariae*), against the larvae of the green rice leaf hopper (*Nephotettix cincticeps*) or against the caterpillars of the cabbage moth (*Plutelia maculipennis*).

The active compounds according to the invention can furthermore be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The dosages of the active compounds according to the invention necessary for controlling weeds are betweeen 0.001 and 10 kg/ha, preferably between 0.005 and 5 kg/ha.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cycnodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for controlling weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective control of weeds in annual cultures.

The active compounds according to the invention are very highly suitable for the selective control of monocotyledon weeds in dicotyledon crops pre- and post-emergence. They can be employed to very good effect for the control of grass weeds, for example in cotton or sugar beet.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable:

for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compound according to the invention can be present in its commercially available formulations and in the use forms prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms.

Examples of particularly advantageous mixture components are the following compounds:

Fungicides:

2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-di-chloro-N-(4-trifluoromethylbenzyl)benzamide; (E)-2-methoxyimino-N-methyl-2-(2-phenoxy-phenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminum, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyidithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulfur and sulfur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichiamide, tricyclazole, tridemorpb, triflumizole, triforine, triticonazole, validamycin A, vinclozolin, zineb, ziram Bactericides:

bronopol, dichlorophen, nitrapyrin, nickel dimetbyidithiocarbamate, kasugamycin, octlillinone, furancarboxylic acid, oxytetracyclin, probenazole, streptomycin, tecloftalam, copper sulphate and other copper preparations.

Insecticides/Acaricides/Nematicides:

abamectin, abamectin, AC 303 630, acephate, acrinathrin, alanycarb, aldicarb, alphamethrin, amitraz, avermectin, AZ 60541, azadirachtin, azinphos A, azinphos M, azocyclotin,

*Bacillus thuringiensis,* bendiocarb, benfuracarb, bensultap, beta-cyfluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthilon, dichlorvos, dicliphos, dicrotophos, diethion, diflubenzuron, dimethoate, dimethylvinphos, dioxathion, disulfoton, edifenphos, emaniectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinani, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, metbacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos,

RH 5992, salithion, sebufos, silafluofen, sulfotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

Herbicides:

for example anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor, dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and loxynil; oxyacetamides such as, for example, mefenacet; sulfonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuronmethyl, triasulfuron and tribenuronmethyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

The active compound according to the invention can furthermore be present in its commercially available formulations and in the use forms prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp., Solenopotes spp.

From the order of the Mallophagida and the sub-orders Amblycerina and Isochnocerina, for example, Trimenopon spp., Menopon spp., Trinoton spp., Bovicola spp., Werneckiella spp., Lepikentron spp., Damalina spp., Trichodectes spp., Felicola spp.

From the order of the Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohifahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta americana, Blattela germanica* and Supella spp.

From the sub-class of the Acaria (Acarida) and the orders of the Meta- and Mesostigmata, for example Argas spp., Ornithodorus spp., Otabius spp., Ixodes spp., Amblyomma spp., Boophilus spp., Dermacentor spp., Haemaphysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

For example, they show an outstanding activity against *Boophilus microplus* and *Lucilia cuprina*.

The active compounds of the formula (I) according to the invention are also suitable for combating arthropods which attack agricultural livestock, such as, for example, cattle, sheep, goats, horses, pigs, donkeys, camels, buffalo, rabbits, chickens, turkeys, ducks, geese, honey bees, other domestic animals, such as, for example, dogs, cats, cage birds, aquarium fish, and so-called experimental animals, such as, for example, hamsters, guinea-pigs, rats and mice. By combating these arthropods, it is intended to reduce mortality and decreased performance (in meat, milk, wool, hides, eggs, honey and the like), so that more economical and simpler animal keeping, is made possible by using the active compounds according to the invention.

In the veterinary sector, the active compounds according to the invention are used in a known manner by enteral administration, for example in the form of tablets, capsules, drinks, drenches, granules, pastes, boluses, the feed-through method, suppositories, by parenteral administration, such as, for example, by means of injections (intramolecular, subcutaneous, intravenous, intraperitoneal and the like), implants, by nasal application, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (1) can be used as formulations (for example powders, emulsions, flowables) which comprise the active compounds in an amount of 1 to 80% by weight, either directly or after dilution by a factor of 100 to 10,000, or they may be used in the form of a chemical bath.

Furthermore, it has been found that the compounds of the formula (1) according to the invention have a potent insecticidal action against insects which destroy industrial materials.

The following insects may be mentioned by way of example and as being preferred, but without any limitation:
P Beetles, such as

*Hylotrupes bajulus, Chlorophorus pilosis, Anobium punctatum, Xestobium rufovillosum, Pulinus pecticomis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis,* Xyleborus spec., Tryptodendron spec., *Apate monachus, Bostrychus capucins, Heterobostrychus brunneus,* Sinoxylon spec., *Dinoderus minutus.*

Dermapterans, such as

*Sirex juvencus, Urocerus gigas, Urocerus gigas taignus, Urocerus augur.*

Termites, scuh as

*Kalotermes flavicollis, Cryptotermes brevis, Heterotermes indicola, Recticulitermes flavipes, Reticulitermes santonensis, Reticulitermes lucifugus, Mastotermes darwiniensis, Zootermopsis nevdensis, Coptotermes formosanus.*

Bristletails, such as

*Lepisma saccharina.*

Industrial materials are to be understood as meaning, in the present context, non-live materials, such as, preferably, synthetic materials, glues, sizes, paper and board, leather, wood and timber products, and paint.

The materials to be very particularly protected against attack by insects are wood and timber products.

Wood and timber products which can be protected by the composition according to the invention or mixtures comprising such a composition are to be understood as meaning, for example, construction timber, wooden beams, railway sleepers, bridge components, jetties, wooden vehicles, boxes, pallets, containers, telephone poles, wood lagging, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents having an evaporation number of above 35 and a flashpoint of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of terpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insectide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ether, esters and the like.

The organochemical binders used within the scope of the present invention are the synthetic resins and/or binding drying oils which are known per se and can be diluted with water and/or are soluble or dispersible or emulsifiable in the organo-chemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% of bitumen or bituminous substances can also be used as binders. In addition, colorants, pigments, water repellents, odour-masking substances and inhibitors or anticorrosives known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzylbutyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluene-sulphonic esters.

Fixatives are chemically based on polyvinyl alkyl ethers, such as, for example, polyvinyl methyl ether, or ketones, such as benzophenone or ethylenebenzophenone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly part of the present application.

Very particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlofluanid, tolylfluanid, 3-iodo-2-propinylbutyl carbamate, N-octyl-isothiazolin-3-one and 4,5-dichloro-N-octylisothiazolin-3-one.

The preparation and the use of the active compounds according to the invention can be seen from the examples which follow.

PREPARATION EXAMPLES

Example (I-1-a-1)

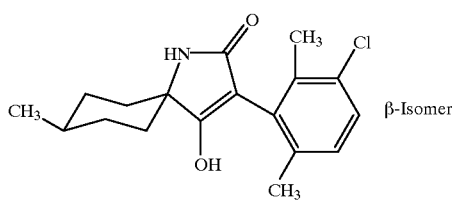

Under reflux, 29.6 g (0.0764 mol) of the compound prepared by the method of Example (II-1) in 160 ml of anhydrous toluene are added dropwise to 22.7 g (0.2 mol) of potassium tert-butoxide in 60 ml of anhydrous tetrahydrofuran (THF), and the mixture is stirred under reflux for 1.5 hours. For work-up, 230 ml of water are added, the aqueous phase is separated off, the toluene phase is extracted with 110 ml of water, and the aqueous phases are combined, washed with toluene and acidified at 10 to 20° C. with conc. HCl to pH 1. The product is filtered off under suction, washed, dried and washed by stirring in methyl tert-butyl ether (MTB) ether/n-hexane.

Yield: 13.7 g (56% of theory), mp.: >220° C.

The compounds of the formula (I-1-a) given below were prepared analogously or in accordance with the general preparation instructions.

TABLE 57

(I-1-a)

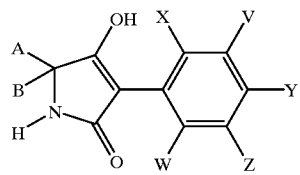

| Ex. No. | V | W | X | Y | Z | A | B | mp. °C. | Isomer |
|---|---|---|---|---|---|---|---|---|---|
| I-1-a-2 | H | CH₃ | CH₃ | H | Cl | —(CH₂)₂—CHOCH₃—(CH₂)₂— | | 219 | β |
| I-1-a-3 | H | CH₃ | CH₃ | CH₃ | CH₃ | —(CH₂)₂—CHCH₃—(CH₂)₂— | | 122 | β |
| I-1-a-4 | H | CH₃ | CH₃ | CH₃ | CH₃ | —(CH₂)₂—CHOCH₃—(CH₂)₂— | | >220 | β |
| I-1-a-5 | H | CH₃ | CH₃ | CH₃ | Br | —(CH₂)₂—CHCH₃—(CH₂)₂— | | 169 | β |
| I-1-a-6 | H | CH₃ | CH₃ | CH₃ | CH₃ | —(CH₂)₂—O—(CH₂)₂— | | >220 | — |
| I-1-a-7 | H | CH₃ | CH₃ | CH₃ | CH₃ | CH₃ | CH₃ | >220 | — |
| I-1-a-8 | H | CH₃ | CH₃ | CH₃ | CH₃ | —(CH₂)₂—CHOC₂H₅—(CH₂)₂— | | 225 | β |
| I-1-a-9 | H | CH₃ | CH₃ | CH₃ | CH₃ | i-C₃H₇ | CH₃ | 185 | — |
| I-1-a-10 | H | CH₃ | CH₃ | CH₃ | Br | —(CH₂)₂—CHOCH₃—(CH₂)₂— | | 180 | β |
| I-1-a-11 | CH₃ | CH₃ | CH₃ | H | CH₃ | —(CH₂)₂—CHCH₃—(CH₂)₂— | | >220 | β |
| I-1-a-12 | CH₃ | CH₃ | CH₃ | H | CH₃ | —(CH₂)₂—CHOCH₃—(CH₂)₂— | | >220 | β |
| I-1-a-13 | CH₃ | CH₃ | H | CH₃ | CH₃ | —(CH₂)₂—CHCH₃—(CH₂)₂— | | >220 | β |
| I-1-a-14 | CH₃ | CH₃ | H | CH₃ | CH₃ | —(CH₂)₂—CHOCH₃—(CH₂)₂— | | >220 | β |
| I-1-a-15 | H | CH₃ | CH₃ | H | Cl | —(CH₂)₂—O—(CH₂)₂— | | >220 | — |
| I-1-a-16 | H | CH₃ | CH₃ | H | Br | —(CH₂)₂—CHCH₃—(CH₂)₂— | | >220 | β |
| I-1-a-17 | H | CH₃ | CH₃ | H | Br | —(CH₂)₂—CHOCH₃—(CH₂)₂— | | >220 | β |
| I-1-a-18 | H | Cl | Cl | H | Br | —(CH₂)₂—CHCH₃—(CH₂)₂— | | >220 | β |
| I-1-a-19 | H | Cl | Cl | H | Br | —(CH₂)₂—CHOCH₃—(CH₂)₂— | | >220 | β |
| I-1-a-20 | H | Br | Br | —(CH₂)₃— | | —(CH₂)₂—CHCH₃—(CH₂)₂— | | >220 | β |
| I-1-a-21 | H | Br | Br | —(CH₂)₃— | | —(CH₂)₂—CHOCH₃—(CH₂)₂— | | >220 | β |
| I-1-a-22 | H | CH₃ | OCH₃ | H | Br | —(CH₂)₂—CHOCH₃—(CH₂)₂— | | >220 | β |
| I-1-a-23 | H | CH₃ | OCH₃ | H | Br | —(CH₂)₂—CHCH₃—(CH₂)₂— | | >220 | β |
| I-1-a-24 | H | CH₃ | CH₃ | CH₃ | CH₃ | —(CH₂)₅— | | 143 | — |
| I-1-a-25 | H | Cl | Cl | Cl | CH₃ | —(CH₂)₂—CHOCH₃—(CH₂)₂— | | >220 | β |
| I-1-a-26 | CH₃ | CH₃ | CH₃ | CH₃ | CH₃ | —(CH₂)₂—CHOCH₃—(CH₂)₂— | | >220 | β |
| I-1-a-27 | H | CH₃ | CH₃ | CH₃ | CH₃ | —(CH₂)₄— | | >225 | |
| I-1-a-28 | H | CH₃ | H | H | CH₃ | —(CH₂)—CHOCH₃—(CH₂)₂— | | >220 | |

TABLE 57-continued

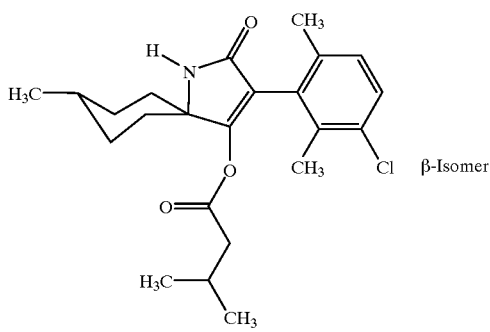

(I-1-a)

| Ex. No. | V | W | X | Y | Z | A | B | mp. °C. | Isomer |
|---|---|---|---|---|---|---|---|---|---|
| I-1-a-29 | CH₃ | CH₃ | CH₃ | CH₃ | CH₃ | —(CH₂)₂—CHCH₃—(CH₂)₂— | | >220 | |
| I-1-a-30 | H | Cl | Cl | Cl | CH₃ | —(CH₂)₂—CHCH₃—(CH₂)₂— | | >220 | |
| I-1-a-31 | H | Br | Br | Br | CH₃ | —(CH₂)₂—CHCH₃—(CH₂)₂— | | >220 | |
| I-1-a-32 | H | Br | Br | Br | CH₃ | —(CH₂)₂—CHOCH₃—(CH₂)₂— | | >220 | |

Example (I-1-b-1)

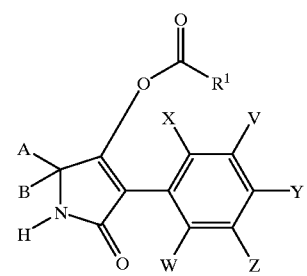

β-Isomer 3.84 g (0.012 mol) of the compound prepared by the method of Example (I-1-a-1) and 2.5 ml (18 mmol) of triethylamine in 70 ml of anhydrous methylene chloride are treated with 2.2 ml (0.18 mol) of isovaleryl chloride in 5 ml of anhydrous methylene chloride at 0 to 10° C., and the mixture is stirred at room temperature until the reaction has ended (TLC check). For work-up, the mixture is washed twice with 50 ml of 0.5 N aqueous sodium hydroxide solution, dried over magnesium sulphate and evaporated. The crude product is recrystallized from MTB ether/n-hexane.

Yield: 1.6 g (33% of theory), mp.: 218° C.

The compounds of the formula (1-b-1) given below are obtained analogously or in accordance with the general preparation instructions:

TABLE 58

(I-1-b)

| Ex. No. | V | W | X | Y | Z | A | B | R¹ | mp. °C. | Isomer |
|---|---|---|---|---|---|---|---|---|---|---|
| I-1-b-2 | H | CH₃ | CH₃ | H | Cl | —(CH₂)₂—CHCH₃—(CH₂)₂— | | i-C₃H₇ | 211 | β |
| I-1-b-3 | H | CH₃ | CH₃ | H | Cl | —(CH₂)₂—CHOCH₃—(CH₂)₂— | | i-C₃H₇ | 215 | β |
| I-1-b-4 | H | CH₃ | CH₃ | CH₃ | CH₃ | —(CH₂)₂—CHCH₃—(CH₂)₂— | | i-C₃H₇ | 217 | β |
| I-1-b-5 | H | CH₃ | CH₃ | CH₃ | CH₃ | —(CH₂)₂—CHCH₃—(CH₂)₂— | | i-C₄H₉ | >220 | β |
| I-1-b-6 | H | CH₃ | CH₃ | CH₃ | Br | —(CH₂)₂—CHCH₃—(CH₂)₂— | | CH₃ | 205 | β |
| I-1-b-7 | H | CH₃ | CH₃ | CH₃ | CH₃ | —(CH₂)₂—CHOCH₃—(CH₂)₂— | | i-C₃H₇ | 194 | β |
| I-1-b-8 | H | CH₃ | CH₃ | CH₃ | CH₃ | —(CH₂)₂—CHOCH₃—(CH₂)₂— | | t-C₄H₉—CH₂ | 186 | β |
| I-1-b-9 | H | CH₃ | CH₃ | CH₃ | Br | —(CH₂)₂—CHOCH₃—(CH₂)₂— | | i-C₃H₇ | 211 | β |
| I-1-b-10 | H | CH₃ | CH₃ | H | Br | —(CH₂)₂—CHCH₃—(CH₂)₂— | | i-C₃H₇ | 205 | β |
| I-1-b-11 | H | Br | Br | —(CH₂)₃— | | —(CH₂)₂—CHCH₃—(CH₂)₂— | | i-C₃H₇ | >220 | β |
| I-1-b-12 | H | CH₃ | OCH₃ | H | Br | —(CH₂)₂—CHOCH₃—(CH₂)₂— | | i-C₃H₇ | 205 | β |
| I-1-b-13 | CH₃ | CH₃ | H | CH₃ | CH₃ | —(CH₂)₂—CHOCH₃—(CH₂)₂— | | i-C₃H₇ | 198 | β |

TABLE 58-continued

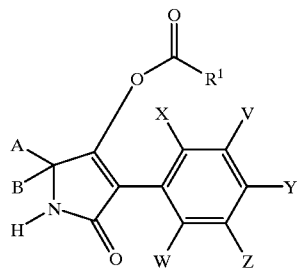

(I-1-b)

| Ex. No. | V | W | X | Y | Z | A | B | R¹ | mp. °C. | Isomer |
|---|---|---|---|---|---|---|---|---|---|---|
| I-1-b-14 | H | $CH_3$ | $CH_3$ | $CH_3$ | $CH_3$ | —$(CH_2)_2$—$CHOCH_3$—$(CH_2)_2$— | | i-$C_3H_7$ | 172 | β |
| I-1-b-15 | H | $CH_3$ | $CH_3$ | $CH_3$ | $CH_3$ | $CH_3$ | i-$C_3H_7$ | i-$C_3H_7$ | 142 | |
| I-1-b-16 | H | $CH_3$ | $CH_3$ | $CH_3$ | $CH_3$ | $CH_3$ | $CH_3$ | i-$C_3H_7$ | 147 | |
| I-1-b-17 | H | Cl | Cl | H | Br | —$(CH_2)_2$—$CHOCH_3$—$(CH_2)_2$— | | i-$C_3H_7$ | >220 | β |
| I-1-b-18 | H | $CH_3$ | H | H | $CH_3$ | —$(CH_2)_2$—$CHOCH_3$—$(CH_2)_2$— | | i-$C_3H_7$ | 189 | β |
| I-1-b-19 | H | Br | Br | —$(CH_2)_3$— | | —$(CH_2)_2$—$CHOCH_3$—$(CH_2)_2$— | | i-$C_3H_7$ | 212 | β |
| I-1-b-20 | $CH_3$ | $CH_3$ | $CH_3$ | $CH_3$ | $CH_3$ | —$(CH_2)_2$—$CHOCH_3$—$(CH_2)_2$— | | i-$C_3H_7$ | 205 | β |
| I-1-b-21 | H | Cl | Cl | Cl | $CH_3$ | —$(CH_2)_2$—$CHOCH_3$—$(CH_2)_2$— | | i-$C_3H_7$ | 188 | β |
| I-1-b-22 | H | Cl | Cl | Cl | $CH_3$ | —$(CH_2)_2$—$CHCH_3$—$(CH_2)_2$— | | i-$C_3H_7$ | 204 | β |
| I-1-b-23 | H | Br | Br | Br | $CH_3$ | —$(CH_2)_2$—$CHCH_3$—$(CH_2)_2$— | | i-$C_3H_7$ | 226 | β |
| I-1-b-24 | H | Br | Br | Br | $CH_3$ | —$(CH_2)_2$—$CHOCH_3$—$(CH_2)_2$— | | i-$C_3H_7$ | 188 | β |

Example (I-1-c-1)

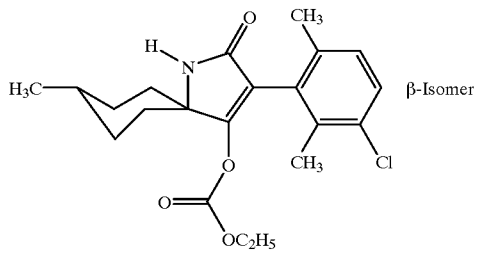

β-Isomer

At 0 to 10° C., 1.2 ml (0.012 mol) of ethyl chloroformate in 5 ml of anhydrous methylene chloride are added dropwise to 3.84 g (0.012 mol) of the compound prepared by the method of Example (I-1-a-1) and 1.7 ml (0.012 mol) of triethylamine in 70 ml of anhydrous $CH_2Cl_2$, and the mixture is stirred at room temperature until the reaction has ended (TLC check). For work-up, the mixture is washed twice with 50 ml of 0.5 N aqueous sodium hydroxide solution, dried over magnesium sulphate and evaporated.

Yield: 3.6 g (76% of theory), mp.: >220° C.

The compounds of the formula (I-1-c) given below are obtained analogously or in accordance with the general preparation instructions:

TABLE 59

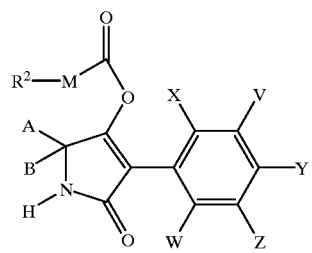

(I-1-c)

| Ex. No. | V | W | X | Y | Z | A | B | M | R² | mp. °C. | Isomer |
|---|---|---|---|---|---|---|---|---|---|---|---|
| I-1-c-2 | H | $CH_3$ | $CH_3$ | $CH_3$ | $CH_3$ | —$(CH_2)_2$—$CHCH_3$—$(CH_2)_2$— | | O | i-$C_4H_9$ | 177 | β |
| I-1-c-3 | H | $CH_3$ | $CH_3$ | H | Br | —$(CH_2)_2$—$CHOCH_3$—$(CH_2)_2$— | | O | $C_2H_5$ | >220 | β |
| I-1-c-4 | H | $CH_3$ | $OCH_3$ | H | Br | —$(CH_2)_2$—$CHOCH_3$—$(CH_2)_2$— | | O | $C_2H_5$ | 207 | β |
| I-1-c-5 | H | $CH_3$ | $CH_3$ | $CH_3$ | Br | —$(CH_2)_2$—$CHOCH_3$—$(CH_2)_2$— | | O | $C_2H_5$ | 214 | β |
| I-1-c-6 | H | Cl | Cl | H | Br | —$(CH_2)_2$—$CHOCH_3$—$(CH_2)_2$— | | O | $C_2H_5$ | >220 | β |

TABLE 59-continued (I-1-c)

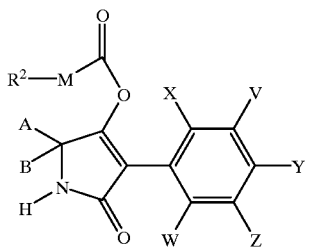

| Ex. No. | V | W | X | Y | Z | A | B | M | R² | mp. °C. | Isomer |
|---|---|---|---|---|---|---|---|---|---|---|---|
| I-1-c-7 | H | CH₃ | CH₃ | CH₃ | CH₃ | CH₃ | CH₃ | O | C₂H₅ | 118 | |
| I-1-c-8 | CH₃ | CH₃ | H | CH₃ | CH₃ | —(CH₂)₂—CHOCH₃—(CH₂)₂— | | O | C₂H₅ | 210 | β |
| I-1-c-9 | H | CH₃ | H | H | CH₃ | —(CH₂)₂—CHOCH₃—(CH₂)₂— | | O | C₂H₅ | 154 | β |
| I-1-c-10 | H | Cl | Cl | Cl | CH₃ | —(CH₂)₂—CHOCH₃—(CH₂)₂— | | O | C₂H₅ | 183 | β |
| I-1-c-11 | H | Cl | Cl | Cl | CH₃ | —(CH₂)₂—CHCH₃—(CH₂)₂— | | O | C₂H₅ | 181 | β |
| I-1-c-12 | H | Br | Br | Br | CH₃ | —(CH₂)₂—CHCH₃—(CH₂)₂— | | O | C₂H₅ | 188 | β |

Example (II-1)

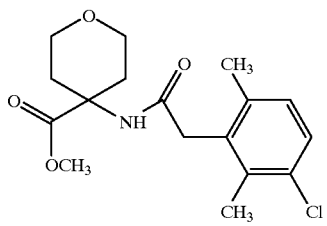

At 30 to 40° C., 16.7 g (0.0544 mol) of the compound prepared by the method of Example (XXIX-1) in 160 ml of anhydrous methylene chloride are added dropwise to 26.6 g (0.257 mol) of conc. sulphuric acid, and the mixture is stirred for 2 hours at this temperature. 37 ml of absolute methanol are then added in such a way that the internal temperature is about 40° C., and stirring is continued at 40 to 70° C. for a further 6 hours.

For work-up, the mixture is poured on 0.28 kg of ice, extracted with methylene chloride, washed with aqueous sodium bicarbonate solution, dried and evaporated. The residue is recrystallized from methyl tert-butyl ether/n-hexane.

Yield: 16.5 g (89% of theory), mp.: 168° C.

Example (II-2)

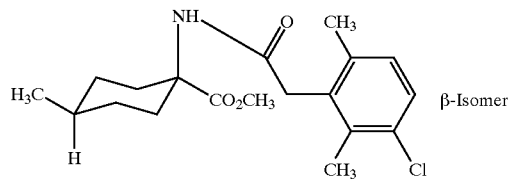

15.9 g (0.08 mol) of 3-chloro-2,6-dimethylphenylacetic acid and 17.7 ml (0.24 mol) of thionyl chloride are stirred for 30 minutes at room temperature and subsequently at 80° C. until the evolution of gas has ceased. Excess thionyl chloride is removed at 50° C. under reduced pressure. 50 ml of anhydrous toluene are then added, and the solution is evaporated once again. The residue is taken up in 100 ml of anhydrous THF (solution 1).

At 0 to 10° C., solution 1 is added dropwise to 16.8 g of methyl cis4-methylcyclohexylamine-1-carboxylate and 24.6 ml (0.176 mol) of triethylamine in 160 ml of anhydrous THF, and the solution is subsequently stirred at room temperature for 1 hour. The mixture is filtered under suction, washed with anhydrous THF and evaporated. The residue is taken up in methylene chloride, washed with 0.5 N HCl, dried and evaporated. The crude product is recrystallized from methyl tert-butyl ether/n-hexane.

Yield: 26.9 g (74% of theory), mp.: 163° C.

The compounds of the formula (II) given below are prepared analogously to Examples (II-1) and (II-2) and in accordance with the general preparation instructions.

TABLE 60

Compounds of the formula (II)

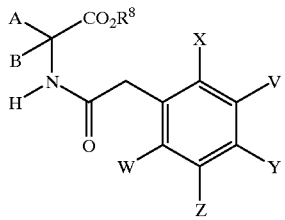

| Ex. No. | V | W | X | Y | Z | A | B | $R^8$ | mp. °C. | Isomer |
|---|---|---|---|---|---|---|---|---|---|---|
| II-3 | H | $CH_3$ | $CH_3$ | H | Cl | —$(CH_2)_2$—CHOCH$_3$—$(CH_2)_2$— | | $CH_3$ | 154 | β |
| II-4 | H | $CH_3$ | $CH_3$ | $CH_3$ | $CH_3$ | —$(CH_2)_2$—CHCH$_3$—$(CH_2)_2$— | | $CH_3$ | 169 | β |
| II-5 | H | $CH_3$ | $CH_3$ | $CH_3$ | $CH_3$ | —$(CH_2)_2$—CHOCH$_3$—$(CH_2)_2$— | | $CH_3$ | 174 | β |
| II-6 | H | $CH_3$ | $CH_3$ | $CH_3$ | $CH_3$ | —$(CH_2)_2$—O—$(CH_2)_2$— | | $CH_3$ | 174 | — |
| II-7 | H | $CH_3$ | $CH_3$ | $CH_3$ | Br | —$(CH_2)_2$—CHCH$_3$—$(CH_2)_2$— | | $CH_3$ | 166 | β |
| II-8 | H | $CH_3$ | $CH_3$ | $CH_3$ | $CH_3$ | $CH_3$ | $CH_3$ | $CH_3$ | 152 | — |
| II-9 | H | $CH_3$ | $CH_3$ | $CH_3$ | $CH_3$ | —$(CH_2)_2$—CHOC$_2$H$_5$—$(CH_2)_2$— | | $CH_3$ | 145 | β |
| II-10 | H | $CH_3$ | $CH_3$ | $CH_3$ | $CH_3$ | i-$C_3H_7$ | $CH_3$ | $CH_3$ | 98 | — |
| II-11 | H | $CH_3$ | $CH_3$ | $CH_3$ | Br | —$(CH_2)_2$—CHOCH$_3$—$(CH_2)_2$— | | $CH_3$ | 156 | β |
| II-12 | $CH_3$ | $CH_3$ | $CH_3$ | H | $CH_3$ | —$(CH_2)_2$—CHCH$_3$—$(CH_2)_2$— | | $CH_3$ | 181 | β |
| II-13 | $CH_3$ | $CH_3$ | $CH_3$ | H | $CH_3$ | —$(CH_2)_2$—CHOCH$_3$—$(CH_2)_2$— | | $CH_3$ | 145 | β |
| II-14 | $CH_3$ | $CH_3$ | H | $CH_3$ | $CH_3$ | —$(CH_2)_2$—CHCH$_3$—$(CH_2)_2$— | | $CH_3$ | 161 | β |
| II-15 | $CH_3$ | $CH_3$ | H | $CH_3$ | $CH_3$ | —$(CH_2)_2$—CHOCH$_3$—$(CH_2)_2$— | | $CH_3$ | 166 | β |
| II-16 | H | $CH_3$ | $CH_3$ | H | Br | —$(CH_2)_2$—CHCH$_3$—$(CH_2)_2$— | | $CH_3$ | 154 | β |
| II-17 | H | $CH_3$ | $CH_3$ | H | Br | —$(CH_2)_2$—CHOCH$_3$—$(CH_2)_2$— | | $CH_3$ | 135 | β |
| II-18 | H | Cl | Cl | H | Br | —$(CH_2)_2$—CHCH$_3$—$(CH_2)_2$— | | $CH_3$ | 171 | β |
| II-19 | H | Cl | Cl | H | Br | —$(CH_2)_2$—CHOCH$_3$—$(CH_2)_2$— | | $CH_3$ | 160 | β |
| II-20 | H | Br | Br | —$(CH_2)_3$— | | —$(CH_2)_2$—CHCH$_3$—$(CH_2)_2$— | | $CH_3$ | 154 | β |
| II-21 | H | Br | Br | —$(CH_2)_3$— | | —$(CH_2)_2$—CHOCH$_3$—$(CH_2)_2$— | | $CH_3$ | 158 | β |
| II-22 | H | $CH_3$ | $OCH_3$ | H | Br | —$(CH_2)_2$—CHCH$_3$—$(CH_2)_2$— | | $CH_3$ | 174 | β |
| II-23 | H | $CH_3$ | $OCH_3$ | H | Br | —$(CH_2)_2$—CHOCH$_3$—$(CH_2)_2$— | | $CH_3$ | 169 | β |
| II-24 | H | $CH_3$ | $CH_3$ | $CH_3$ | $CH_3$ | —$(CH_2)_5$— | | $CH_3$ | 136 | — |
| II-25 | H | $CH_3$ | $CH_3$ | $CH_3$ | $CH_3$ | —$(CH_2)_4$— | | $CH_3$ | 145 | — |
| II-26 | $CH_3$ | $CH_3$ | $CH_3$ | $CH_3$ | $CH_3$ | —$(CH_2)_2$—CHCH$_3$—$(CH_2)_2$— | | $CH_3$ | 182 | β |
| II-27 | $CH_3$ | $CH_3$ | $CH_3$ | $CH_3$ | $CH_3$ | —$(CH_2)_2$—CHOCH$_3$—$(CH_2)_2$— | | $CH_3$ | 175 | β |
| II-28 | H | Cl | Cl | Cl | $CH_3$ | —$(CH_2)_2$—CHCH$_3$—$(CH_2)_2$— | | $CH_3$ | 174 | β |
| II-29 | H | Cl | Cl | Cl | $CH_3$ | —$(CH_2)_2$—CHOCH$_3$—$(CH_2)_2$— | | $CH_3$ | 167 | β |
| II-30 | H | Br | Br | Br | $CH_3$ | —$(CH_2)_2$—CHCH$_3$—$(CH_2)_2$— | | $CH_3$ | 210 | β |
| II-31 | H | Br | Br | Br | $CH_3$ | —$(CH_2)_2$—CHOCH$_3$—$(CH_2)_2$— | | $CH_3$ | 169 | β |

Example (XXIX-1)

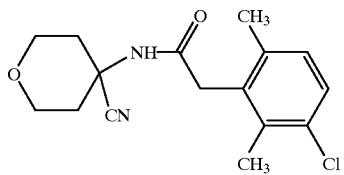

Starting from 12.6 g of $^3$-chloro-2,6-dimethylphenylacetic acid, solution 1 is prepared as described in Example (II-2).

At 0 to 10° C., solution 1 is added dropwise to 15.1 g of 4-amino-4-cyano-tetrahydropyran (70% strength) and 9.2 ml (0.066 mol) of triethylamine in 120 ml of anhydrous THF, and the mixture is stirred for a further hour at room temperature. The mixture is then evaporated and the residue is taken up in methylene chloride, washed with 0.5 N HCl, dried and evaporated. The crude product is recrystallized from MTB ether/n-hexane.

Yield: 16.7 g (90% of theory), mp.: 176° C.

The compounds of the formula (XXIX) given below are prepared analogously to Example (XXIX-1) and in accordance with the general preparation instructions:

TABLE 61

(XXIX)

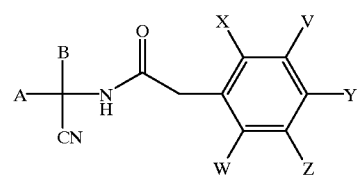

| Ex. No. | V | W | X | Y | Z | A | B | mp. °C. |
|---|---|---|---|---|---|---|---|---|
| XXIX-2 | H | CH₃ | CH₃ | CH₃ | CH₃ | —(CH₂)₂—O—(CH₂)₂— | | 163 |
| XXIX-3 | H | CH₃ | CH₃ | CH₃ | CH₃ | i-Pr | CH₃ | 162 |
| XXIX-4 | H | CH₃ | CH₃ | CH₃ | CH₃ | —(CH₂)₄— | | 185 |

Example (I-2-a-1)

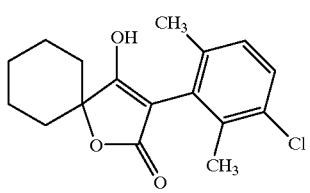

Example (I-2-b-1)

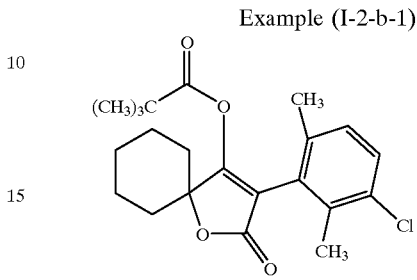

8.42 g (75 mmol) of potassium tert-butoxide are initially charged in 50 ml of anhydrous tetrahydrofuran (THF), and at 0 to 10° C. a solution of 17.62 g (50 mmol) of 1-ethyloxycarbonyl-cyclohexyl 3-chloro-2,6-dimethylphenylacetate prepared by the method of Example (III-1) in 50 ml of anhydrous THF is added dropwise, and the solution is stirred at room temperature overnight.

For work-up, the reaction mixture is poured into 600 ml of water, acidified with 10% strength hydrochloric acid, the product is then filtered off with suction, taken up in methylene chloride, concentrated, and the crystals are triturated with petroleum ether.

Yield: 9.7 g (63% of theory) of mp.: 193° C.

The compounds (I-2-a) given below are obtained analogous to Example (I-2-a-1) and in accordance with the general preparation instructions:

3.06 g (10 mmol) of the compound prepared by the method of Example I-2-a-1 are initially charged in 40 ml of anhydrous THF, 1.1 g (11 mmol) of triethylamine are added, a solution of 1.2 g (10 mmol) of pivaloyl chloride is added dropwise while cooling with ice, and stirring at room temperature is continued overnight. For work-up, the solution is concentrated, stirred with water, filtered off with suction, dried, the residue is taken up in ether, washed with 1 N NaOH, and the organic phase is dried over MgSO₄ and evaporated. For further purification, the crude product is mixed with a little petroleum ether.

Yield: 3.1 g (79% of theory) of mp.: 126° C.

The compounds of the formula (I-2-b) given below are obtained analogously or in accordance with the general preparation instructions.

TABLE 62

Compounds of the formula (I-2-a)

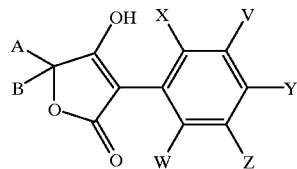

| Ex. No. | V | W | X | Y | Z | A | B | mp. °C. |
|---|---|---|---|---|---|---|---|---|
| I-2-a-2 | H | CH₃ | CH₃ | CH₃ | CH₃ | —(CH₂)₅— | | 204–205 |
| I-2-a-3 | H | CH₃ | CH₃ | CH₃ | CH₃ | —(CH₂)₂—CHOCH₃—(CH₂)₂— | | 113–118 |
| I-2-a-4 | CH₃ | CH₃ | CH₃ | H | CH₃ | —(CH₂)₅— | | >250 |
| I-2-a-5 | CH₃ | CH₃ | CH₃ | H | CH₃ | —(CH₂)₂—CHOCH₃—(CH₂)₂— | | 115–118 |

TABLE 63

Compounds of the formula (I-2-b)

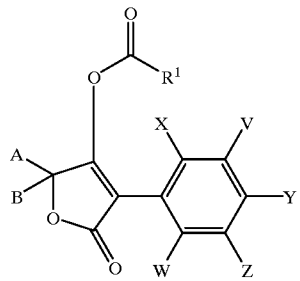

(I-2-b)

| Ex. No. | V | W | X | Y | Z | A | B | $R^1$ | mp. °C. |
|---|---|---|---|---|---|---|---|---|---|
| I-2-b-2 | H | $CH_3$ | $CH_3$ | H | Cl | —(CH$_2$)$_5$— | | t-$C_4H_9$—$CH_2$— | 125 |
| I-2-b-3 | H | $CH_3$ | $CH_3$ | $CH_3$ | $CH_3$ | —(CH$_2$)$_5$— | | t-$C_4H_9$— | 117–119 |
| I-2-b-4 | H | $CH_3$ | $CH_3$ | $CH_3$ | $CH_3$ | —(CH$_2$)$_2$—CHOCH$_3$—(CH$_2$)$_2$— | | i-$C_4H_9$— | 150–153 |
| I-2-b-5 | $CH_3$ | $CH_3$ | $CH_3$ | H | $CH_3$ | —(CH$_2$)$_5$— | | t-$C_4H_9$— | 143–145 |
| I-2-b-6 | $CH_3$ | $CH_3$ | $CH_3$ | H | $CH_3$ | —(CH$_2$)$_2$—CHOCH$_3$—(CH$_2$)$_2$— | | i-$C_4H_9$— | 177–179 |
| I-2-b-7 | H | $CH_3$ | $CH_3$ | $CH_3$ | $CH_3$ | —(CH$_2$)$_2$—CHOCH$_3$—(CH$_2$)$_2$— | | i-$C_3H_7$ | 148 |

Example I-2-c-1

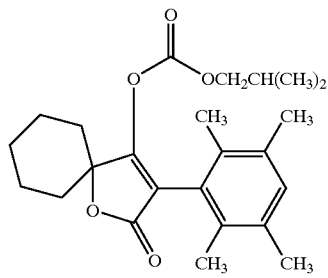

0.68 g (5 mmol) of isobutyl chloroformate are added dropwise to 1.50 g (5 mmol) of the compound prepared by the method of Example (I-2-a-4) and 0.55 g (5.5 mmol) of triethylamine in 20 ml of dichloromethane at room temperature. Stirring is continued for 2 hours. The mixture is then washed with 10% strength aqueous citric acid and 1 N aqueous sodium hydroxide solution, and the dichloromethane phase is dried and concentrated. The residue, which is obtained as an oil, is stirred with petroleum ether, and the solid which forms is filtered off with suction.

Yield 0.76 g, mp.: 118 to 119° C.

The compounds of the formula (I-2-c) given below are obtained analogously or in accordance with the general preparation instructions.

TABLE 63a

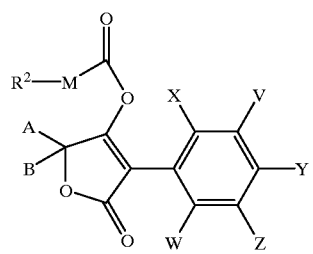

(I-2-c)

| Ex. No. | V | W | X | Y | Z | A | B | M | $R^2$ | mp. °C. | Isomer |
|---|---|---|---|---|---|---|---|---|---|---|---|
| I-2-c-2 | H | $CH_3$ | $CH_3$ | $CH_3$ | $CH_3$ | —(CH$_2$)$_2$—CHOCH$_3$—(CH$_2$)$_2$— | | O | $CH_2$-i-$C_3H_7$ | 1) | β |
| I-12c-3 | H | $CH_3$ | $CH_3$ | $CH_3$ | $CH_3$ | —(CH$_2$)$_2$—CHOCH$_3$—(CH$_2$)$_2$— | | S | i-$C_3H_7$ | 2) | β |

1) $^1$HNMR, δ = 1.10, 1.10–2.30, 2.11, 2.22, 3.25/3.60, 3.35/3.39, 6.87
2) $^1$H-NMR, δ = 1.0; 1.5–2.3; 2.10, 2.23, 3.25/3.60, 3.35/3.38, 6.90

Example (III-1)

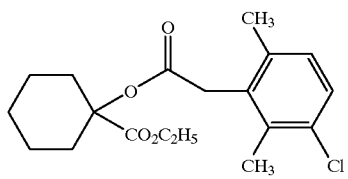

10.85 g (50 mmol) of 3-chloro-2,6-dimethyl-phenylacetyl chloride together with 8.6 g (50 mmol) of ethyl 1-hydroxy-cyclohexanecarboxylate are boiled for 1 h in 100 ml of toluene, and the solution is then evaporated.

Yield: 17.5 g (quantitative) of 1-ethoxycarbonyl-cyclohexyl 3-chloro-2,6-dimethylphenylacetate as a colourless oil.

GC/MS m/e⁻=M⁺ 352 (6%), 155 (100%), 109 (48%), 81 (76%), 29 (76%)

TABLE 64

Compounds of the formula (III)

(III)

[Structure of formula (III) showing A, B, CO₂R⁸, O, V, W, X, Y, Z substituents on phenylacetate]

| Ex. No. | V | W | X | Y | Z | A | B | R⁸ |
|---|---|---|---|---|---|---|---|---|
| III-2 | H | $CH_3$ | $CH_3$ | $CH_3$ | $CH_3$ | —$(CH_2)_5$— | | $C_2H_5$ |
| III-3 | H | $CH_3$ | $CH_3$ | $CH_3$ | $CH_3$ | —$(CH_2)_2$—$CHOCH_3$—$(CH_2)_2$— | | $C_2H_5$ |
| III-4 | $CH_3$ | $CH_3$ | $CH_3$ | H | $CH_3$ | —$(CH_2)_5$— | | $C_2H_5$ |
| III-5 | $CH_3$ | $CH_3$ | $CH_3$ | H | $CH_3$ | —$(CH_2)_2$—$CHOCH_3$—$(CH_2)_2$— | | $C_2H_5$ |

The compounds of the formula III are obtained as viscous oils and are in most cases without further purification and characterization converted into the compounds of the formula I-2-a.

Example (I-3-a-1)

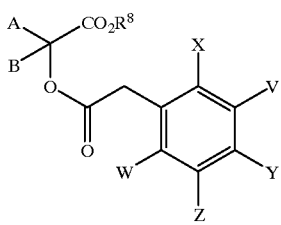

16.2 g (35 mmol) of the compounds prepared by the method of Example (IV-1) are initially charged in 70 ml of toluene and 35 ml of trifluoroacetic acid and heated under reflux for 5 hours. The trifluoroacetic acid is evaporated under reduced pressure and the residue is treated twice with toluene which is also evaporated under reduced pressure. The residue is taken up in 400 ml of water and 120 ml of methyl tert-butyl ether (MTB) ether, made alkaline using NaOH, extracted twice with MTB ether, and the aqueous phase is acidified with hydrochloric acid. The aqueous phase is extracted 3 times with MTB ether, the organic phases are dried and concentrated.

Yield: 8.5 g (78% of theory); mp.: 226–231° C.

Example (I-3-b-1)

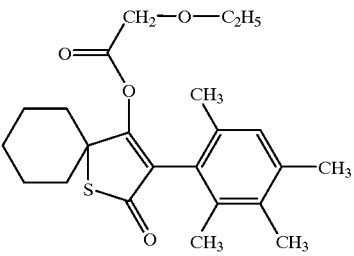

1.5 g (4.7 mmol) of the compound prepared by the method of Example (I-3-a-1) in 20 ml of absolute methylene chloride are treated with 0.98 ml (1.5 eq) of triethylamine. While cooling with ice, 0.86 g (1.5 eq) of ethoxyacetyl chloride dissolved in 3 ml of absolute methylene chloride are added dropwise. The solution is stirred for one to two hours at room temperature and washed twice with 10% strength citric acid, and the combined aqueous, acidic phases are extracted with methylene chloride. The combined organic phases are washed 2 times with 1 N NaOH, and the aqueous alkaline phases are subsequently extracted with methylene chloride. The combined organic phases are dried and concentrated.

Yield: 1.70 g (86% of theory), oil.

¹H-NMR (400 MHz, CDCl₃): 1.08 (t, 3H, 1.1–2.1 (m, 10H); 2.1–2.2 (4s, 12H); 3.1 (q, 2H); 3.9 (m, 2H); 6.83 (s, 1H).

Example (I-3-b-2)

Analogously to Example (I-3-b-1), the compound below, which is obtained as an oil, was prepared by using pivaloyl chloride.

Yield: 2.00 g (100% of theory).

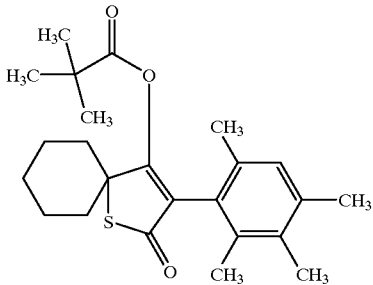

Example (I-3-c-1)

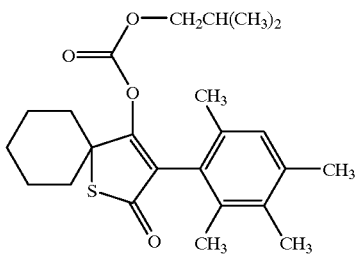

The reaction of 1.5 g (4.7 mmol) of the compound prepared by the method of Example (I-3-a-1) with 0.91 ml (1.5 eq) of isobutyl chloroformate under the reaction conditions described in Example (I-3-b-1) affords 1.85 g (94% of theory) of the compound shown above.

mp.: 83–89° C.

Example (IV-1)

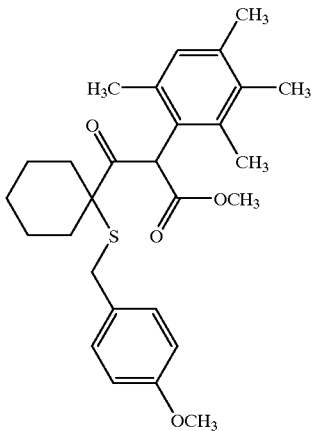

1 drop of dimethylformamide (DMF) and then 11.4 g (96 mmol) of thionyl chloride are added to 18 g (64 mmol) of the compound (I-3-b-2)

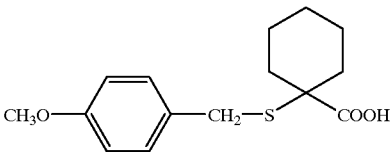

in 70 ml of absolute toluene. The solution is stirred for 5 minutes at room temperature and subsequently at 100° C. until the gas formation has ended. The mixture is concentrated under reduced pressure, treated twice with toluene which is distilled off again in each case, and the mixture is subsequently stirred for 1 hour under high vacuum. The acid chloride obtained is dissolved in 40 ml of absolute tetrahydrofuran (THY) (solution A).

At about 0° C., 57 ml (177 mmol) of a solution of lithium diisopropylamide (LDA) in [lacuna] are initially charged in 100 ml of absolute THF. At this temperature, 22.1 g (107 mmol) of methyl 2,3,4,6-tetramethylphenylacetate dissolved in 40 ml of absolute THF are added dropwise, and stirring is continued for a further 30 minutes.

Subsequently, again at about 0° C., solution A is added dropwise and the mixture is stirred for 1 hour without cooling.

The mixture is admixed with 350 ml of MTB ether and a few drops of water, washed twice with 10% strength aqueous ammonium chloride solution, and the organic phase is dried and concentrated. The crude product is stirred with petroleum ether. The product is filtered off with suction and dried.

Yield: 16.20 g (54% of theory). mp.: 114–116° C.

Example (I-4-a-1)

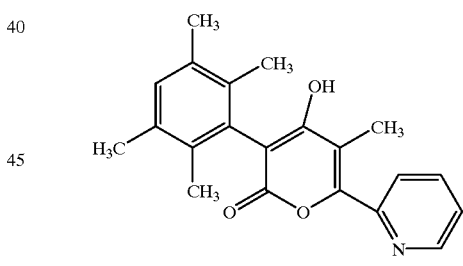

2.4 g (10 mmol) of 2,3,5,6-tetramethyl-phenyl-chlorocarbonyl ketene are initially charged in 20 ml of toluene (p.a.). At room temperature, 1.35 g (10 mmol) of 2-pyridyl ethyl ketone are added, and the solution is stirred under reflux for 8 hours. On cooling, the product crystallizes out. The precipitate is filtered off under suction and washed twice with cyclohexane.

Yield: 1.4 g (41% of theory). mp.: 202–205° C.

The compounds of the formula (I-4-a) given in the table below were prepared analogously to Example (I-4-a-1) or according to the general preparation instructions:

TABLE 65

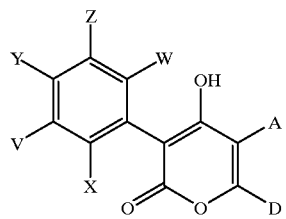

(I-4-a)

| Ex. No. | V | W | X | Y | Z | A | D | mp. °C. |
|---|---|---|---|---|---|---|---|---|
| I-4-a-2 | CH$_3$ | CH$_3$ | CH$_3$ | H | CH$_3$ | CH$_3$ | 4-F—C$_6$H$_4$ | 204–206 |
| I-4-a-3 | CH$_3$ | CH$_3$ | CH$_3$ | H | CH$_3$ | CH$_3$ | t-C$_4$H$_9$ | 222–224 |
| I-4-a-4 | H | CH$_3$ | CH$_3$ | CH$_3$ | CH$_3$ | CH$_3$ | 4-F—C$_6$H$_4$ | 236–238 |
| I-4-a-5 | H | CH$_3$ | CH$_3$ | CH$_3$ | CH$_3$ | CH$_3$ | Cyclopentyl | Oil |
| I-4-a-6 | H | CH$_3$ | CH$_3$ | CH$_3$ | CH$_3$ | CH$_3$ | 2-Pyridyl | 101–103 |
| I-4-a-7 | H | CH$_3$ | CH$_3$ | CH$_3$ | CH$_3$ | CH$_3$ | 4-Pyridyl | 300–302 |
| I-4-a-8 | H | CH$_3$ | CH$_3$ | CH$_3$ | CH$_3$ | —(CH$_2$)$_4$— | | 165–168 |
| I-4-a-9 | H | CH$_3$ | CH$_3$ | CH$_3$ | CH$_3$ | —C(CH$_3$)$_2$OC(CH$_3$)$_2$— | | 178–180 |

Example I-4-b-1

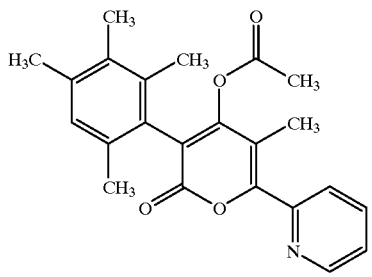

1.7 g (5 mmol) of the compound prepared by the method of Example I-4-a-6 are initially charged in 20 ml of ethyl acetate p.a. At 20° C., 0.5 g (5 mmol) of triethylamine are added, and at 0C 0.39 g (5 mmol) of ClCOCH$_3$ in 5 ml of ethyl acetate are added dropwise. The reaction is carried out with the exclusion of moisture. The mixture is stirred at 20° C. for 20 hours. The precipitate is separated off and washed with ethyl acetate. The organic phase is washed with twice 25 ml of half-concentrated NaCl solution, dried over sodium sulphate and evaporated.

Yield: 1 g (53% of theory), mp.: 170 to 172° C.

The compounds of the formula (I-4-b) given below are obtained analogously or in accordance with the general preparation instructions.

TABLE 65-a

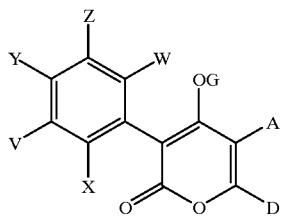

(I-4-b)

| Ex. No. | V | W | X | Y | Z | A | D | G | m.p. °C. |
|---|---|---|---|---|---|---|---|---|---|
| I-4-b-2 | H | CH$_3$ | CH$_3$ | CH$_3$ | CH$_3$ | CH$_3$ | 2-Pyridyl | COCH$_3$ | 170–172 |
| I-4-b-3 | H | CH$_3$ | CH$_3$ | CH$_3$ | CH$_3$ | CH$_3$ | 2-Pyridyl | CO-(6-Cl-3-Pyridyl) | 96–98 |
| I-4-b-4 | H | CH$_3$ | CH$_3$ | CH$_3$ | CH$_3$ | CH$_3$ | 2-Pyridyl | CO-4-Cl—C$_6$H$_4$ | 100–102 |

Example (I-4-c-1)

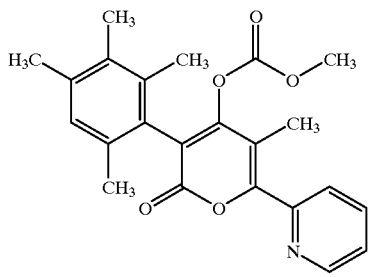

1.7 g (5 mmol) of the compound prepared by the method of Example I-4-a-6 are initially charged in 20 ml of ethyl acetate p.a.. At 20° C., 0.5 g (5 mmol) of triethylamine are added, and at 0° C. 0.47 g (5 mmol) of $ClCO_2CH_3$ in 5 ml of ethyl acetate are added dropwise. The reaction is carried out with the exclusion of moisture. The mixture is stirred at 20° C. for 20 hours. For work-up, the precipitate is separated off and washed with ethyl acetate. The organic phase is washed with twice 25 ml of half-concentrated NaCl solution, dried over sodium sulphate and evaporated.

Yield: 1.6 , (81% of theory), mp.: 136 to 139° C.

Example (VI-1)

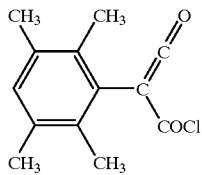

At room temperature, 31 ml of thionyl chloride are added dropwise to 15 g (63.5 mmol) of the compound prepared by the method of Example (XXXIII-1) in 20 ml of toluene, and the solution is stirred initially for 1 hour at room temperature and then at about 95° C. overnight. After cooling, HCl and $SO_2$ are blown off at about 45° C. by passing argon through the solution, and remaining volatile compounds are subsequently removed using high vacuum.

Yield: 7.4 g (52% of theory), bp.: 110–111° C./0.08 mbar.

Example (VI-2)

Analogously to Example (VI-1) or according to the general preparation procedures, the compound (VI-2)

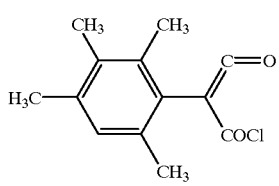

is obtained.

$^1$H-NMR (400 MHz, $CDCl_3$): δ=2.13 (s, 3H, Ar—$CH_3$), 2.22 (s, 3H, Ar—$CH_3$), 2.28 (s, 6H, 2×Ar—$CH_3$); 6.94 (s, 1H, Ar—H).

Example (XXXIII-1)

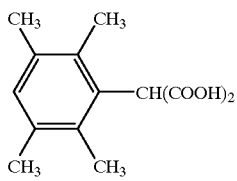

At room temperature, 40 g (0.155 mol) of the compound prepared by the method of Example (XXXIV-1) are added to 28.2 g of potassium hydroxide in 37.8 g of water and 75.6 ml of methanol, and the mixture is heated under reflux for 10 hours.

After cooling, the mixture is concentrated under reduced pressure, the residue is dissolved in about 100 ml of ice water and, while cooling, acidified with half-concentrated hydrochloric acid. The phases are separated and extracted with toluene. The solid which separates off is filtered off with suction, stirred with a little toluene and filtered off under suction once more.

Yield: 35.20 g (70.3% of theory). mp.: 193–198° C.

Example (XXXIII-2)

Analogously to Example (XXXIII-1) or according to the general preparation instructions, the compound (XXXIII-2)

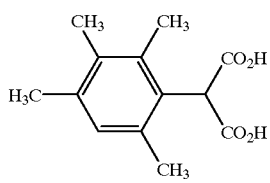

of mp.: 181° C. (decomposition) is obtained.

Examnple (XXXIV-1)

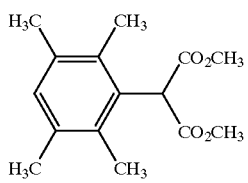

At room temperature, 350 g (3.5 mol) of dimethyl carbonate and then, slowly, at 85–90° C., 42.0 g (0.203 mol) of methyl 2,3,5,6-tetramethylphenylacetate are added dropwise to 7.9 g (0.264 mol) of 80% strength sodium hydride, and the mixture is stirred overnight. After cooling, a little methanol is added to the mixture which is then poured into about 1 l of ice water and acidified with half-concentrated hydrochloric acid. The organic phase is separated off, the aqueous phase is extracted with toluene, and the combined organic phases are dried and concentrated. The residue is subsequently distilled using high vacuum.

Yield: 41.9 g (82% of theory). mp.: 125–129° C.

Analogously to Example (XXXIV-1) and according to the general preparation instructions, the compound

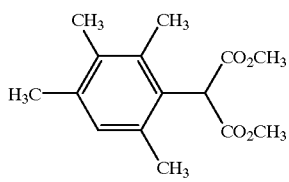

(XXXIV-2)

of mp.: 132–134° C. is obtained.

Example (XXIII-1)

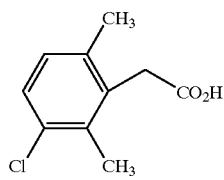

At room temperature, 171.9 g of the compound prepared by the method of Example XXVI-1 are added dropwise to a mixture of 85.8 g (1.532 mol) of KOH in 110.2 ml of water and 224 ml of methanol, and the mixture is heated under reflux for 5 h. After cooling, the mixture is diluted with 300 ml of water and washed with methyl tert-butyl ether. The aqueous phase is acidified with half-concentrated hydrochloric acid, filtered off with suction and dried, and the residue is recrystallized from toluene.

Yield: 111.4 g (Δ69% of theory) mp.: 128–130° C.

The compounds of the formula (XXIII) given below were obtained analogously to Example (XXIII-1) and according to the general preparation instructions:

TABLE 66

(XXIII)

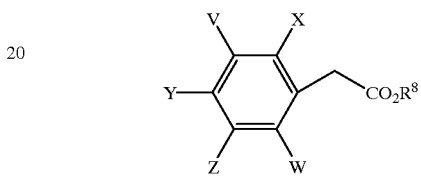

| Ex. No. | V | W | X | Y | Z | mp. ° C. |
|---|---|---|---|---|---|---|
| XXIII-2 | H | $CH_3$ | $CH_3$ | H | Br | 112 |
| XXIII-3 | H | Cl | Cl | H | Br | 157 |
| XXIII-4 | H | Br | Br | —$(CH_2)_3$— | | 175 |
| XXIII-5 | H | Br | Br | Br | $CH_3$ | 217–220 |
| XXIII-6 | H | Cl | Cl | Cl | $CH_3$ | 176–179 |

Example (XXIV-1)

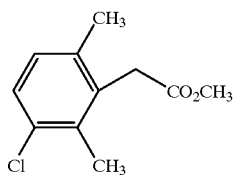

At room temperature, 992 ml of 30% strength sodium methoxide solution in methanol are added dropwise to a solution of 353.7 g (1.3 mol) of the compound prepared by the method of Example XXV-1 in 560 ml of methanol, and the mixture is boiled under reflux for 5 hours. After cooling to room temperature, 148 ml of conc. sulphuric acid are added dropwise, and the mixture is heated under reflux for 1 hour, cooled, concentrated, admixed with water, extracted with methylene chloride, dried and concentrated. 179.1 g of an oil of the desired product XXIV-1 (about 51% according to GC), the acid XXIII-I and 1,3-dichloro-2,6-dimethylbenzene are obtained. This mixture was used for the reaction of Example XXIII-1.

The compounds of the formula (XXIV) given below were obtained analogously to Example (XXIV-1) and according to the general preparation instructions:

TABLE 67

(XXIV)

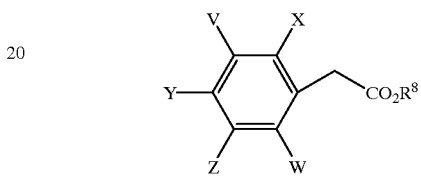

| Ex. No. | V | W | X | Y | Z | $R^8$ | $bp_{mbar}$ ° C. |
|---|---|---|---|---|---|---|---|
| XXIV-2 | H | $CH_3$ | $CH_3$ | H | Br | $CH_3$ | * |
| XXIV-3 | H | Cl | Cl | H | Br | $CH_3$ | 85–92 0.1 mbar |
| XXIV-4 | H | Br | Br | —$(CH_2)_3$— | | $CH_3$ | * |
| XXIV-5 | H | Br | Br | Br | $CH_3$ | $CH_3$ | 143 0.08 mbar |
| XXIV-6 | H | Cl | Cl | Cl | $CH_3$ | $CH_3$ | 138 0.4 mbar |

* These compounds were employed directly for synthesis as crude products for preparing compounds of the formula (XXIII).

Example (XXV-1)

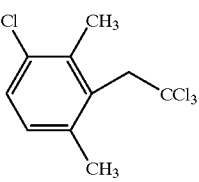

2205 g (22.8 mol) of 1,1-dichloroethylene (vinylidene chloride) are added dropwise to a well-cooled mixture of 229.7 g (2.27 mol) of tert-butyl nitrite and 255 g (1.776 mol) of anhydrous copper-(II) chloride in 990 ml of anhydrous acetonitrile, the mixture being kept at room temperature. Then, at a temperature of below 30° C., a mixture of 232 g (1.49 mol) of 3-chloro-2,6-dimethylaniline in 1500 ml of anhydrous acetonitrile is added -dropwise. At room temperature, the mixture is stirred until the formation of gas has ceased, and the mixture is then carefully poured into 6 liters of 20% strength hydrochloric acid and extracted with methylene chloride. The organic phases are combined, washed once more with 20% strength hydrochloric acid, dried and concentrated. The remaining oil is used without any further work-up for the reaction of Example (XXIV-1).

The compounds of the formula (XXV) given below were obtained analogously to Example (XXV-1) and according to the general preparation instructions:

TABLE 68

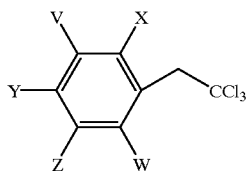

(XXV)

| Ex. No. | V | W | X | Y | Z |
|---|---|---|---|---|---|
| XXV-2 | H | CH$_3$ | CH$_3$ | H | Br |
| XXV-3 | H | Cl | Cl | H | Br |
| XXV-4 | H | Br | Br | —(CH$_2$)$_3$— | |
| XXV-5 | H | Br | Br | Br | CH$_3$ |
| XXV-6 | H | Cl | Cl | Cl | CH$_3$ |

The compounds listed in Table 68 were employed as crude products in the saponification reaction leading to compounds of the formula (XXIV), and were, for that reason, not further characterized.

USE EXAMPLES

Example 1

Phaedon Larvae Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*) while the leaves are still moist.

After the specified period of time, the destruction in % is determined. 100% means that all the beetle larvae have been killed; 0% means that none of the beetle larvae have been killed.

In this test, for example the compounds of Preparation Examples (I-1-a-2), (I-1-a-3), (I-1-b-1), (I-1-b-2) and (I-1-c-1) at an exemplary active compound concentration of 1000 ppm caused a destruction of 100% after 7 days.

Example 2

Tetranychus Test (OP Resistant/Spray Treatment)

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentrations.

Bean plants (*Phaseolus vulgaris*) heavily infected by all stages of the spider mite (*Tetranychus urticae*) are sprayed with a preparation of the active compound of the desired concentration.

After the specified period of time, the destruction in % is determined. 100% means that all spider mites have been killed; 0% means that none of the spider mites have been killed.

In this test, an activity of 100% was shown, after 7 days, for example by the compound of Preparation Example (I-1-a-2) at an exemplary active compound concentration of 1000 ppm.

Example 3

Plutella Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) while the leaves are still moist.

After the specified period of time, the destruction in % is determined. 100% means that all the caterpillars have been killed; 0% means that none of the caterpillars have been killed.

In this test, for example the compounds of Preparation Examples (I-1-a-3), (I-1-b-1), (I-1-b-2), (I-1-b-6) and (I-1-c-1) at an exemplary active compound concentration of 0.1% caused a destruction of 100% after 7 days.

Example 4

Spodoptera Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with caterpillars of the owlet moth (*Spodoptera frugiperda*), as long as the leaves are still moist.

After the specified period of time, the destruction in % is determined. 100% means that all the caterpillars have been killed; 0% means that none of the caterpillars have been killed.

In this test, for example the compounds of Preparation Examples (I-1-a-2), (I-1-a-3) and (I-1-b-4) at an exemplary active compound concentration of 0.1% caused a destruction of at least 80% after 7 days.

Example 5

Neplotettix Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (*Oryzae sativa*) are treated by being dipped into the preparation of the active compound of the desired concentration and are infested with larvae of the green rice leafhopper (*Nephotettix cincticeps*) while the seedlings are still moist.

After the specified period of time, the destruction in % is determined. 100% means that all the leafhoppers have been killed; 0% means that none of the leafhoppers have been killed.

In this test, for example, the compounds of Preparation Examples (I-1-a-1), (I-1-a-2), (I-1-a-3), (I-1-b-1), (I-1-b-2), (I-1-b-3), (I-1-b-4), (I-1-b-5), (I-1-b-6) and (I-1-c-2) at an exemplary active compound concentration of 0.1% caused a destruction of 100% after 6 days.

Example 6

Myzus Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which have been heavily infested with the peach aphid (*Myzus persicae*) are treated by being dipped into the preparation of the active compound of the desired concentration.

After the specified period of time, the destruction in % is determined. 100% means that all the aphids have been killed; 0% means that none of the aphids have been killed.

In this test, for example, the compounds according to Preparation Examples (I-1-a-1), (I-1-a-2), (I-1-a-3), (I-1-b-2), (I-1-b-3) and (I-2-a-1) at an exemplary active compound concentration of 0.1% caused a destruction of at least 80% after 6 days.

Example 7

Tetranychus Test (OP Resistant/Dip Treatment)

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) heavily infected by all stages of the spider mite (*Tetranychus urticae*) are dipped into a preparation of the active compound of the desired concentration.

After the specified period of time, the destruction in % is determined. 100% means that all spider mites have been killed; 0% means that none of the spider mites have been killed.

In this test, a destruction of 100% was caused, after 5 days, for example by the compounds of preparation examples (I-1-a-1), (I-1-a-2), (I-1-a-3), (I-1-b-2) and (I-2-b-1) at an exemplary active compound concentration of 0.1%.

What is claimed is:
1. A compound of the formula (I)

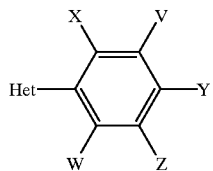

(I)

wherein

V represents hydrogen, halogen, alkyl or alkoxy,

W represents cyano, nitro, halogen, alkyl, alkenyl, alkynyl, alkoxy, halogenoalkyl, halogenoalkoxy, unsubstituted or substituted phenyl, phenoxy, phenylthio, phenylalkoxy or phenylalkylthio, X represents hydrogen, halogen, alkyl, alkenyl, alkynyl, alkoxy, halogenoalkyl, halogenoalkoxy, cyano, nitro or unsubstituted or substituted phenyl, phenoxy, phenylthio, phenylalkyloxy or phenylalkylthio, Y represents hydrogen, halogen, alkyl, alkoxy, halogenoalkyl, halogenoalkoxy, cyano or nitro, Z represents halogen, alkyl, alkoxy, halogenoalkyl, halogenoalkoxy, hydroxyl, cyano, nitro or unsubstituted or substituted phenoxy, phenylthio, 5- to 6-membered hetaryloxy, 5- to 6-membered hetarylthio, phenylalkyloxy or phenylalkylthio, Y and Z represent together with the carbon atoms that they are attached to an unsubstituted or substituted cycle which is uninterrupted or interrupted by one or more heteroatoms, V, X and W having one of the above-mentioned meanings, or W and Z represent together with the carbon atoms that they are attached to an unsubstituted or substituted cycle which is uninterrupted or interrupted by one or more heteroatoms, V, X and Y having one of the above-mentioned meanings, Het represents one of the groups

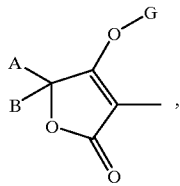

(2)

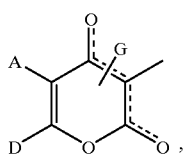

(3)

wherein

A represents hydrogen, unsubstituted or halogen-substituted alkyl, alkenyl, alkoxyalkyl, polyalkoxyalkyl or alkylthioalkyl, saturated or unsaturated and unsubstituted or substituted cycloalkyl or heterocyclyl or unsubstituted or halogen-, alkyl-, halogenoalkyl-, alkoxy-, halogenoalkoxy-, cyano- or nitro- substituted aryl, arylalkyl or hetaryl, B represents hydrogen, alkyl or alkoxyalkyl, or A and B represent together with the carbon atom that they are attached to a saturated or unsaturated unsubstituted or substituted carbocycle or heterocycle, D represents hydrogen or an unsubstituted or substituted radical from the group consisting of alkyl, alkenyl, alkynyl, alkoxyalkyl, polyalkoxyalkyl, alkylthioalkyl, saturated or unsaturated cycloalkyl, saturated or unsaturated heterocyclyl, arylalkyl, aryl, hetarylalkyl or hetaryl, or A and D represent together with the atoms that they are attached to an unsubstituted or substituted carbocycle or heterocycle, G represents hydrogen (a) or one of the groups (b)
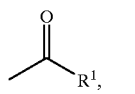

(c)
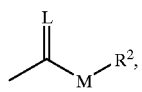

(d)
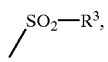

(e)
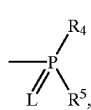

E or (f)

(g)
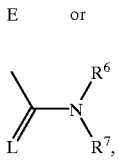

wherein

E represents a metal ion equivalent or an ammonium ion,

L represents oxygen or sulfur,

M represents oxygen or sulfur, $R^1$ represents unsubstituted or halogen-substituted alkyl, alkenyl, alkoxyalkyl, alkylthioalkyl or polyalkoxyalkyl or unsubstituted or halogen-, alkyl- or alkoxy-substituted cycloalkyl or heterocyclyl or unsubstituted or substituted phenyl, phenylalkyl, hetaryl, phenoxyalkyl or hetaryloxyalkyl, $R^2$ represents unsubstituted or halogen-substituted alkyl, alkenyl, alkoxyalkyl or polyalkoxyalkyl or unsubstituted or substituted cycloalkyl, phenyl or benzyl, $R^3$, $R^4$ and $R^5$ each represent independently of one another unsubstituted or halogen-substituted alkyl, alkoxy, alkylamino, dialkylamino, alkylthio, alkenylthio or cycloalkylthio or unsubstituted or substituted phenyl benzyl, phenoxy or phenylthio, $R^6$ and $R^7$ each represent independently of one another hydrogen, unsubstituted or halogen-substituted alkyl, cycloalkyl, alkenyl, alkoxy or alkoxyalkyl or unsubstituted or substituted phenyl or benzyl, or represent together with the N-atom that they are attached to an unsubstituted or oxygen- or sulfur-containing and unsubstituted or substituted cycle, excluding the following compounds

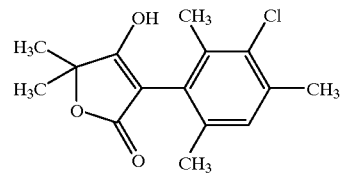

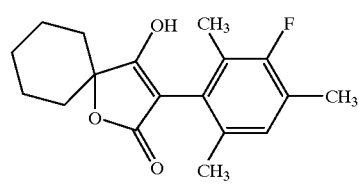

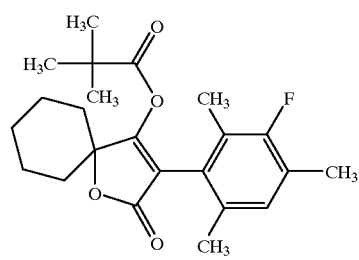

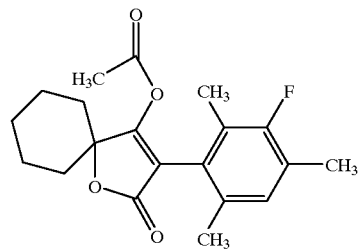

2. A compound of the formula (I) according to claim 1 wherein

V represents hydrogen, halogen, $C_1$–$C_6$-alkyl or $C_1$–$C_6$-alkoxy,

W represents cyano, nitro, halogen, $C_1$–$C_6$-alkyl, $C_2$–$C_6$-alkenyl, $C_2$–$C_6$-alkynyl, $C_1$–$C_6$-alkoxy, $C_1$–$C_4$-halogenoalkyl, $C_1$–$C_4$-halogenoalkoxy or unsubstituted or halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenoxy, phenylthio, phenyl-$C_1$–$C_4$-alkoxy or phenyl-$C_1$–$C_4$-alkylthio, X represents hydrogen, halogen, $C_1$–$C_6$-alkyl, $C_2$–$C_6$-alkenyl, $C_2$–$C_6$-alkynyl, $C_1$–$C_6$-alkoxy, $C_1$–$C_4$-halogenoalkyl, $C_1$–$C_4$-halogenoalkoxy, cyano, nitro or unsubstituted or halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenoxy, phenylthio, phenyl-$C_1$–$C_4$-alkoxy or phenyl-$C_1$–$C_4$-alkylthio, Y represents hydrogen, halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, Z represents halogen, $C_1$–$C_6$-alkyl, $C_1$–$C_6$-alkoxy, $C_1$–$C_4$-halogenoalkyl, $C_1$–$C_4$-halogenoalkoxy, hydroxyl, cyano, nitro or unsubstituted or halogen-, $C_1$–$C_4$-alkyl-, $C_1$–$C_4$-alkoxy-, $C_1$–$C_4$-halogenoalkyl-, $C_1$–$C_4$-halogenoalkoxy-, nitro- or cyano-substituted phenoxy, phenylthio, thiazolyloxy, pyridinyloxy, pyrimidyloxy, pyrazolyloxy, phenyl-$C_1$–$C_4$-alkyloxy or phenyl-$C_1$–$C_4$-alkylthio, or, Y and Z together represent unsubstituted or halogen-, $C_1$–$C_6$-alkyl-, $C_1$–$C_6$-alkoxy- or $C_1$–$C_4$-halogenoalkyl-substituted $C_3$–$C_5$-alkanediyl or $C_3$–$C_5$-alkenediyl in which zero to three members are replaced independently of one another by oxygen, sulfur, nitrogen or a carbonyl group, or W and Z together represent unsubstituted or halogen-, $C_1$–$C_6$-alkyl-, $C_1$–$C_6$-alkoxy- or $C_1$–$C_4$-halogenoalkyl-substituted $C_3$–$C_5$-alkanediyl or $C_3$–$C_5$-alkenediyl in which zero to three members are replaced independently of one another by oxygen, sulfur, nitrogen or a carbonyl group, A represents hydrogen, unsubstituted or halogen-substituted $C_1$–$C_{12}$-alkyl, $C_2$–$C_8$-alkenyl, $C_1$–$C_{10}$-alkoxy-$C_1$–$C_8$-alkyl, poly-$C_1$–$C_8$-alkoxy-$C_1$–$C_8$-alkyl or $C_1$–$C_{10}$-alkylthio-$C_1$–$C_6$-alkyl, unsubstituted or halogen-, $C_1$–$C_6$-alkyl- or $C_1$–$C_6$-alkoxy-substituted $C_3$–$C_8$-cycloalkyl in which zero, one or two not directly adjacent methylene groups are replaced by a compound selected from the group consisting of oxygen and sulfur, or represents unsubstituted or halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano-, or nitro-substituted phenyl, naphthyl, phenyl-$C_1$–$C_6$-alkyl, naphthyl-$C_1$–$C_6$-alkyl or hetaryl having 5 or 6 ring atoms and one to three heteroatoms from the group consisting of oxygen, sulfur and nitrogen, B represents hydrogen, $C_1$–$C_{12}$-alkyl or $C_1$–$C_8$-alkoxy-$C_1$–$C_6$-alkyl or A, B and the carbon atom that they are attached to represent $C_3$–$C_{10}$-cycloalkyl or $C_5$–$C_{10}$-cycloalkenyl, where in each case, zero or one methylene group is replaced by oxygen or sulfur and which is unsubstituted or substituted by $C_1$–$C_8$-alkyl, $C_3$–$C_{10}$-cycloalkyl, $C_1$–$C_8$-halogenoalkyl, $C_1$–$C_8$-alkoxy, $C_1$–$C_8$-alkylthio, halogen or phenyl, or A, B and the carbon atom that they are attached to represent $C_5$–$C_6$-cycloalkyl which is substituted by an alkylenediyl group containing zero, one or two compounds selected from the group consisting of oxygen and sulfur, or by an alkylenedioxy group or alkylenedithioyl group forming a further five- to eight-membered ring with the carbon atom that it is attached to, or A, B and the carbon atom that they are attached to represent $C_3$–$C_8$-cycloalkyl or $C_5$–$C_8$-cycloalkenyl in which two carbon atoms are connected by $C_1$–$C_6$-alkyl-, $C_1$–$C_6$-alkoxy- or halogen-substituted $C_3$–$C_6$-alkanediyl, $C_3$–$C_6$-alkenediyl or $C_4$–$C_6$-alkanedienediyl where in each case zero or one methylene group is replaced by oxygen or sulfur, D represents hydrogen, unsubstituted or halogen-substituted $C_1$–$C_{12}$-alkyl, $C_3$–$C_8$-alkenyl, $C_3$–$C_8$-alkynyl, $C_1$–$C_{10}$-alkoxy-$C_2$–$C_8$-alkyl, poly-$C_1$–$C_8$-alkoxy-$C_2$–$C_8$-alkyl or $C_1$–$C_{10}$-alkylthio-$C_2$–$C_8$-alkyl, unsubstituted or halogen-, $C_1$–$C_4$-alkyl-, $C_1$–$C_4$-alkoxy- or $C_1$–$C_4$-halogeno-alkyl-substituted $C_3$–$C_8$-cycloalkyl in which zero, one or two not directly adjacent methylene groups are replaced by a compound selected from the group consisting of oxygen and sulfur, or represents unsubstituted or halogen-, $C_1$–$C_6$-alkyl-, $C_1$–$C_6$-halogenoalkyl-, $C_1$–$C_6$-alkoxy-, $C_1$–$C_6$-halogeno-alkoxy-, cyano- or nitro-substituted phenyl, hetaryl having 5 to 6 ring atoms and one or two heteroatoms from the group consisting of oxygen, sulfur and nitrogen, phenyl-$C_1$–$C_6$-alkyl or hetaryl-$C_1$–$C_6$-alkyl having 5 to 6 ring atoms and one or two heteroatoms from the group consisting of oxygen, sulfur and nitrogen, or A and D together represent a $C_3$–$C_6$-alkanediyl, $C_3$–$C_6$-alkenediyl or $C_4$–$C_6$-alkadienediyl group in which in each case one methylene group is replaced by oxygen or sulfur and which are unsubstituted or substituted by halogen or by unsubstituted or halogen-substituted $C_1$–$C_{10}$-alkyl, $C_1$–$C_6$-alkoxy, $C_1$–$C_6$-alkylthio, $C_3$–$C_7$-cycloalkyl, phenyl or benzyloxy or by a further $C_3$–$C_6$-alkanediyl, $C_3$–$C_6$-alkenediyl or $C_4$–$C_6$-alkadienediyl group forming a fused-n ring where in each case one methylene group is replaced by oxygen or sulfur and which are unsubstituted or substituted by $C_1$–$C_6$-alkyl, or A and D together represent a $C_3$–$C_6$-alkanediyl or $C_3$–$C_6$-alkenediyl group, each of which contains one of the following groups

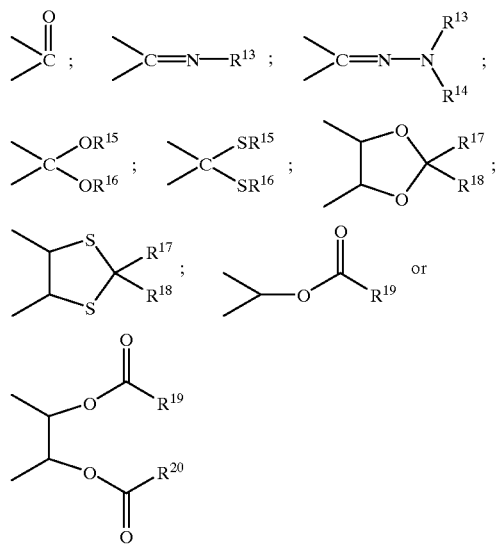

$R^1$ represents unsubstituted or halogen-substituted $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or poly-$C_1$–$C_8$-alkoxy-$C_1$–$C_8$-alkyl, or unsubstituted or halogen-, $C_1$–$C_6$-alkyl- or $C_1$–$C_6$-alkoxy-substituted $C_3$–$C_8$-cycloalkyl in which zero, one or two not directly adjacent methylene groups are replaced by a compound selected from the group consisting of oxygen and sulfur, unsubstituted or halogen-, cyano-, nitro-, $C_1$–$C_6$-alkyl-, $C_1$–$C_6$-alkoxy-, $C_1$–$C_6$-halogenoalkyl-, $C_1$–$C_6$-halogenoalkoxy-, $C_1$–$C_6$-alkylthio- or $C_1$–$C_6$-alkylsulphonyl-substituted phenyl, unsubstituted or halogen-, nitro-, cyano-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$–$C_6$-alkyl, unsubstituted or halogen- or $C_1$–$C_6$-alkyl-substituted 5- or 6-membered hetaryl having one or two heteroatoms from the group consisting of oxygen, sulfur and nitrogen, unsubstituted or halogen- or $C_1$–$C_6$-alkyl-substituted phenoxy-$C_1$–$C_6$-alkyl or unsubstituted or halogen-, amino- or $C_1$–$C_6$-alkyl-substituted 5- or 6-membered hetaryloxy-$C_1$–$C_6$-alkyl having one or two heteroatoms from the group consisting of oxygen, sulfur and nitrogen, $R^2$ represents unsubstituted or halogen-substituted $C_1$–$C_{20}$-alkyl, $C_2$–$C_{20}$-alkenyl, $C_1$–$C_8$-alkoxy-$C_2$–$C_8$-alkyl or poly-$C_1$–$C_8$-alkoxy-$C_2$–$C_8$-alkyl, unsubstituted or halogen-, $C_1$–$C_6$-alkyl- or $C_1$–$C_6$-alkoxy-substituted $C_3$–$C_8$-cycloalkyl or unsubstituted or halogen-, cyano-, nitro-, $C_1$–$C_6$-alkyl-, $C_1$–$C_6$-alkoxy-, $C_1$–$C_6$-halogenoalkyl or $C_1$–$C_6$-halogenoalkoxy-substituted phenyl or benzyl, $R^3$ represents unsubstituted or halogen-substituted $C_1$–$C_8$-alkyl or unsubstituted or halogen-, $C_1$–$C_6$-alkyl-, $C_1$–$C_6$-alkoxy-, $C_1$–$C_4$-halogenoalkyl-, $C_1$–$C_4$-halogenoalkoxy-, cyano- or nitro-substituted phenyl or benzyl, $R^4$ and $R^5$ each represent independently of one another unsubstituted or halogen-substituted $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio or $C_3$–$C_8$-alkenylthio, unsubstituted or halogen-, nitro, cyano-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkyl- or $C_1$–$C_4$-halogenoalkyl-substituted phenyl, phenoxy or phenylthio, $R^6$ and $R^7$ represent independently of one another hydrogen, unsubstituted or halogen-substituted $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_2$–$C_8$-alkyl, unsubstituted or halogen-, $C_1$–$C_8$-alkyl-, $C_1$–$C_8$-halogenoalkyl- or $C_1$–$C_8$-alkoxy-substituted phenyl or benzyl or together represent an unsubstituted or $C_1$–$C_6$-alkyl-substituted $C_3$–$C_6$-alkylene radical in which zero or one methylene group is replaced by oxygen or sulfur, $R^{13}$ represents hydrogen or unsubstituted or halogen-substituted $C_1$–$C_8$-alkyl or $C_1$–$C_8$-alkoxy, unsubstituted or halogen-, $C_1$–$C_4$-alkyl- or $C_1$–$C_4$-alkoxy-substituted $C_3$–$C_8$-cycloalkyl in which zero or one methylene group is replaced by oxygen or sulfur, or unsubstituted or halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenyl-$C_1$–$C_4$-alkyl or phenyl-$C_1$–$C_4$-alkoxy, $R^{14}$ represents hydrogen or $C_1$–$C_8$-alkyl or $R^{13}$ and $R^{14}$ together represent $C_4$–$C_6$-alkanediyl, $R^{15}$ and $R^{16}$ are identical or different and represent $C_1$–$C_6$-alkyl or $R^{15}$ and $R^{16}$ together represent a $C_2$–$C_4$-alkanediyl radical which is unsubstituted or substituted by $C_1$–$C_6$-alkyl or by unsubstituted or halogen-, $C_1$–$C_4$-alkyl-, $C_1$–$C_4$-halogenoalkyl-, $C_1$–$C_4$-alkoxy-, $C_1$–$C_4$-halogenoalkoxy-, nitro- or cyano-substituted phenyl, $R^{17}$ and $R^{18}$ each represent independently of one another hydrogen, unsubstituted or halogen-substituted $C_1$–$C_8$-alkyl or unsubstituted or halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl or $R^{17}$ and $R^{18}$ represent together with the carbon atom that they are attached to unsubstituted or $C_1$–$C_4$-alkyl-substituted $C_5$–$C_7$-cycloalkyl in which zero or one methylene group is replaced by oxygen or sulfur and $R^{19}$ and $R^{20}$ each represent independently of one another $C_1$–$C_{10}$-alkyl, $C_2$–$C_{10}$-alkenyl, $C_1$–$C_{10}$-alkoxy, $C_1$–$C_{10}$-alkylamino, $C_3$–$C_{10}$-alkenylamino, di-($C_1$–$C_{10}$-alkyl)amino or di-($C_3$–$C_{10}$-alkenyl)amino.

3. A compound of the formula (I) according to claim 1 wherein

V represents hydrogen, fluorine, chlorine, bromine, $C_1$–$C_4$-alkyl of $C_1$–$C_4$-alkoxy, W represents cyano, nitro, fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy or unsubstituted or fluorine-, chlorine-, bromine-, $C_1$–$C_4$-alkyl, $C_1$–$C_4$-alkoxy-, $C_1$–$C_2$-halogenoalkyl-, $C_1$–$C_2$-halogenoalkoxy-, nitro- or cyano-substituted phenyl, phenoxy, benzyl or benzyloxy, X represents hydrogen, fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano, nitro or unsubstituted or fluorine-, chlorine-, bromine-, $C_1$–$C_4$-alkyl-, $C_1$–$C_4$-alkoxy-, $C_1$–$C_2$-halogenoalkyl-, $C_1$–$C_2$-halogenoalkoxy-, nitro- or cyano-substituted phenyl, phenoxy, benzyl or benzyloxy, Y represents hydrogen, fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, Z represents fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, hydroxyl, cyano, nitro or unsubstituted or fluorine-, chlorine-, bromine-, $C_1$–$C_4$-alkyl-, $C_1$–$C_4$-alkoxy-, $C_1$–$C_2$halogenoalkyl-, $C_1$–$C_2$-halogenoalkoxy-, nitro- or cyano-substituted phenoxy or benzyloxy, or Y and Z together represent unsubstituted or fluorine-, chlorine-, bromine-, $C_1$–$C_4$-alkyl-, $C_1$–$C_4$-alkoxy- or $C_1$–$C_2$-halogenoalkyl-substituted $C_3$–$C_4$-alkanediyl or $C_3$–$C_4$-alkenediyl in which zero, one or two not directly adjacent members are replaced independently of one another by oxygen, sulfur or nitrogen, or W and Z together represent unsubstituted or fluorine-, chlorine-, bromine-, $C_1$–$C_4$-alkyl-, $C_1$–$C_4$-alkoxy- or $C_1$–$C_2$-halogenoalkyl-substituted $C_3$–$C_4$-alkanediyl or $C_3$–$C_4$-alkenyldiyl in which zero, one or two not directly adjacent members are replaced independently of one another by oxygen, sulfur or nitrogen, A represents hydrogen, unsubstituted or fluorine- or chlorine-substituted $C_1$–$C_{10}$-alkyl, $C_2$–$C_6$-alkenyl, $C_1$–$C_8$-alkoxy-$C_1$–$C_6$-alkyl, poly-$C_1$–$C_6$-alkoxy-$C_1$–$C_6$-alkyl or $C_1$–$C_8$-alkylthio-$C_1$–$C_6$-alkyl or unsubstituted or fluorine-, chlorine-, or $C_1$–$C_4$-alkyl or $C_1$–$C_4$-alkoxy-substituted $C_3$–$C_7$-cycloalkyl in which zero, one or two not directly adjacent methylene groups are replaced by a compound selected from the group consisting of oxygen and sulfur, or unsubstituted or fluorine-, chlorine-, bromine-, $C_1$–$C_4$-alkyl-, $C_1$–$C_4$-halogenoalkyl-, $C_1$–$C_4$-alkoxy-, $C_1$–$C_4$-halogenoalkoxy-, cyano- or nitro-substituted phenyl, furanyl, pyridyl, imidazolyl, triazolyl, pyrazolyl, indolyl, thiazolyl, thienyl or phenyl-$C_1$–$C_4$-alkyl, B represents hydrogen, $C_1$–$C_{10}$-alkyl or $C_1$–$C_6$-alkoxy-$C_1$–$C_4$-alkyl or A, B and the carbon atom that they are attached to represent $C_3$–$C_8$-cycloalkyl or $C_5$–$C_8$-cycloalkenyl in which zero or one methylene group is replaced by oxygen or sulfur and which are unsubstituted or substituted by $C_1$–$C_6$-alkyl, $C_3$–$C_8$-cycloalkyl, $C_1$–$C_3$-halogenoalkyl, $C_1$–$C_6$-alkoxy, $C_1$–$C_6$-alkylthio, fluorine, chlorine or phenyl, or A, B and the carbon atom that they are attached to represent $C_5$–$C_6$-cycloalkyl which is substituted by an alkylenediyl group containing zero, one or two oxygen or sulfur atoms, or by an alkylenedioxy or alkylenedithiol group forming a further five- to seven-membered ring with the carbon atom that it is attached to or A, B and the carbon atom that they are attached to represent $C_3$–$C_6$-cycloalkyl or $C_5$–$C_6$-cycloalkenyl in which two carbon atoms are connected by unsubstituted or $C_1$–$C_4$-alkyl-, $C_1$–$C_4$-alkoxy-, fluorine-, chlorine- or bromine-substituted $C_3$–$C_5$-alkanediyl, $C_3$–$C_5$-alkenediyl or butadienediyl in which zero or one methylene group is replaced by oxygen or sulfur, D represents hydrogen, unsubstituted or fluorine- or chlorine-substituted $C_1$–$C_{10}$-alkyl, $C_3$–$C_6$-alkenyl, $C_3$–$C_6$-alkynyl, $C_1$–$C_8$-alkoxy-$C_2$–$C_6$-alkyl, poly-$C_1$–$C_6$-alkoxy-$C_2$–$C_6$-alkyl or $C_1$–$C_8$-alkylthio-$C_2$–$C_6$-alkyl, unsubstituted or fluorine-, chlorine-, $C_1$–$C_4$-alkyl-, $C_1$–$C_4$-alkoxy- or $C_1$–$C_2$-halogenoalkyl-substituted $C_3$–$C_7$-cycloalkyl in which one or two not directly adjacent methylene groups are replaced by a compound selected from the group consisting of oxygen and sulfur, or represents unsubstituted or fluorine-, chlorine-, bromine-, $C_1$–$C_4$-alkyl-, $C_1$–$C_4$-halogenoalkyl-, $C_1$–$C_4$-alkoxy-, $C_1$–$C_4$-halogenoalkoxy-, cyano- or nitro-substituted phenyl, furanyl, imidazolyl, pyridyl, thiazolyl, pyrazolyl, pyrimidyl, pyrrolyl, thienyl, triazolyl or phenyl-$C_1$–$C_4$-alkyl or A and D represent a $C_3$–$C_5$-alkanediyl or $C_3$–$C_5$-alkenediyl group in which one carbon atom is replaced by oxygen or sulfur and which are unsubstituted or substituted by fluorine, chlorine or unsubstituted or fluorine- or chlorine-substituted $C_1$–$C_6$-alkyl, $C_1$–$C_4$-alkoxy, $C_1$–$C_4$-alkylthio, $C_3$–$C_6$-cycloalkyl, phenyl or benzyloxy or which respectively optionally contain one of the following groups:

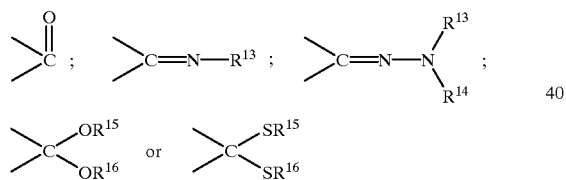

$R^1$ represents unsubstituted or fluorine- or chlorine-substituted $C_1$–$C_{16}$-alkyl, $C_2$–$C_{16}$-alkenyl, $C_1$–$C_6$-alkoxy-$C_1$–$C_6$-alkyl, $C_1$–$C_6$-alkyl-thio-$C_1$–$C_6$-alkyl or poly-$C_1$–$C_6$-alkoxy-$C_1$–$C_6$-alkyl or unsubstituted or fluorine-, chlorine-, $C_1$–$C_5$-alkyl- or $C_1$–$C_5$-alkoxy-substituted $C_3$–$C_7$-cycloalkyl in which zero, one or two not directly adjacent methylene groups are replaced by a compound selected from the group consisting of oxygen and sulfur, unsubstituted or fluorine-, chlorine-, bromine-, cyano-, nitro-, $C_1$–$C_4$-alkyl-, $C_1$–$C_4$-alkoxy-, $C_1$–$C_3$-halogenoalkyl-, $C_1$–$C_3$-halogenoalkoxy-, $C_1$–$C_4$-alkylthio- or $C_1$–$C_4$-alkylsulphonyl-substituted phenyl, unsubstituted or fluorine-, chlorine-, bromine-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl-$C_1$–$C_4$-alkyl, unsubstituted or fluorine-, chlorine-, bromine- or $C_1$–$C_4$-alkyl-substituted pyrazolyl, thiazolyl, pyridyl, pyrimidyl, furanyl or thienyl, unsubstituted or fluorine-, chlorine-, bromine- or $C_1$–$C_4$-alkyl-substituted phenoxy-$C_1$–$C_5$-alkyl or unsubstituted or fluorine-, chlorine-, bromine-, amino- or $C_1$–$C_4$-alkyl-substituted pyridyloxy-$C_1$–$C_5$-alkyl, pyrimidyloxy-$C_1$–$C_5$-alkyl or thiazolyloxy-$C_1$–$C_5$-alkyl, $R^2$ represents unsubstituted or fluorine- or chlorine-substituted $C_1$–$C_{16}$-alkyl, $C_2$–$C_{16}$-alkenyl, $C_1$–$C_6$-alkoxy-$C_2$–$C_6$-alkyl or poly-$C_1$–$C_6$-alkoxy-$C_2$–$C_6$-alkyl, unsubstituted or fluorine-, chlorine-, $C_1$–$C_4$-alkyl- or $C_1$–$C_4$-alkoxy-substituted $C_3$–$C_7$-cycloalkyl or unsubstituted or fluorine-, chlorine-, bromine-, cyano-, nitro-, $C_1$–$C_4$-alkyl-, $C_1$–$C_3$-alkoxy-, $C_1$–$C_3$-halogenoalkyl- or $C_1$–$C_3$-halogenoalkoxy-substituted phenyl or benzyl, $R^3$ represents unsubstituted or fluorine- or chlorine-substituted $C_1$–$C_6$-alkyl or unsubstituted or fluorine-, chlorine-, bromine-, $C_1$–$C_4$-alkyl-, $C_1$–$C_4$-alkoxy-, $C_1$–$C_2$-halogenoalkoxy-, $C_1$–$C_2$-halogenoalkyl-, cyano- or nitro-substituted phenyl or benzyl, $R^4$ and $R^5$ each represent independently of one another unsubstituted or fluorine- or chlorine-substituted $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio or $C_3$–$C_4$-alkenylthio or unsubstituted or fluorine-, chlorine-, bromine-, nitro-, cyano-, $C_1$–$C_3$-alkoxy-, $C_1$–$C_3$-halogenoalkoxy-, $C_1$–$C_3$-akylthio-, $C_1$–$C_3$-halogenoalkylthio, $C_1$–$C_3$-alkyl- or $C_1$–$C_3$-halogenoalkyl-substituted phenyl, phenoxy or phenylthio, $R^6$ and $R^7$ each represent independently of one another hydrogen, unsubstituted or fluorine- or chlorine-substituted $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_2$–$C_6$-alkyl, unsubstituted or fluorine-, chlorine-, bromine-, $C_1$–$C_5$-halogenoalkyl-, $C_1$–$C_5$-alkyl- or $C_1$–$C_5$-alkoxy-substituted phenyl or benzyl, or represent together an unsubstituted or $C_1$–$C_4$-alkyl-substituted $C_3$–$C_6$-alkylene radical in which zero or one methylene group is replaced by oxygen or sulfur, $R^{13}$ represents hydrogen or unsubstituted or fluorine- or chlorine-substituted $C_1$–$C_6$-alkyl or $C_1$–$C_6$-alkoxy, unsubstituted or fluorine-, $C_1$–$C_2$-alkyl- or $C_1$–$C_2$-alkoxy-substituted $C_3$–$C_7$cycloalkyl in which zero or one methylene group is replaced by oxygen or sulfur, or represents unsubstituted or fluorine-, chlorine-, bromine-, $C_1$–$C_5$-alkyl-, $C_1$–$C_5$-alkoxy-, $C_1$–$C_2$-halogenoalkyl-, $C_1$–$C_2$-halogenoalkoxy-, nitro- or cyano-substituted phenyl, phenyl-$C_1$–$C_3$-alkyl or phenyl-$C_1$–$C_2$-alkyloxy, $R^{15}$ and $R^{16}$ together represent a $C_2$–$C_3$-alkanediyl radical which is unsubstituted or substituted by $C_1$–$C_4$-alkyl or unsubstituted or fluorine-, chlorine-, bromine-, $C_1$–$C_2$-alkyl-, $C_1$–$C_2$-halogenoalkyl-, $C_1$–$C_2$-alkoxy-, $C_1$–$C_2$-halogenoalkoxy-, nitro- or cyano-substituted phenyl.

4. A compound of the formula (I) according to claim 1 wherein

V represents hydrogen, fluorine, chlorine, bromine, methyl, ethyl, propyl, isopropyl, tert-butyl, methoxy, ethoxy, propoxy or isopropoxy, W represents cyano, nitro, fluorine, chlorine, bromine, methyl, ethyl, propyl, butyl, isopropyl, isobutyl, tert-butyl, methoxy, ethoxy, propoxy, isopropoxy, trifluoromethyl, difluoromethoxy, trifluoromethoxy, phenyl or benzyloxy, X represents hydrogen, fluorine, chlorine, bromine, methyl, ethyl, propyl, butyl, isobutyl, isopropyl, tert-butyl, methoxy, ethoxy, propoxy, isopropoxy, trifluoromethyl, trifluoromethoxy, difluoromethoxy, cyano, nitro, phenyl or benzyloxy, Y represents hydrogen, fluorine, chlorine, bromine, methyl, ethyl, propyl, isopropyl, butyl, isobutyl, tert-butyl, methoxy, ethoxy, propoxy, isopropoxy, trifluoromethyl, trifluoromethoxy, difluoromethoxy, cyano or nitro, Z represents fluorine, chlorine, bromine, methyl, ethyl, propyl, butyl, isobutyl, isopropyl, tert-butyl, methoxy, ethoxy, propoxy, isopropoxy, trifluoromethyl, trifluoromethoxy, difluoromethoxy, cyano or nitro, or Y and Z together represent unsubstituted or fluorine-, chlorine-, methyl-, ethyl-, propyl-, isopropyl-, methoxy-, ethoxy-, propoxy-, isopropoxy- or trifluoromethyl-substituted $C_3$–$C_4$-alkanediyl in which zero or two not directly adjacent members are replaced by oxygen, or W and Z together represent unsubstituted or fluorine-, chlorine-, methyl-, ethyl-, propyl-, isopropyl-, methoxy-, ethoxy-, propoxy-, isopropoxy- or trifluoromethyl-substituted $C_3$–$C_4$-alkanediyl in which zero or two not directly adjacent members are replaced by oxygen, A represents hydrogen, unsubstituted or fluorine- or chlorine-substituted $C_1$–$C_8$-alkyl, $C_2$–$C_4$-alkenyl, $C_1$–$C_6$-alkoxy-$C_1$–$C_4$-alkyl, poly-$C_1$–$C_4$-alkoxy-$C_1$–$C_4$-alkyl or $C_1$–$C_6$-alkylthio-$C_1$–$C_4$-alkyl or unsubstituted or fluorine-, chlorine-, methyl- or methoxy-substituted $C_3$–$C_6$-cycloalkyl in which zero, one or two not directly adjacent methylene groups are replaced by a compound selected from the group consisting of oxygen and sulfur, or represents unsubstituted or fluorine-, chlorine-, bromine-, methyl-, ethyl-, n-propyl-, isopropyl-, methoxy-, ethoxy-, trifluoromethyl-, trifluoromethoxy-, cyano- or nitro-substituted phenyl, pyridyl or benzyl, B represents hydrogen, $C_1$–$C_8$-alkyl or $C_1$–$C_4$-alkoxy-$C_1$–$C_2$-alkyl or A, B and the carbon atom that they are attached to represent $C_3$–$C_8$-cycloalkyl or $C_5$–$C_8$-cycloalkenyl where in each case zero or one methylene group is replaced by oxygen or sulfur and which are unsubstituted or substituted by methyl, ethyl, n-propyl, isopropyl, butyl, isobutyl, sec-butyl, tert-butyl, cyclohexyl, trifluoromethyl, methoxy, ethoxy, n-propoxy, isopropoxy, butoxy, isobutoxy, sec-butoxy, tert-butoxy, methylthio, ethylthio, fluorine, chlorine or phenyl or A, B and the carbon atom that they are attached to represent $C_5$–$C_6$-cycloalkyl which is substituted by an alkylenediyl group containing zero or one oxygen or sulfur atom, or by an alkylenedioxy group forming a further five- or six-membered ring with the carbon atom that it is attached to or A, B and the carbon atom that they are attached to represent $C_3$–$C_6$-cycloalkyl or $C_5$–$C_6$-cycloalkenyl in which two carbon atoms are connected by $C_3$–$C_4$-alkanediyl, $C_3$–$C_4$-alkenediyl or butadienediyl, D represents hydrogen, unsubstituted fluorine- or chlorine-substituted $C_1$–$C_8$-alkyl, $C_3$–$C_4$-alkenyl, $C_3$–$C_4$-alkynyl, $C_1$–$C_6$-alkoxy-$C_2$–$C_4$-alkyl, poly-$C_1$–$C_4$-alkoxy-$C_2$–$C_4$-alkyl, $C_1$–$C_4$-alkylthio-$C_2$–$C_4$-alkyl or $C_3$–$C_6$-cycloalkyl in which zero, one or two not directly adjacent methylene groups are replaced by a compound selected from the group consisting of oxygen and sulfur, or represents unsubstituted or fluorine-, chlorine-, bromine-, methyl-, ethyl-, n-propyl-, isopropyl-, methoxy-, ethoxy-, trifluoromethyl-, trifluoromethoxy-, cyano-, or nitro-substituted phenyl, furanyl, pyridyl, thienyl or benzyl, or A and D together represent a $C_3$–$C_5$-alkanediyl or $C_3$–$C_5$-alkenediyl group where in each case one methylene group is replaced by oxygen or sulfur and which are unsubstituted or substituted by fluorine, chlorine or unsubstituted or fluorine- or chlorine-substituted $C_1$–$C_6$-alkyl or $C_1$–$C_4$-alkoxy, $R^1$ represents unsubstituted or fluorine- or chlorine-substituted $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, poly-$C_1$–$C_4$-alkoxy-$C_1$–$C_4$-alkyl or unsubstituted or fluorine-, chlorine-, methyl-, ethyl-, n-propyl-, i-propyl-, n-butyl-, i-butyl-, tert-butyl-, methoxy-, ethoxy-, n-propoxy- or isopropoxy-substituted $C_3$–$C_6$-cycloalkyl in which zero, one or two not directly adjacent methylene groups are replaced by a compound selected from the group consisting of oxygen and sulfur, unsubstituted or fluorine-, chlorine-, bromine-, cyano-, nitro-, methyl-, ethyl-, n-propyl-, i-propyl-, methoxy-, ethyoxy-, trifluoromethyl-, trifluoromethoxy-, methylthio-, ethylthio-, methylsulphonyl-, or ethylsulphonyl-substituted phenyl, unsubstituted or fluorine-, chlorine-, bromine-, methyl-, ethyl-, n-propyl-, i-propyl-, methoxy-, ethoxy-, trifluoromethyl- or trifluoromethoxy-substituted benzyl, unsubstituted or fluorine-, chlorine-, bromine-, methyl- or ethyl-substituted furanyl, thienyl or pyridyl, unsubstituted or fluorine-, chlorine-, methyl- or ethyl-substituted phenoxy-$C_1$–$C_4$-alkyl or unsubstituted or fluorine-, chlorine-, amino-, methyl- or ethyl-substituted pyridyloxy-$C_1$–$C_4$-alkyl, pyrimidyloxy-$C_1$–$C_4$-alkyl or thiazolyoxy-$C_1$–$C_4$-alkyl, $R^2$ represents unsubstituted or fluorine- or chlorine-substituted $C_1$–$C_{14}$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl, unsubstituted or fluorine-, chlorine-, methyl-, ethyl-, n-propyl-, isopropyl- or methoxy-substituted $C_3$–$C_6$-cycloalkyl, or unsubstituted or fluorine-, chlorine-, cyano-, nitro-, methyl-, ethyl-, n-propyl-, i-propyl-, methoxy-, ethoxy-, trifluoromethyl- or trifluoromethoxy-substituted phenyl or benzyl, $R^3$ represents unsubstituted or fluorine- or chlorine-substituted methyl, ethyl, propyl, isopropyl, butyl, tert-butyl, or unsubstituted or fluorine-, chlorine-, bromine-, methyl-, ethyl-, isopropyl-, tert-butyl-, methoxy-, ethoxy-, isopropoxy-, trifluoromethyl-, trifluoromethoxy-, cyano- or nitro-substituted phenyl or benzyl, $R^4$ and $R^5$ each represent independently of one another unsubstituted or fluorine- or ;chlorine-substituted $C_1$–$C_4$-alkyl, $C_1$–$C_4$-alkoxy, $C_1$–$C_4$-alkylamino, di-($C_1$–$C_4$-alkyl)amino or $C_1$–$C_4$-alkylthio or unsubstituted or fluorine-, chlorine-, bromine-, nitro-, cyano-, methyl-, methoxy-, trifluoromethyl- or trifluoromethoxy-substituted phenyl, phenoxy or phenylthio, $R^6$ and $R^7$ each represent independently of one another hydrogen, unsubstituted or fluorine- or chlorine-substituted $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_2$–$C_4$-alkyl, unsubstituted or fluorine-, chlorine-, bromine-, methyl-, methoxy- or trifluoromethyl-substituted phenyl or benzyl or together represent an unsubstituted or methyl- or ethyl-substituted $C_5$–$C_6$-alkylene radical in which zero or one methylene group is replaced by oxygen or sulfur.

5. A pesticide or herbicide comprising a compound of the formula (I) according to claim 1 and one or more extenders and/or surface-active agents.

6. A method for controlling pests or weeds comprising the step of allowing a compound of the formula (I) according to claim 1 to act on pests or weeds and/or their habitat.

7. A process for preparing a pesticide or a herbicide comprising the step of mixing a compound of the formula (I) according to claim 1 with extenders and/or surface-active agents.

* * * * *